(12) United States Patent
Dacosta et al.

(10) Patent No.: US 12,303,139 B2
(45) Date of Patent: *May 20, 2025

(54) ALIGNMENT GUIDES, CUT GUIDES, SYSTEMS AND METHODS OF USE AND ASSEMBLY

(71) Applicant: Paragon 28, Inc., Englewood, CO (US)

(72) Inventors: Albert Dacosta, Lone Tree, CO (US); Laura Zagrocki Brinker, Lone Tree, CO (US); Randy Allard, Golden, CO (US)

(73) Assignee: Paragon 28, Inc., Englewood, CO (US)

( * ) Notice: Subject to any disclaimer, the term of this patent is extended or adjusted under 35 U.S.C. 154(b) by 51 days.

This patent is subject to a terminal disclaimer.

(21) Appl. No.: 18/350,499

(22) Filed: Jul. 11, 2023

(65) Prior Publication Data

US 2024/0016502 A1 Jan. 18, 2024

Related U.S. Application Data

(63) Continuation of application No. 17/115,442, filed on Dec. 8, 2020, now Pat. No. 11,696,767, which is a (Continued)

(51) Int. Cl.
*A61B 17/15* (2006.01)
*A61B 17/16* (2006.01)
*A61B 17/17* (2006.01)

(52) U.S. Cl.
CPC .......... *A61B 17/15* (2013.01); *A61B 17/1682* (2013.01); *A61B 17/1775* (2016.11)

(58) Field of Classification Search
CPC ..... A61B 17/15; A61B 17/151; A61B 17/152; A61B 17/1682; A61B 17/17; A61B 17/1739; A61B 17/1775

See application file for complete search history.

(56) References Cited

U.S. PATENT DOCUMENTS 8,425,574 B2 4/2013 Huebner
9,936,994 B2 * 4/2018 Smith ................ A61B 17/1728
(Continued)

FOREIGN PATENT DOCUMENTS

| WO | 2017011656 | 1/2017 |
|----|------------|--------|
| WO | 2017031000 | 2/2017 |

(Continued)

*Primary Examiner* — Eric S Gibson
(74) *Attorney, Agent, or Firm* — Heslin Rothenberg Farley & Mesiti P.C.; Jacquelyn A. Graff, Esq.

(57) ABSTRACT

Guides, systems, and methods for maintaining, correcting and/or fusing joint deformities are disclosed. The guide system including a cut guide, an alignment guide, and at least one directional wire. The cut guide including a base portion, an extension member extending away from a bottom surface of the base portion, and at least one arm extending away from an end of the base portion. The alignment guide, including a base portion, a first extension member extending away from a bottom surface of the base portion in a first direction, and a second extension member extending away from the bottom surface of the base portion in a second direction. Methods of using a guide system for maintaining, correcting and/or fusing joint deformities are also disclosed.

20 Claims, 61 Drawing Sheets

Related U.S. Application Data continuation of application No. 16/516,857, filed on Jul. 19, 2019, now Pat. No. 10,856,886, which is a continuation of application No. PCT/US2018/064368, filed on Dec. 7, 2018.

(60) Provisional application No. 62/595,155, filed on Dec. 6, 2017.

(56) References Cited

U.S. PATENT DOCUMENTS

| | | | | |
|---|---|---|---|---|
| 10,335,220 | B2* | 7/2019 | Smith | A61B 17/152 |
| 10,342,590 | B2* | 7/2019 | Bays | A61B 17/1775 |
| 10,575,862 | B2* | 3/2020 | Bays | A61B 17/1775 |
| 10,856,886 | B2* | 12/2020 | Dacosta | A61B 17/15 |
| 11,696,767 | B2* | 7/2023 | Dacosta | A61B 17/151 606/87 |
| 2007/0265634 | A1 | 11/2007 | Weinstein | |
| 2011/0178524 | A1 | 7/2011 | Lawrence | |
| 2015/0223852 | A1 | 8/2015 | Lietz et al. | |
| 2016/0192950 | A1* | 7/2016 | Dayton | A61B 17/1682 606/87 |
| 2016/0213384 | A1 | 7/2016 | Fallin | |
| 2016/0235414 | A1* | 8/2016 | Hatch | A61B 17/1739 |
| 2016/0242791 | A1 | 8/2016 | Fallin et al. | |
| 2017/0042598 | A1* | 2/2017 | Santrock | A61B 17/152 |
| 2017/0056031 | A1* | 3/2017 | Awtrey | A61B 6/485 |
| 2017/0079669 | A1* | 3/2017 | Bays | A61B 17/8866 |
| 2017/0172638 | A1* | 6/2017 | Santrock | A61B 17/8866 |
| 2018/0317992 | A1* | 11/2018 | Santrock | A61B 17/1775 |
| 2019/0274745 | A1* | 9/2019 | Smith | A61B 17/1739 |
| 2019/0328435 | A1* | 10/2019 | Bays | A61B 17/151 |
| 2019/0328436 | A1* | 10/2019 | Bays | A61B 17/02 |
| 2019/0336140 | A1* | 11/2019 | Dacosta | A61B 17/151 |
| 2021/0085338 | A1* | 3/2021 | Dacosta | A61B 17/1682 |
| 2024/0016502 | A1* | 1/2024 | Dacosta | A61B 17/15 |

FOREIGN PATENT DOCUMENTS

| | | |
|---|---|---|
| WO | 2017031020 | 2/2017 |
| WO | 2018157168 | 8/2018 |

* cited by examiner

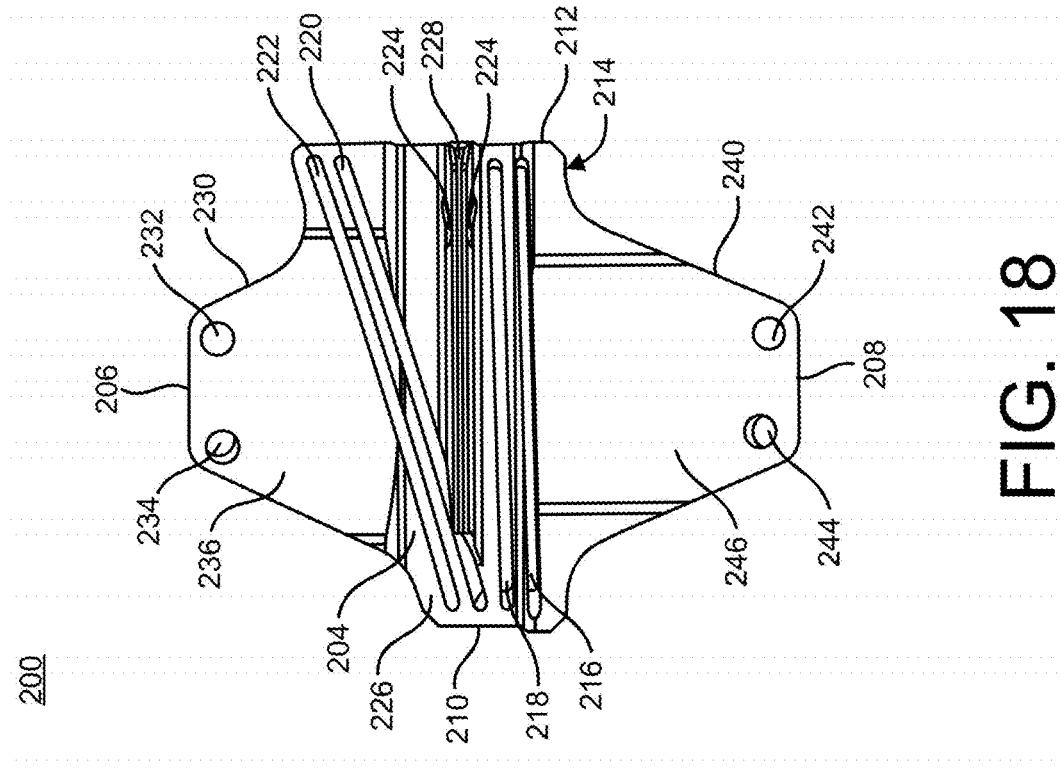
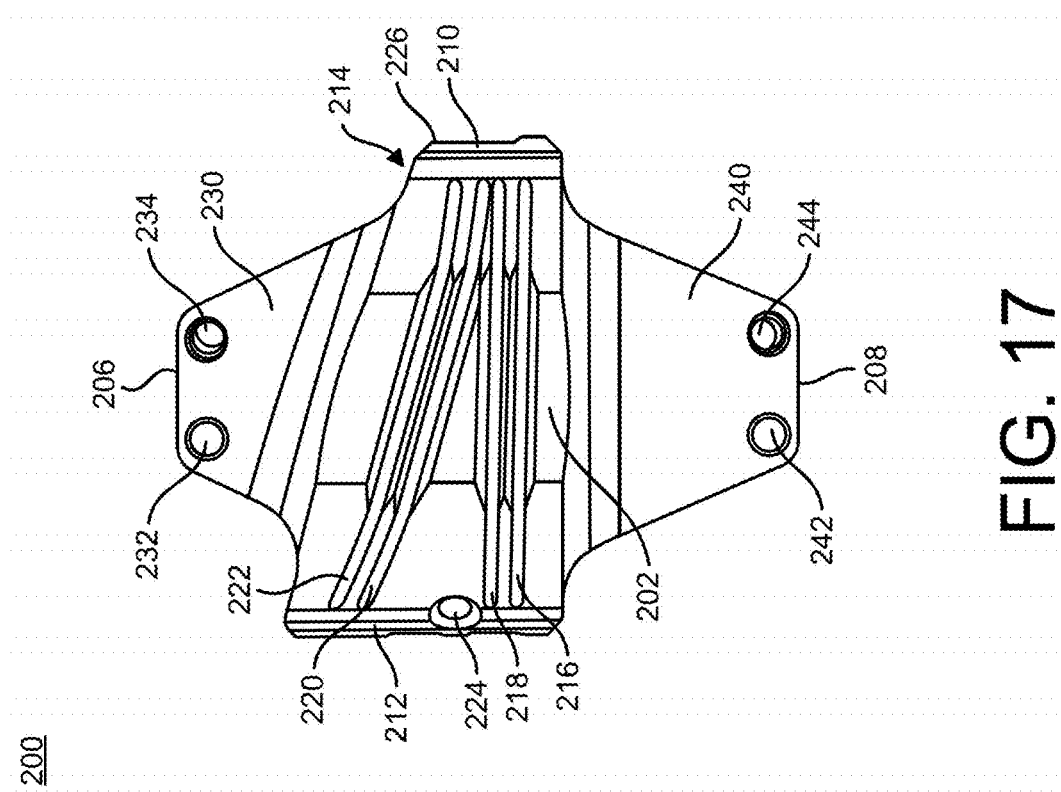

ALIGNMENT GUIDES, CUT GUIDES, SYSTEMS AND METHODS OF USE AND ASSEMBLY

CROSS REFERENCE TO RELATED APPLICATION

This application is a continuation of U.S. patent application Ser. No. 17/115,442 filed on Dec. 8, 2020 and entitled Alignment Guides, Cut Guides, Systems and Methods of Use and Assembly and which issued as U.S. Pat. No. 11,696,767 on Jul. 11, 2023, which is a continuation of U.S. patent application Ser. No. 16/516,857 filed on Jul. 19, 2019 and entitled Alignment Guides, Cut Guides, Systems and Methods of Use and Assembly, which issued as U.S. Pat. No. 10,856,886 on Dec. 8, 2020, which is a continuation of PCT/US2018/064368 filed on Dec. 7, 2018 and entitled Alignment Guides, Cut Guides, Systems and Methods of Use and Assembly, which claims priority benefit under 35 U.S.C. § 119(e) of U.S. provisional application No. 62/595,155, filed Dec. 6, 2017 and entitled Alignment Guides, Cut Guides, Systems and Methods of Use and Assembly, which are incorporated herein by reference in their entireties.

TECHNICAL FIELD

The present disclosure relates generally to general, podiatric, and orthopaedic surgery related to joint deformities. More specifically, but not exclusively, the present disclosure relates to devices, systems, and methods for maintaining, correcting and/or fusing joint deformities.

BACKGROUND OF THE INVENTION

The Lapidus procedure is commonly used to correct a hallux valgus deformity, which is a lateral deviation of the great toe, with subsequent hypermobility (or laxity). The Lapidus procedure is also commonly used to repair failed surgeries. Typically, a wedge of bone is removed in a biplanar direction at the distal end of the cuneiform, which will provide correction of the deformity and typically results in shortening of the first ray. The result of this shortening is a shift in weight distribution to the second ray, which can result in metatarsalgia. When the first ray is shortened, the function of the patient's sesamoids may also be affected because of the change in weight distribution on the sesamoids. Currently, to avoid shortening of the first ray when doing a Lapidus procedure, the accepted practice is for surgeons to make a straight transverse cut on the metatarsal, then cut only the cartilage or a minimal wedge resection of the cuneiform to obtain realignment of the transverse plane intermetatarsal angle as determined by the surgeon. If shortening beyond an acceptable amount occurs, a bone graft can be used to restore first ray length. Blood supply complications and anatomical height and weight bearing through the joint are all concerns for post-operative healing from a Lapidus procedure.

Accordingly, it is an object of the present invention to overcome one or more of the above-described drawbacks and/or disadvantages of the currently used procedures. For example, in view of the deficiencies of the current implants and methods of performing the Lapidus procedure and fusion of the first tarso-metatarsal joint, and similar implants and surgical methods for other areas of the body where multiple bone structures exist including, but not limited to, the hand, wrist and spine, it would be desirable to develop devices, systems, instrumentation, and methods for maintaining, correcting and/or fusing joint deformities to overcome the above-noted deficiencies of the currently available solutions for addressing joint deformities.

SUMMARY OF THE INVENTION

The present disclosure is directed toward devices, systems and methods for use in maintaining, correcting and/or fusing joint deformities.

In one aspect of the present disclosure provided herein, is a guide system. The guide system including a cut guide, an alignment guide coupled to the cut guide, and a directional wire engaging a portion of the alignment guide.

In another aspect of the present disclosure provided herein, is a cut guide. The cut guide including a base portion, an extension member extending away from a bottom surface of the base portion, and at least one arm extending away from an end of the base portion.

In yet another aspect of the present disclosure provided herein, is an alignment guide. The alignment guide, including a base portion, a first extension member extending away from a bottom surface of the base portion in a first direction, and a second extension member extending away from the bottom surface of the base portion in a second direction.

In a further aspect of the present disclosure provided herein, is a method for using the guide system. The method includes obtaining a cut guide, in which the cut guide includes a base portion, an extension member extending away from a bottom surface of the base portion, and at least one arm extending away from an end of the base portion. The method also includes inserting the extension member into a joint space and coupling the alignment guide to the cut guide. The method further includes inserting a directional wire into at least one opening in the alignment guide and inserting a k-wire into a dorsal hole in the cut guide and checking the orientation of the cut guide. In addition, the method includes inserting at least two wires through the at least one arm of the cut guide and into at least one bone and removing the alignment guide and k-wire. Next, the method includes cutting a first bone and a second bone using at least one slot of the cut guide and removing at least one lateral wire from the at least one bone and the cut guide. Then, the method includes moving the first and second bones to the desired correctional position.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 17 is a top view of the cut guide of FIG. 11, in accordance with an aspect of the present disclosure;

FIG. 18 is a bottom view of the cut guide of FIG. 11, in accordance with an aspect of the present disclosure;

DETAILED DESCRIPTION FOR CARRYING OUT THE INVENTION

Figure 1:
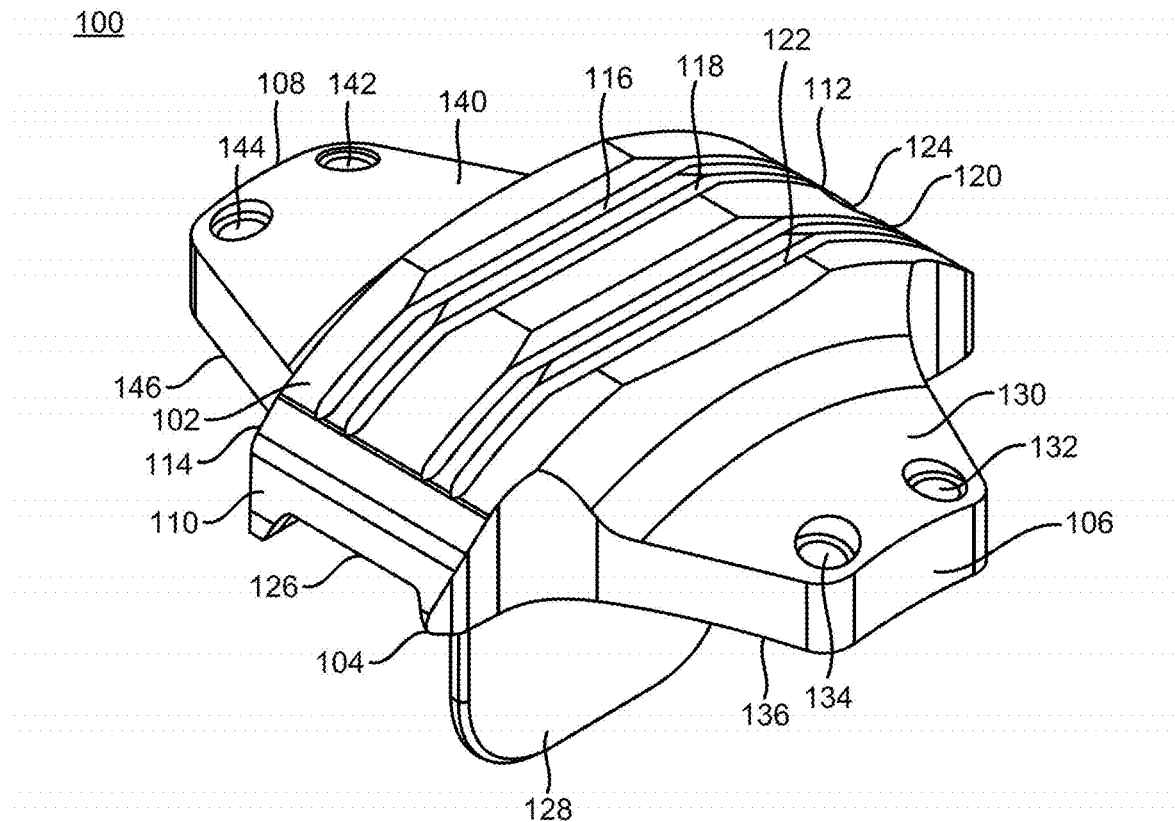
FIG. 1 is a top perspective view of one embodiment of a cut guide, in accordance with an aspect of the present disclosure.

Generally stated, disclosed herein are devices, systems, and methods for maintaining, correcting and/or fusing joint deformities. Further, methods for using the devices and systems for maintaining, correcting and/or fusing joint deformities are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the foot, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right foot may be mirrored so that they likewise function with the left foot. Further, the devices, systems, instrumentation and methods, and the aspects, components, features and the like thereof, disclosed herein are described with respect to the foot for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-8, there is illustrated a cut guide 100. The cut guide 100 includes a top surface 102, a bottom surface 104, a first or proximal end 106, a second or distal end 108, a first or medial side 110, and a second or lateral side 112. The cut guide 100 also includes a base portion 114 and a paddle, fin or extension member 128 extending away from the bottom surface 104 of the base portion 114. The cut guide 100 further includes a first or proximal arm 130 extending away from the base portion 114 on a first end 106 and a second or distal arm 140 extending away from the base portion 114 on a second end 108. The cut guide 100 may be, for example, a right foot cut guide.

Figure 4:
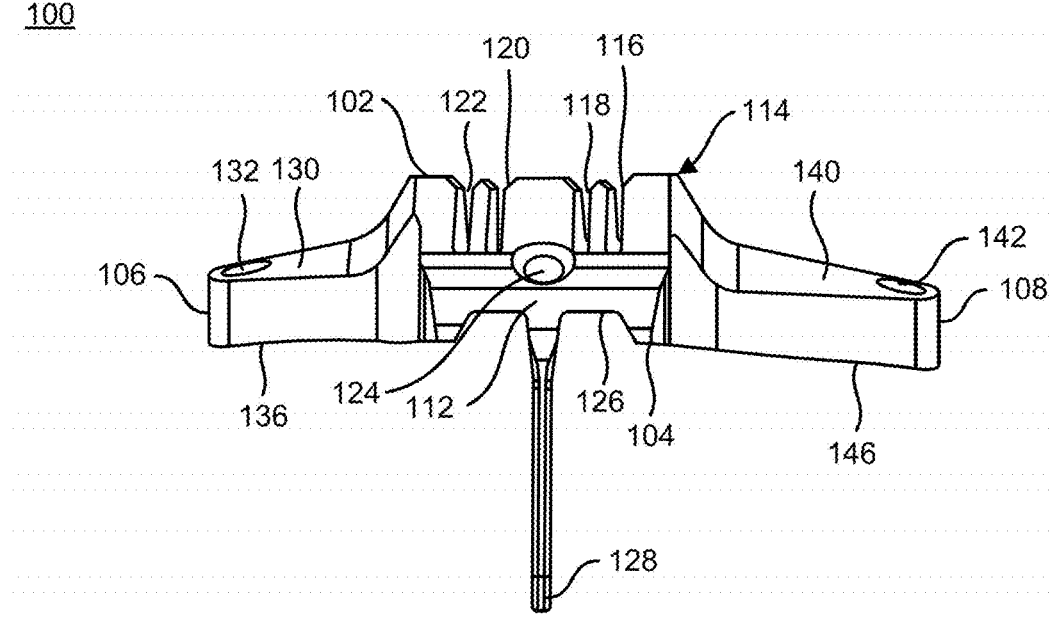
FIG. 4 is another side view of the cut guide of FIG. 1, in accordance with an aspect of the present disclosure.
Figure 5:
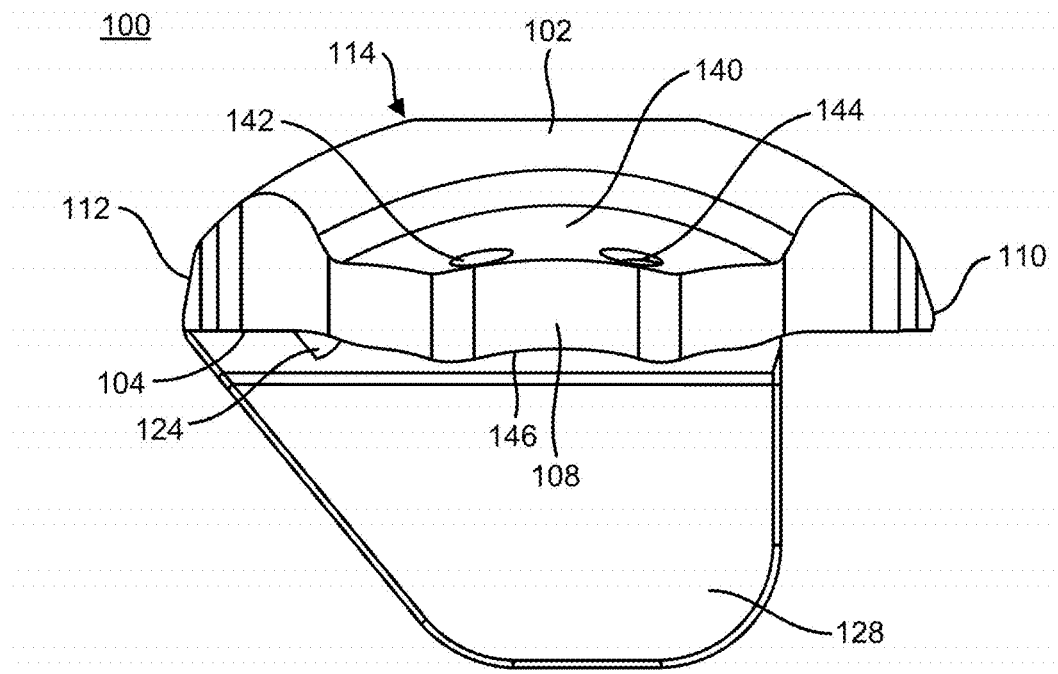
FIG. 5 is an end view of the cut guide of FIG. 1, in accordance with an aspect of the present disclosure.
Figure 6:
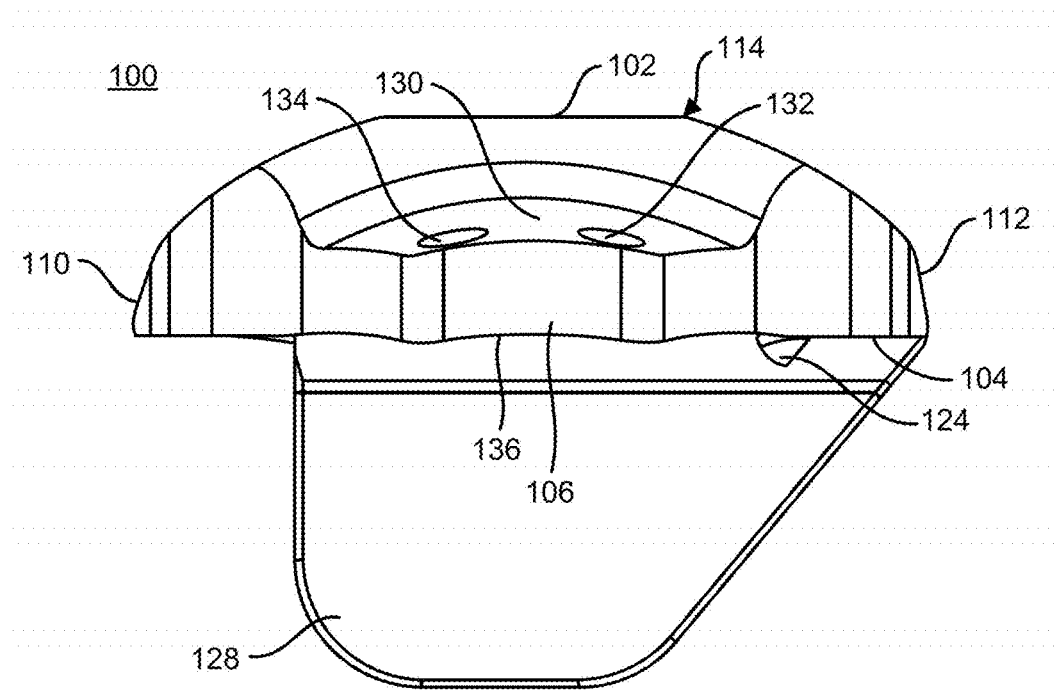
FIG. 6 is another end view of the cut guide of FIG. 1, in accordance with an aspect of the present disclosure.

As shown in FIGS. 1, 5 and 6, the top surface 102 of the base portion 114 may be, for example, curved or arced between the first side 110 and the second side 112. In one embodiment, the top surface 102 of the base portion 114 may include, for example, a flat or planar portion positioned between a first curvature or arc extending from the first side 110 to the flat portion and a second curvature or arc extending from a second side 112 to the flat portion. The base portion 114 also includes at least one slot 116, 118, 120, 122, as shown in FIGS. 1-4, 7 and 8. In the depicted embodiment, the base portion 114 includes a first slot 116 adjacent to a second slot 118 and a third slot 120 adjacent to a fourth slot 122. The first and second slots 116, 118 may be, for example, positioned on the second end 108 of the base portion 114 and the third and fourth slots 120, 122 may be, for example, positioned on the first end 106 of the base portion 114.

With continued reference to FIGS. 1-4 and 7, the slots 116, 118, 120, 122 may extend, for example, linearly through the base portion 114 from the top surface 102 to the bottom surface 104 of the cut guide 100. Alternatively, the slots 116, 118, 120, 122 may also be, for example, angled as the slots 116, 118, 120, 122 extend from the top surface 102 to the bottom surface 104. The slots 116, 118, 120, 122 may be angled, for example, approximately 1° to 4° and more specifically, approximately 2°, as they extend between the top surface 102 and the bottom surface 104. It is also contemplated that some of slots 116, 118, 120, 122 may be angled and other slots 116, 118, 120, 122 may be linear as they extend through the base portion 114 from the top surface 102 to the bottom surface 104.

In addition, the slots 116, 118, 120, 122 may be angled as they extend between the first side 110 and the second side 112, for example, the slots may be angled approximately 0° to as the slots 116, 118, 120, 122 extend between the first and second sides 110, 112. As shown, slots 116, 118, 120, 122 have an angle of 0° as the slots 116, 118, 120, 122 extend between the first and second sides 110, 112. Although not shown with respect to cut guide 100, it is also contemplated that a first set of slots 116, 118 may be angled as they extend between the first and second sides 110, 112 and the second set of slots 120, 122 may be straight, and vice versa. As shown, the slots 120, 122 are positioned to extend between the first and second sides 110, 112 parallel to the first metatarsal, as discussed in greater detail below with respect to the method of using the cut guide 100. The slots 116, 118, 120, 122 may be configured or sized and shaped to receive a saw blade and may have a width of, for example, approximately 0.58 mm to mm. The slots 116, 118, 120, 122 may be positioned, for example, to allow for removal of the articular cartilage layer of the two bones. To prevent resecting more bone than absolutely necessary, the slots 116, 118, 120, 122 may be positioned, for example, such that the medial portion of the slots 116, 118, 120, 122 are aligned with the intersection of the cartilage and bone. In one embodiment, the slots 116, 118 are positioned a first distance from the extension member 128, the slots 120, 122 are positioned a second distance from the extension member 128, and the first distance is smaller than the second distance. The first distance may be measured from the extension member 128 to an inner surface of the slots 116, 118 and the second distance may be measured from the extension member 128 to an inner surface of the slots 120, 122.

Figure 2:
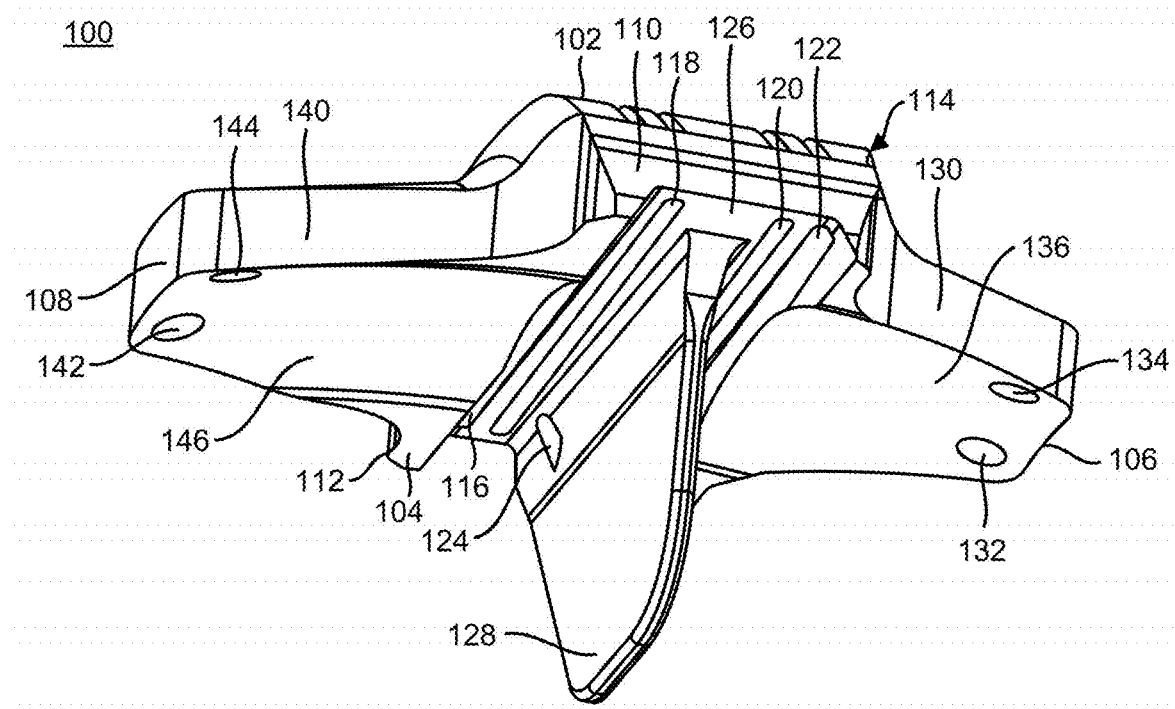
FIG. 2 is a bottom perspective view of the cut guide of FIG. 1, in accordance with an aspect of the present disclosure.
Figure 3:
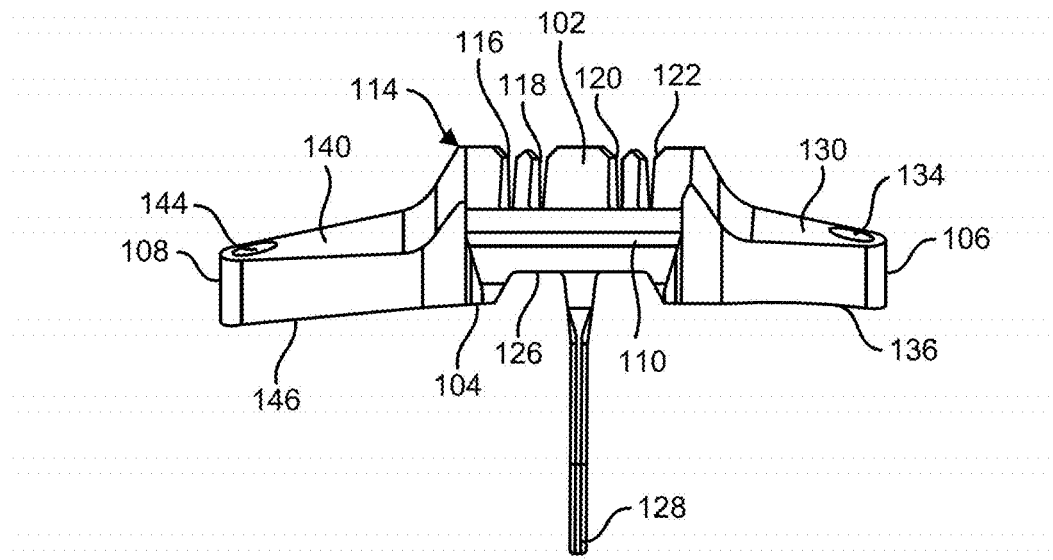
FIG. 3 is a side view of the cut guide of FIG. 1, in accordance with an aspect of the present disclosure.
Figure 8:
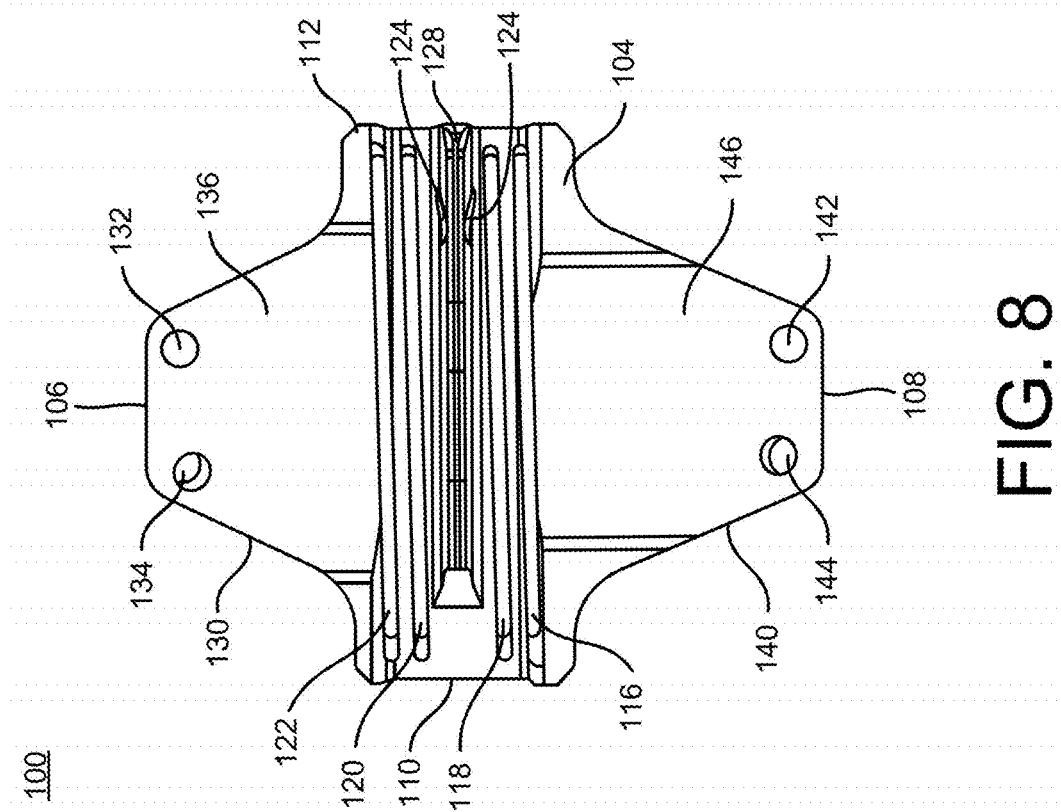
FIG. 8 is a bottom view of the cut guide of FIG. 1, in accordance with an aspect of the present disclosure.
Figure 7:
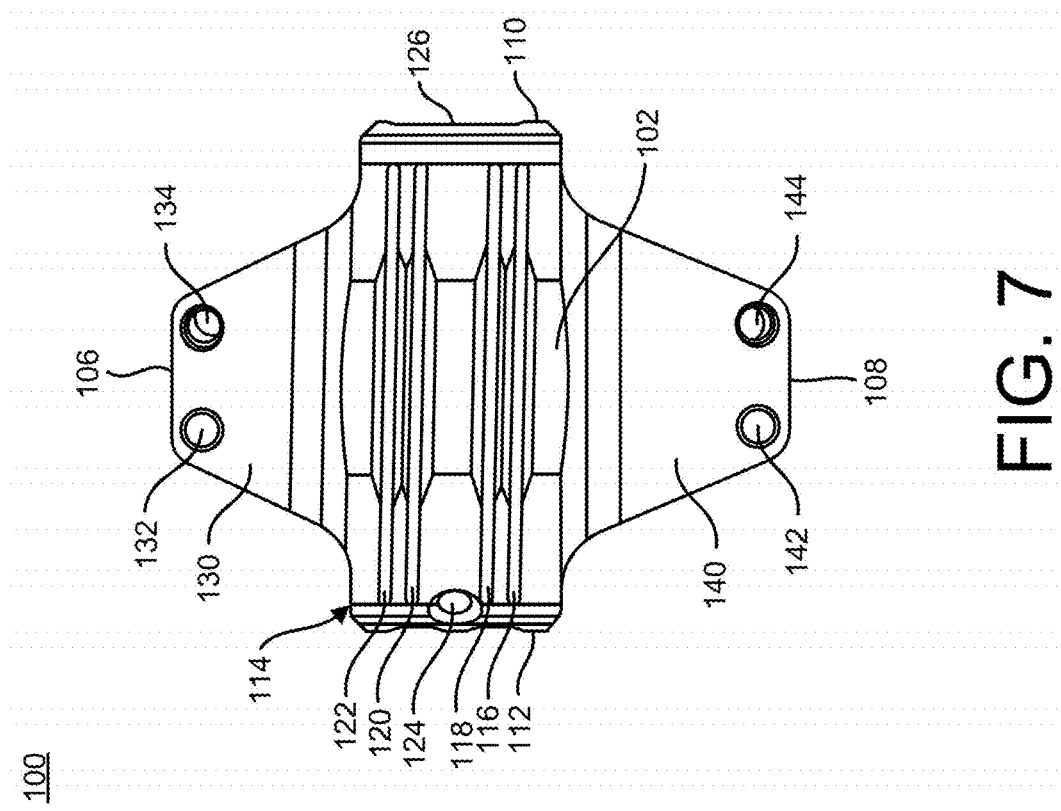
FIG. 7 is a top view of the cut guide of FIG. 1, in accordance with an aspect of the present disclosure.

The base portion 114 may also include a hole or dorsal hole 124, as shown in at least FIGS. 4, 7 and 8. The hole 124 is positioned between the second slot 118 and the third slot 120 near the second side 112 of the base portion 114. The hole 124 may extend, for example, into the base portion 114 from the top surface 102 of the cut guide 100 and to a point within the extension member 128. As shown in FIGS. 2 and 8, as the hole 124 extends into the extension member 128, the hole 124 forms a through hole in a proximal-distal direction through the extension member 128. The hole 124 may, for example, extend into the cut guide 100 parallel to the angled portion of the extension member 128, as shown in FIG. 2. The hole 124 may be sized and shaped or configured, for example, to receive a wire, alignment wire, k-wire, guide wire or the like to provide information on the position of the cut guide 100 in a joint. For example, the wire inserted into hole 124 should align approximately with the long axis of the tibia to provide the proper orientation of the cut guide 100 in the joint, which may be, for example, approximately 45° from dorsal and 45° from medial.

Referring now to FIGS. 1-4 and 8, the base portion 114 also includes a recessed region 126 positioned on the bottom surface 104. The recessed region 126 extends from the first side 110 to the second side 112 and into the base portion 114 a first distance from the bottom surface 104 toward the top surface 102. The extension member 128 is coupled to the recessed region 126 of the base portion 114 and extends away from the recessed region 126 of the base portion 114. In addition, the extension member 128 is positioned between the second slot 118 and the third slot 120 and also extends from the second side 112 toward the first side 110, as shown in FIGS. 5, 6 and 8. The extension member 128 may be shaped, for example, to fit within the joint space between two bones, such as, a first metatarsal and cuneiform, as well as to make contact with the adjoining articular joint surfaces. The extension member 128 may include a perpendicular portion near the first side 110 that extends perpendicularly away from the bottom surface 104. The perpendicular portion of the extension member 128 may be, for example, angled when the cut guide 100 is inserted into a patient's joint and the angle that the perpendicular portion is positioned at may correspond to the angle of the first tarsometatarsal joint medially. The extension member 128 may also include an angled portion extending from the second side 112 to the end of the extension member 128. The angled portion of the extension member 128 may, for example, allow for the extension member 128 to fit within a variety of anatomic presentations. The angled portion of the extension member 128 may, for example, be oriented laterally and should align with the long axis of the tibia, as well as fit within the joint to rest against the relatively straight surface of the adjacent bone, for example, the second metatarsal. When the angled portion of the extension member 128 is oriented against the second metatarsal, the cut guide 100 will be positioned at a 45° angle in the frontal plane.

As shown in FIGS. 1, 2, 7 and 8, the first or proximal arm 130 may extend away from an end of the base portion 114 and may be, for example, tapered from the base portion 114 to the first end 106 of the cut guide 100. The first arm 130 includes at least one opening 132, 134. In the depicted embodiment, the first arm 130 includes a first opening 132 and a second opening 134 positioned near the first end 106. The first opening 132 may be spaced apart from the second opening 134. The openings 132, 134 may extend from a top surface 102 to a bottom surface 104 of the cut guide 100. The openings 132, 134 may extend through the first arm 130, for example, parallel to the extension member 128, angled as they extend from the top surface 102 toward the bottom surface 104, or a combination of parallel and angled. In one embodiment, the first opening 132 may extend, for example, parallel to the extension member 128 and the second opening 134 may be, for example, angled with respect to the extension member 128 to permit the inserted wires, guide wires, k-wires and the like to cross above the cut guide 100 without intersecting. By positioning the openings 132, 134 such that inserted wires cross above the openings 132, 134 allows for a smaller surgical incision and less interaction or interference with other instruments during the procedure. The openings 132, 134 positioning the wires to cross also allows for the cut guide 100 to be, for example, suspended above and/or proximate to the bone surfaces being cut. The ability to suspend the cut guide 100 above the bone surfaces prevents the cut guide 100 from being titled because of varying patient anatomy and this avoids moving the slots 116, 118, 120, 122 which would affect the proposed cut angles. Alternative combinations of orientations of the openings 132, 134 are also contemplated, as would be understood by one of ordinary skill in the art from the above description. The first arm 130 may be shaped to provide a bone contacting surface 136 that corresponds to the shape of the bone that it will engage. The first arm 130 may be, for example, curved or arced as it extends between the first side 110 and the second side 112.

As shown in FIGS. 1, 2, 7 and 8, the second or distal arm 140 may extend away from an end of the base portion 114 and may be, for example, tapered from the base portion 114 to the second end 108 of the cut guide 100. The second arm 140 includes at least one opening 142, 144. In the depicted embodiment, the second arm 140 includes a third opening 142 and a fourth opening 144 positioned near the second end 108. The third opening 142 may be spaced apart from the fourth opening 144 and extend from a top surface 102 to a bottom surface 104 of the cut guide 100. The openings 142, 144 may extend through the second arm 140, for example, parallel to the extension member 128, angled as they extend from the top surface 102 toward the bottom surface 104, or a combination of parallel and angled. In one embodiment, the third opening 142 may extend, for example, parallel to the extension member 128 and the fourth opening 144 may be, for example, angled with respect to the extension member 128 to permit inserted wires, guide wires, k-wires, and the like to cross above the cut guide 100 without intersecting. By positioning the openings 142, 144 such that the inserted wires cross above the openings 142, 144 allows for a smaller surgical incision and less interaction or interference with other instruments during the procedure. The openings 142, 144 being positioned for the wires to cross, also allows for the cut guide 100 to be, for example, suspended above and/or mated with the bone surfaces being cut. Suspending the cut guide 100 above the bone surfaces prevents the cut guide 100 from being angled because of varying patient anatomy which results in not having to move the slots 116, 118, 120, 122 which would affect the proposed cut angles. In one embodiment, the openings 132, 142 may be, for example, positioned such that they are parallel to one another as they extend between the top and bottom surfaces 102, 104. By positioning the openings 132, 142 parallel to each other, the cut guide 100 may be, for example, removed from guide wires inserted through openings 132, 142 without removing the guide wires. In addition, parallel openings 132, 142 allow for the relative rotation between the two guide wires to be measured or calculated after the bones are cut using cut guide 100. Further, the openings 132, 142 may be, for example, spaced apart from the extension member 128 a standard or set distance to allow for interchangeability with alternative cut guides 200, 250, 300, 400, if a different or additional resection is needed. Alternative, combinations of orientations of the openings 142, 144 are also contemplated, as would be understood by one of ordinary skill in the art from the above description. The second arm 140 may be shaped to provide a bone contacting surface 146 that corresponds to the shape of the bone that it will engage. The second arm 140 may be, for example, curved or arced as it extends between the first side 110 and the second side 112. The second arm 140 may have, for example, a larger length and width than the first arm 130.

Figure 9:
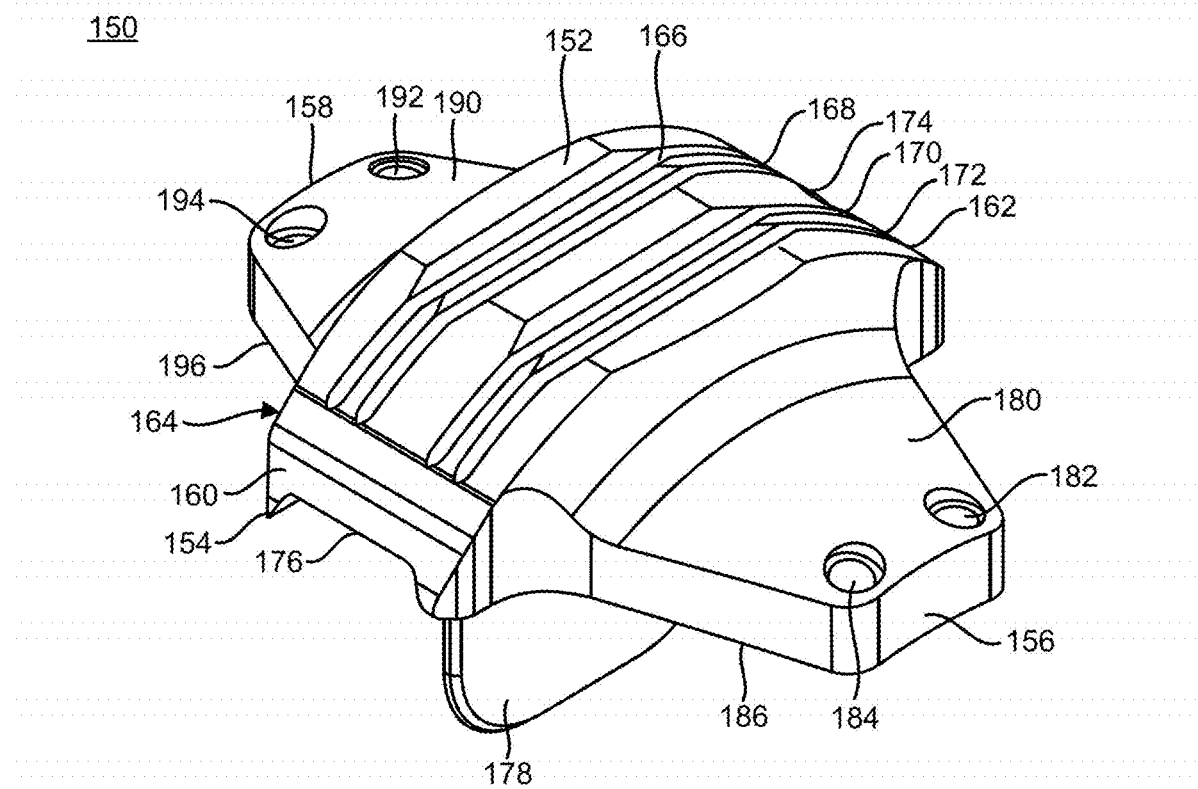
FIG. 9 is a top perspective view of another cut guide, in accordance with an aspect of the present disclosure.
Figure 10:
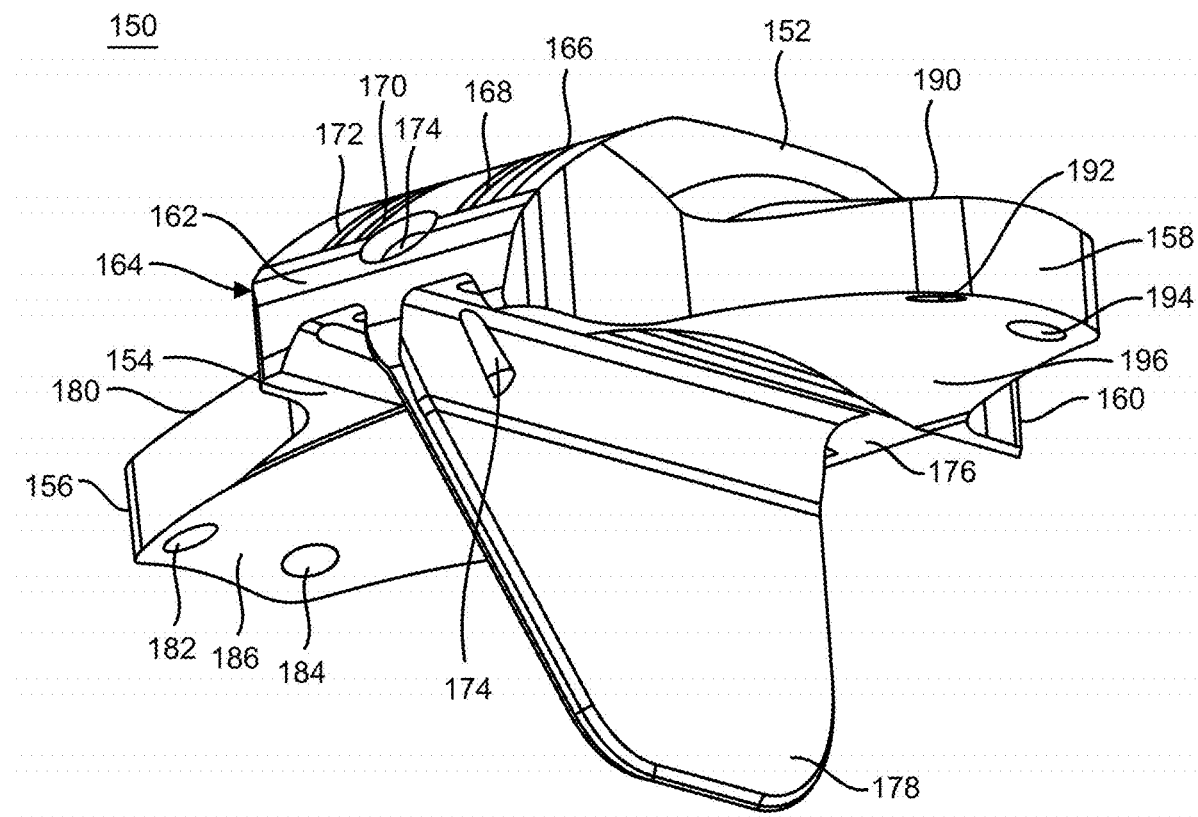
FIG. 10 is a bottom perspective view of the cut guide of FIG. 9, in accordance with an aspect of the present disclosure.

Referring now to FIGS. 9 and 10, another cut guide 150 is shown. The cut guide 150 is a mirror image of the cut guide 100 in a medial-lateral direction, which will not be described again in full detail for brevity purposes. For example, the hole 124 is positioned on a left side of the cut guide 100 when in an insertion position and the hole 174 is positioned on a right side of the cut guide 150 when in an insertion position. The cut guide 150 may be, for example, for a left foot. The cut guide 150 may include a top surface 152, a bottom surface 154, a first or proximal end 156, a second or distal end 158, a first or medial side 160, and a second or lateral side 162, which may be of the type described above with respect to the top surface 102, the bottom surface 104, the first or proximal end 106, the second or distal end 108, the first or medial side 110, and the second or lateral side 112, respectively. The cut guide 150 may also include a base portion 164 which may be the mirror image of the base portion 114, as described above. The slots 166, 168, 170, 172, the hole 174, and the recessed region 176 may be similar to the slots 116, 118, 120, 122, hole 124, and recessed region 126, as described in greater detail above. Further, the cut guide 150 may include a fin, paddle or extension member 178, a first or proximal arm 180, and a second or distal arm 190, which may be as described above with respect to the extension member 128, the first arm 130, and the second arm 140, respectively. The openings 182, 184 and the bone contacting surface 186 may be as described above with reference to openings 132, 134 and bone contacting surface 136 and the openings 192, 194 and the bone contacting surface 196 may be as described above with reference to openings 142, 144 and the bone contacting surface 146, which will not be described again here for brevity purposes.

Another cut guide 200 is shown in FIGS. 11-18. The cut guide 200 includes a top surface 202, a bottom surface 204, a first or proximal end 206, a second or distal end 208, a first or medial side 210, and a second or lateral side 212. The top surface 202 may be, for example, wider than the top surface 102 of cut guide 100 providing for larger angular corrections. The cut guide 200 also includes a base portion 214, a paddle, fin or extension member 228 extending away from the bottom surface 204 of the base portion 214, a first or proximal arm 230 extending away from the base portion 214 on the first end 206, and a second or distal arm 240 extending away from the base portion 214 on the second end 208. The cut guide 200 may be, for example, a right foot cut guide. A mirror image of the cut guide 200 for, for example, a left foot is also contemplated. The cut guide 200 may provide, for example, for transverse plane correction angles of approximately 16°, 18° and 20°, although alternative angles of correction are also contemplated.

Figure 11:
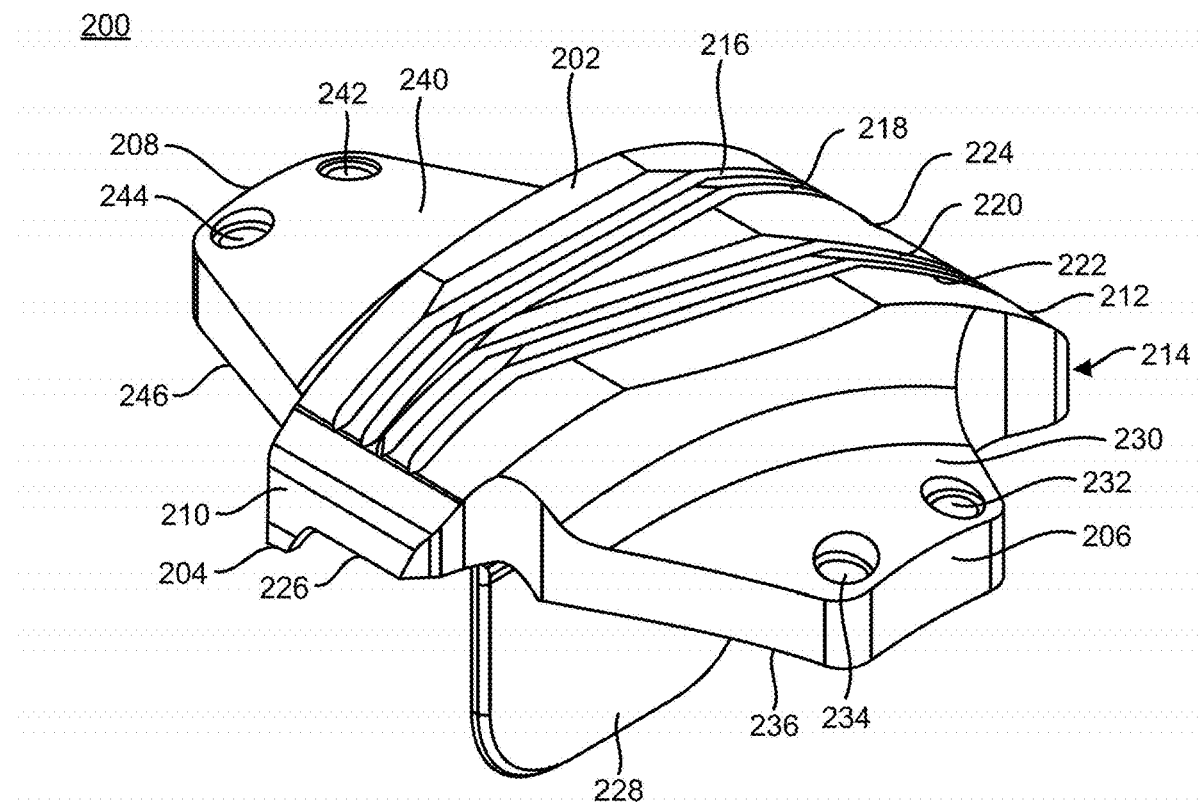
FIG. 11 is a top perspective view of another cut guide, in accordance with an aspect of the present disclosure.
Figure 15:
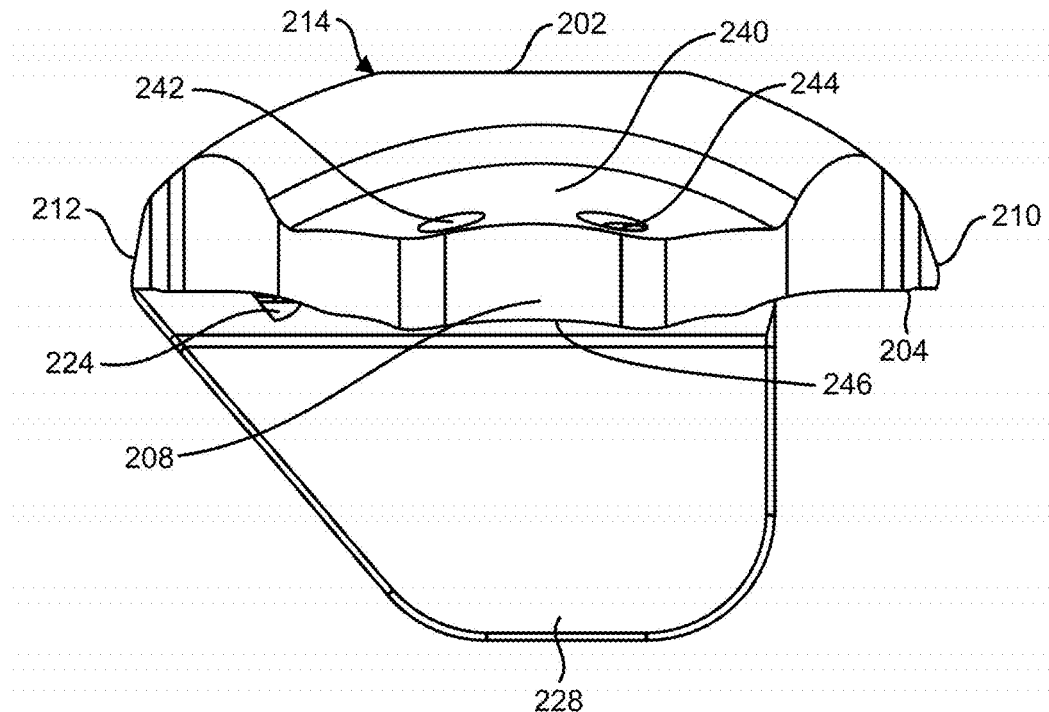
FIG. 15 is an end view of the cut guide of FIG. 11, in accordance with an aspect of the present disclosure.
Figure 16:
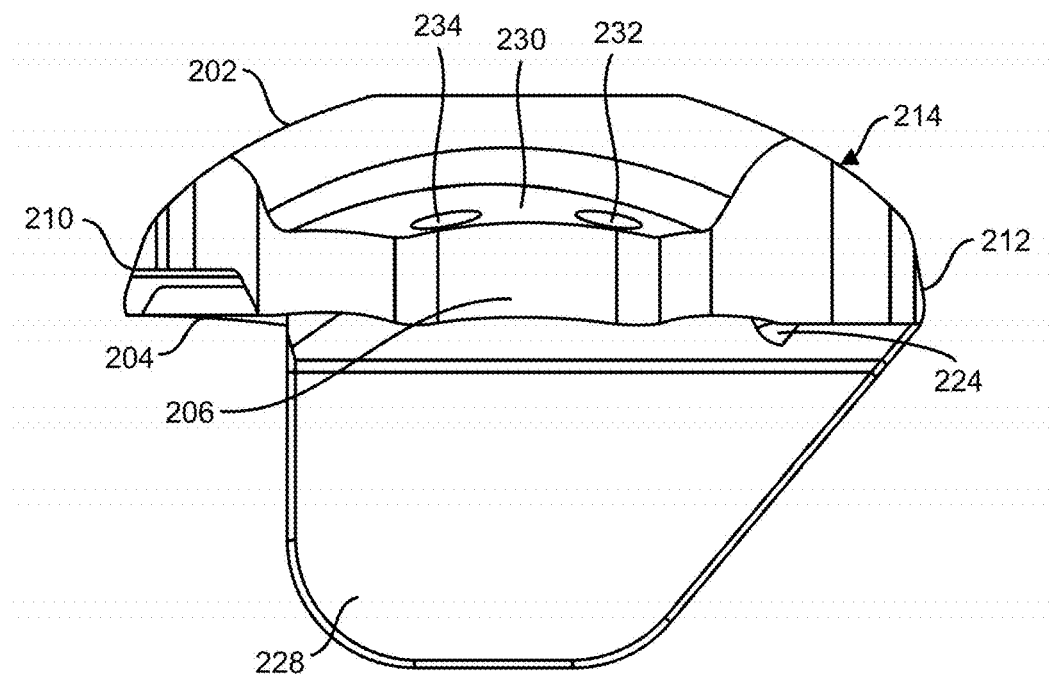
FIG. 16 is another end view of the cut guide of FIG. 11, in accordance with an aspect of the present disclosure.

As shown in FIGS. 11, 15 and 16, the top surface 202 of the base portion 214 may be, for example, curved or arced between the first side 210 and the second side 212. In one embodiment, the top surface 202 of the base portion 214 may include, for example, a flat or planar portion positioned between a first curvature or arc extending from the first side 210 to the flat portion and a second curvature or arc extending from a second side 212 to the flat portion. The end of the base portion 214 near the first end 206 of the cut guide 200 may be, for example, angled from the second side 212 to the first side 210, as shown in FIG. 17. The end of the base portion 214 near the second end 208 of the cut guide 200 may extend, for example, perpendicularly between the first side 210 and the second side 212, as shown in FIG. 17.

The base portion 214 also includes at least one slot 216, 218, 220, 222, as shown in FIGS. 11-14, 17 and 18. In the depicted embodiment, the base portion 214 includes a first slot 216 adjacent to a second slot 218 and a third slot 220 adjacent to a fourth slot 222. The first and second slots 216, 218 are positioned on the base portion 214 near the second end 208 of the cut guide 200 and the third and fourth slots 220, 222 are positioned on the base portion 214 near the first end 206 of the cut guide 200. The slots 216, 218, 220, 222 may extend, for example, linearly or angled through the base portion 214 from the top surface 202 to the bottom surface 204 of the cut guide 200. The slots 216, 218, 220, 222 may be, for example, angled approximately 1° to 4° and more specifically, approximately 2°, as the slots 216, 218, 220, 222 extend between the top and bottom surfaces 202, 204. It is also contemplated that some of slots 216, 218, 220, 222 may be angled and other slots 216, 218, 220, 222 may be linear as they extend through the base portion 214 from the top surface 202 to the bottom surface 204.

In addition, the slots 216, 218 may be oriented, for example, relatively perpendicular to the first side 210 and the second side 212 as the slots 216, 218 extend from the first side 210 to the second side 212, as shown in FIGS. 11-14, 17 and 18. The slots 220, 222 may be, for example, angled as the slots 220, 222 extend between the second side 212 and the first side 210. The slots 220, 222 may also be, for example, angled toward the slots 216, 218, as the slots 220, 222 extend from the second side 212 to the first side 210. The slots 220, 222 may also be positioned to extend parallel to the end of the base portion 214 near the second end 208 of the cut guide 200. The slots 220, 222 may be, for example, angled between approximately 2° and 30°, and more specifically between approximately 8° and 22° as the slots 220, 222 extend from the second side 212 to the first side 210 providing for an angulation correction of 8° to 22° in the transverse plane. The slots 216, 218, 220, 222 may be configured or sized and shaped to receive a saw blade and may have a width of, for example, approximately 0.58 mm to 0.92 mm. The slots 216, 218, 220, 222 may be positioned, for example, to allow for removal of the articular cartilage layer at the ends of the two bones. To prevent resecting more tissue than absolutely necessary, the slots 216, 218, 220, 222 may be positioned, for example, such that the medial portion of the slots 216, 218, 220, 222 are aligned with the intersection of the cartilage and bone.

Figure 12:
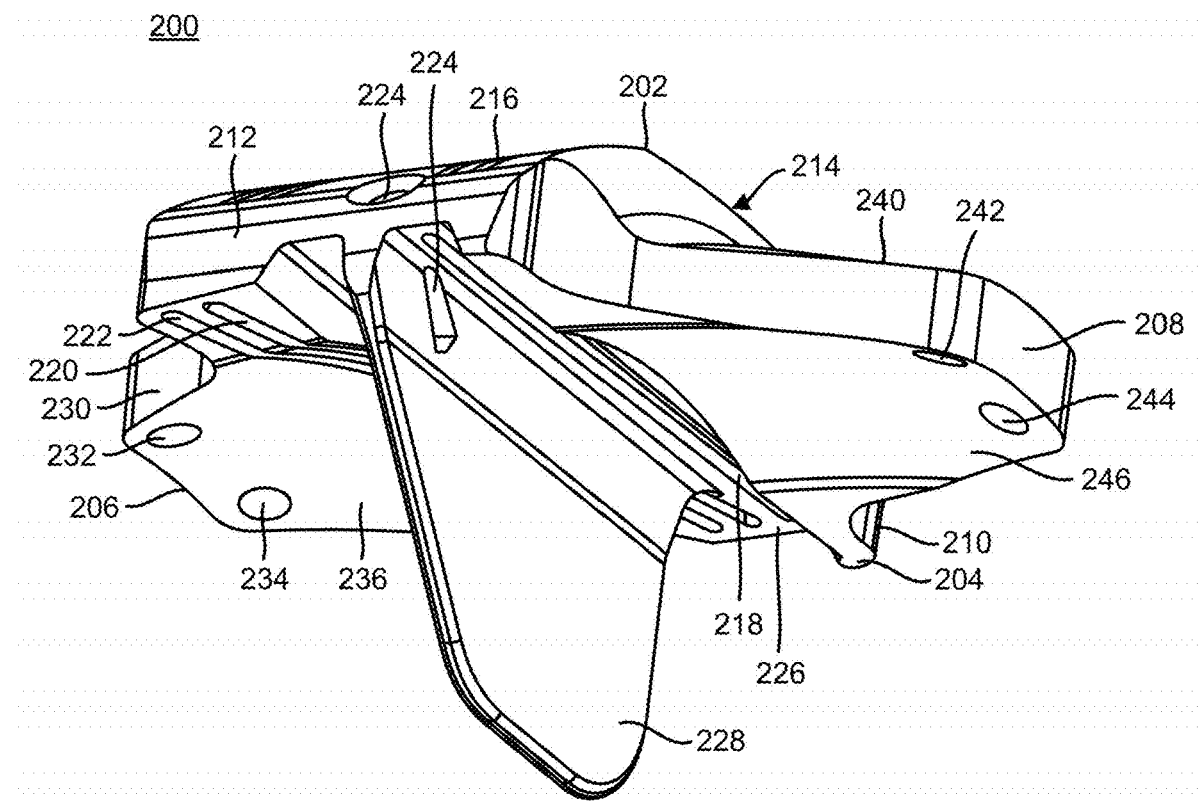
FIG. 12 is a bottom perspective view of the cut guide of FIG. 11, in accordance with an aspect of the present disclosure.
Figure 13:
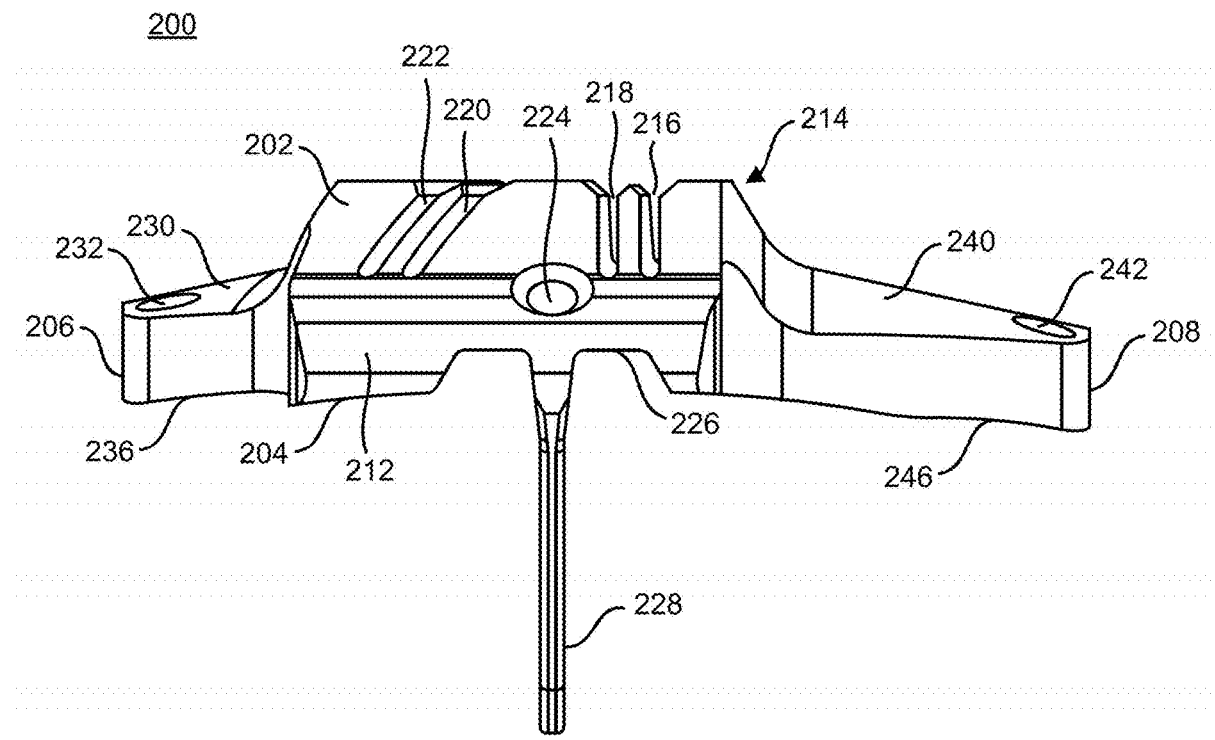
FIG. 13 is a side view of the cut guide of FIG. 11, in accordance with an aspect of the present disclosure.
Figure 14:
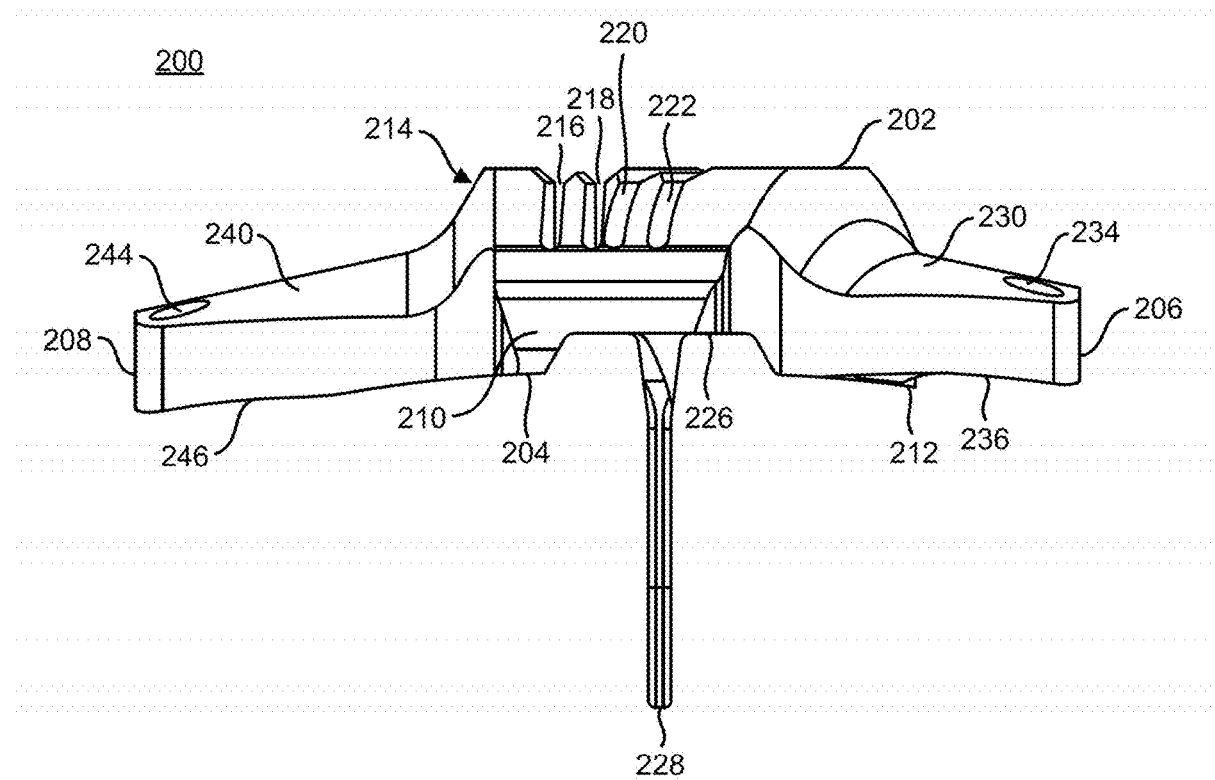
FIG. 14 is another side view of the cut guide of FIG. 11, in accordance with an aspect of the present disclosure.

The base portion 214 may also include a hole or dorsal hole 224, as shown in at least FIGS. 12, 13, 17 and 18. The hole 224 is positioned between the second slot 218 and the third slot 220 near the second side 212 of the base portion 214. The hole 224 may extend, for example, into the base portion 214 from the top surface 202 of the cut guide 200 and to a point within the extension member 228. As shown in FIGS. 12, 15, 16 and 18, as the hole 224 extends into the extension member 228, the hole 224 forms an opening in a proximal-distal direction through the extension member 228. The hole 224 may, for example, extend into the cut guide 200 parallel to the angled portion of the extension member 228, as shown in FIG. 12. The hole 224 may be sized and shaped or configured, for example, to receive a wire, alignment wire, k-wire, guide wire or the like to provide information on the position of the cut guide 200 in a joint. For example, a wire inserted into hole 224 should align approximately with the long axis of the patient's tibia to provide the proper orientation of the cut guide 200 in the joint, which may be, for example, approximately 45° from dorsal and 45° from medial in the frontal plane.

Referring now to FIGS. 11-14 and 18, the base portion 214 also includes a recessed region 226 positioned on the bottom surface 204. The recessed region 226 extends from the first side 210 to the second side 212 and into the base portion 214 from the bottom surface 204 toward the top surface 202. The recessed region 226 extends to engage the bone contacting surface 236 of the first arm 230 at the first side 210 of the base portion 214. The extension member 228 is coupled to the recessed region 226 of the base portion 214 and extends away from the recessed region 226 of the base portion 214. In addition, the extension member 228 is positioned between the second slot 218 and the third slot 220. The extension member 228 also extends from the second side 212 toward the first side 210, as shown in FIGS. 12, 15, 16 and 18. The extension member 228 may include a perpendicular portion near the first side 210 that extends perpendicularly away from the bottom surface 204. The perpendicular portion of the extension member 128 may be, for example, angled when the cut guide 200 is inserted into a patient's joint and the angle that the perpendicular portion is positioned at may correspond to the angle of the first tarso-metatarsal joint medially. The extension member 228 may also include an angled portion extending from the second side 212 to the end of the extension member 228. The extension member 228 may be shaped, for example, to fit within the joint space between two bones, such as, a first metatarsal and cuneiform, as well as to mate with the articular joints. The angled portion of the extension member 228 may, for example, be oriented laterally and should align with the long axis of the tibia, as well as fit within the joint to rest against the relatively straight surface of the adjacent bone, for example, the second metatarsal. When the angled portion of the extension member 228 is oriented against the second metatarsal, the cut guide 200 will be positioned at a 45° angle in the frontal plane.

As shown in FIGS. 11, 12, 17 and 18, the first or proximal arm 230 may extend away from an end of the base portion 214 and may be, for example, tapered from the base portion 214 to the first end 206 of the cut guide 200. The side of the first arm 230 on the first side 210 of the cut guide 200 may be, for example, longer than the side of the first arm 230 on the second side 212 of the cut guide 200. The first arm 230 includes at least one opening 232, 234. In the depicted embodiment, the first arm 230 includes a first opening 232 and a second opening 234 positioned near the first end 206. The first opening 232 may be spaced apart from the second opening 234. The openings 232, 234 may extend from a top surface 202 to a bottom surface 204 of the cut guide 200. The openings 232, 234 may extend through the first arm 230, for example, parallel to the extension member 228, angled as they extend from the top surface 202 toward the bottom surface 204, or a combination of parallel and angled. In one embodiment, the first opening 232 may extend, for example, parallel to the extension member 228 and the second opening 234 may be, for example, angled with respect to the extension member 228. Alternative combinations of the orientations of the openings 232, 234 are also contemplated, as would be understood by one of ordinary skill in the art from the above description. The first arm 230 may be shaped to provide a bone contacting surface 236 that corresponds to the shape or surface of the bone that it will engage. The first arm 230 may be, for example, curved or arced as it extends between the first side 210 and the second side 212 of the cut guide 200.

As shown in FIGS. 11, 12, 17 and 18, the second or distal arm 240 may extend away from an end of the base portion 214 and may be, for example, tapered from the base portion 214 to the second end 208 of the cut guide 200. The second arm 240 also includes at least one opening 242, 244. In the depicted embodiment, the second arm 240 includes a third opening 242 and a fourth opening 244 positioned near the second end 208. The third opening 242 may be spaced apart from the fourth opening 244. The openings 242, 244 may extend from a top surface 202 to a bottom surface 204 of the cut guide 200. The openings 242, 244 may extend through the second arm 240, for example, parallel to the extension member 228, angled as they pass from the top surface 202 to the bottom surface 204, or a combination of parallel and angled. In one embodiment, the third opening 242 may extend, for example, parallel to the extension member 228 and the fourth opening 244 may be, for example, angled with respect to the extension member 228. Alternative combinations of the openings 242, 244 orientations are also contemplated, as would be understood by one of ordinary skill in the art from the above description. In one embodiment, the holes 232, 242 may be, for example, positioned such that they are parallel to one another as they extend between the top and bottom surfaces 202, 204. By positioning the holes 232, 242 parallel to each other, the cut guide 200 may be, for example, removed from guide wires inserted through holes 232, 242 without removing the guide wires. In addition, parallel holes 232, 242 allow for the relative rotation between the two guide wires to be measured or calculated after the bones are cut using cut guide 200. Further, the holes 232, 242 may be, for example, spaced apart from the extension member 228 a standard or set distance to allow for interchangeability with alternative cut guides 100, 250, 300, 400, if a different or additional resection is needed. The second arm 240 may be shaped to provide a bone contacting surface 246 that corresponds to the surface or shape of the bone that it will engage. The second arm 240 may be, for example, curved or arced as it extends between the first side 210 and the second side 212. The second arm 240 may have, for example, a larger length and width than the first arm 230.

The openings 232, 234, 242, 244 may be positioned such that wires inserted into the first and second openings 232, 234 cross above the cut guide 200 and wires inserted into the third and fourth openings 242, 244 cross above the cut guide 200. By positioning the openings 232, 234 and openings 242, 244 such that inserted wires cross above the openings 232, 234 and openings 242, 244, respectively, the surgeon may make a smaller surgical incision and reduce the interaction or interference with other instruments during the procedure. The openings 232, 234, 242, 244 being positioned to allow the wires to cross also allows for the cut guide 200 to be, for example, suspended above and/or in contact with the bone surfaces being cut. Suspending the cut guide 200 above the bone surfaces prevents the cut guide 200 from being angled or tilted on the irregular bone surface and avoids moving the slots 216, 218, 220, 222, which would affect the proposed cut angles.

Referring now to FIGS. 19-26, yet another cut guide 250 is shown. The cut guide 250 includes a top surface 252, a bottom surface 254, a first or proximal end 256, a second or distal end 258, a first or medial side 260, and a second or lateral side 262. The top surface 252 may be, for example, narrower than the top surface 202 of cut guide 200 to provide for smaller angular corrections. The cut guide 250 also includes a base portion 264, a paddle, fin or extension member 278 extending away from the bottom surface 254 of the base portion 264, a first or proximal arm 280 extending away from the base portion 264 on a first end 256, and a second or distal arm 290 extending away from the base portion 264 on a second end 258. The cut guide 250 may be, for example, a right foot cut guide. A mirror image of the cut guide 250 for, for example, a left foot is also contemplated. The cut guide 250 may provide, for example, for transverse plane correction angles of approximately 2°, 4°, 6°, 8°, 10°, 12° and 14°, although alternative angles are also contemplated.

Figure 19:
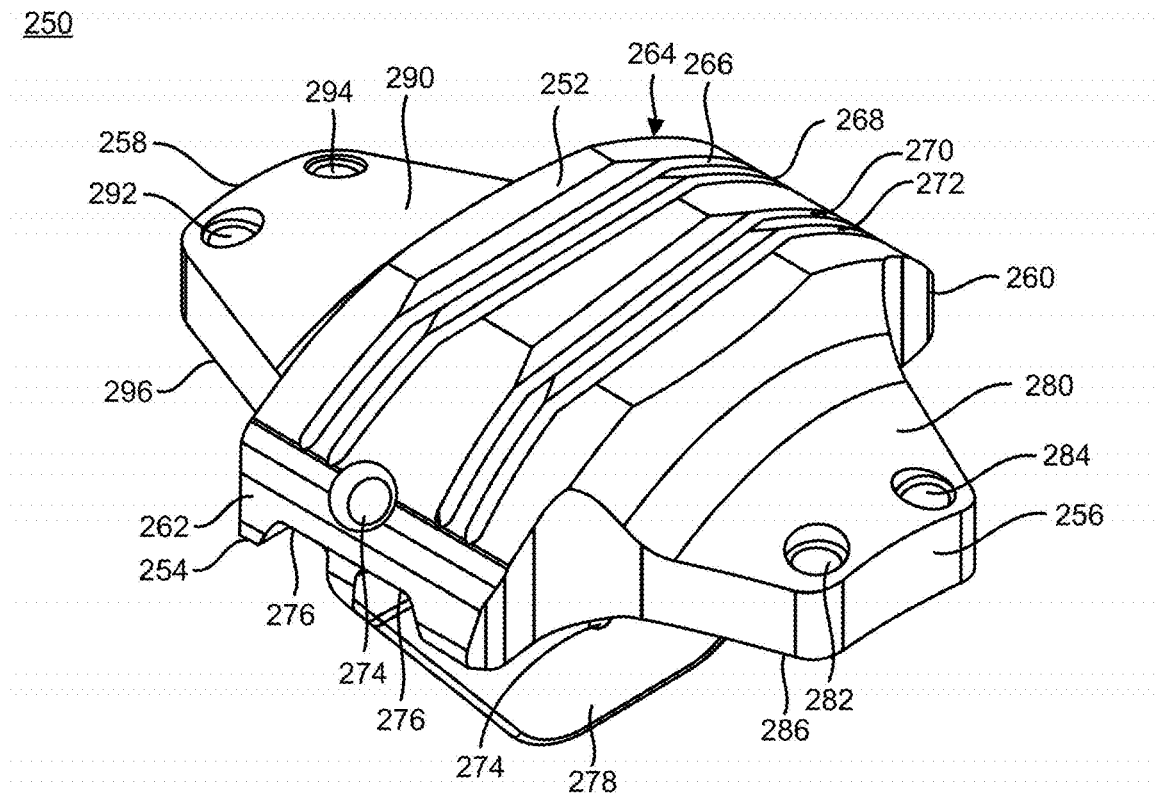
FIG. 19 is a top perspective view of another cut guide, in accordance with an aspect of the present disclosure.
Figure 20:
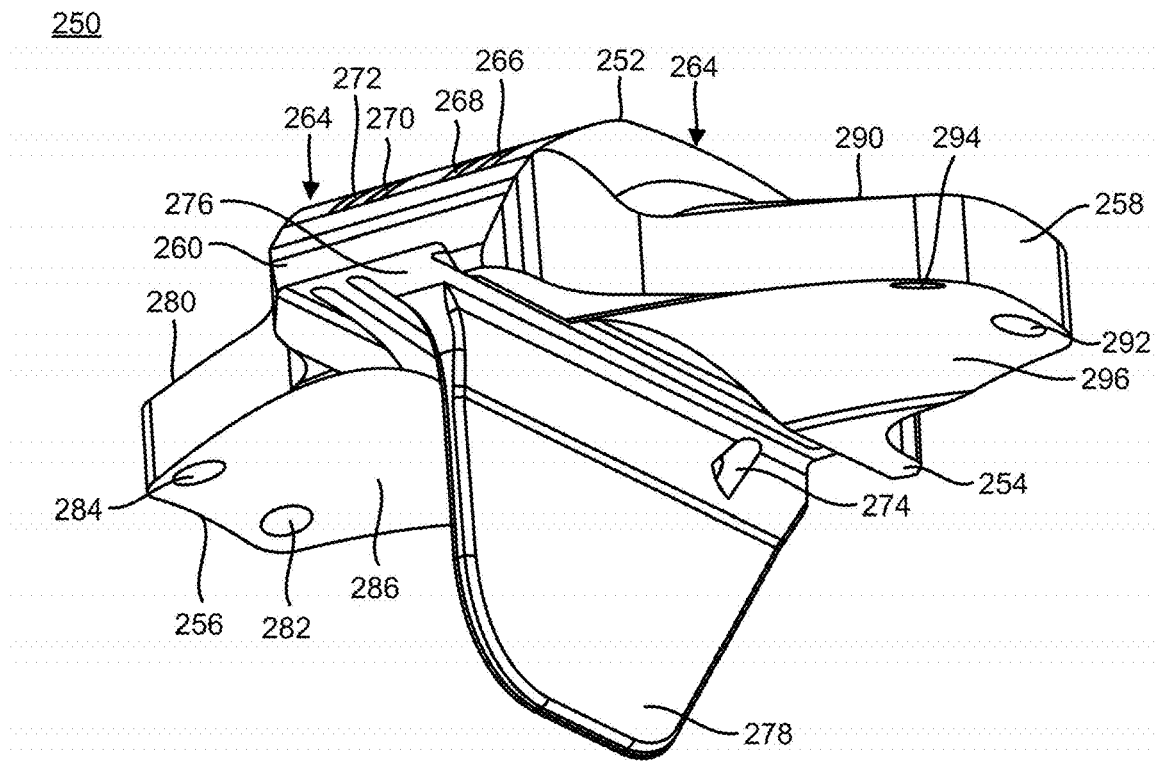
FIG. 20 is a bottom perspective view of the cut guide of FIG. 19, in accordance with an aspect of the present disclosure.
Figure 21:
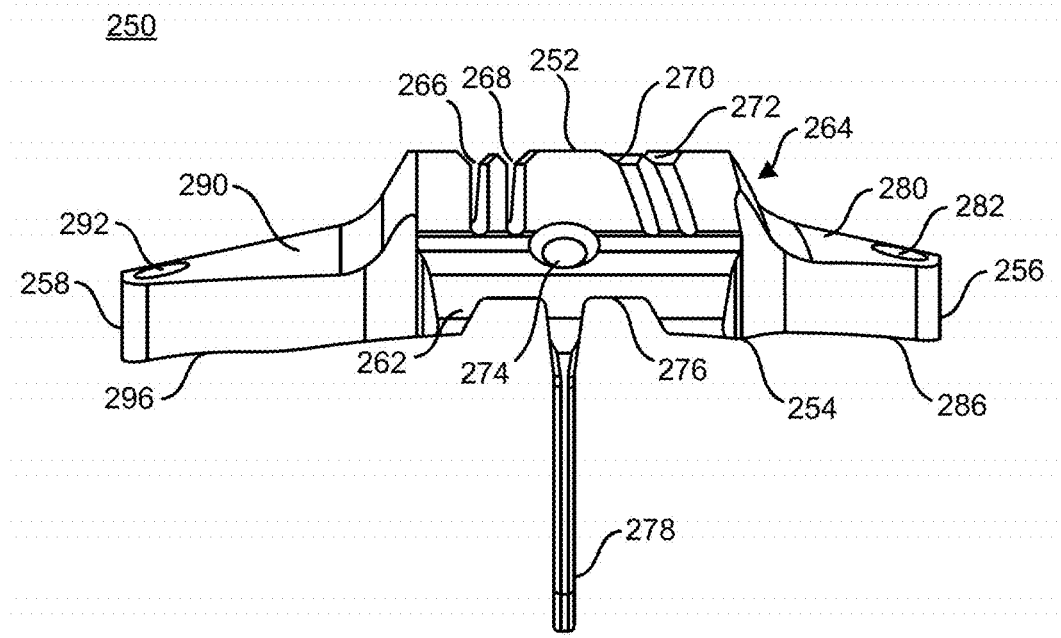
FIG. 21 is a side view of the cut guide of FIG. 19, in accordance with an aspect of the present disclosure.
Figure 22:
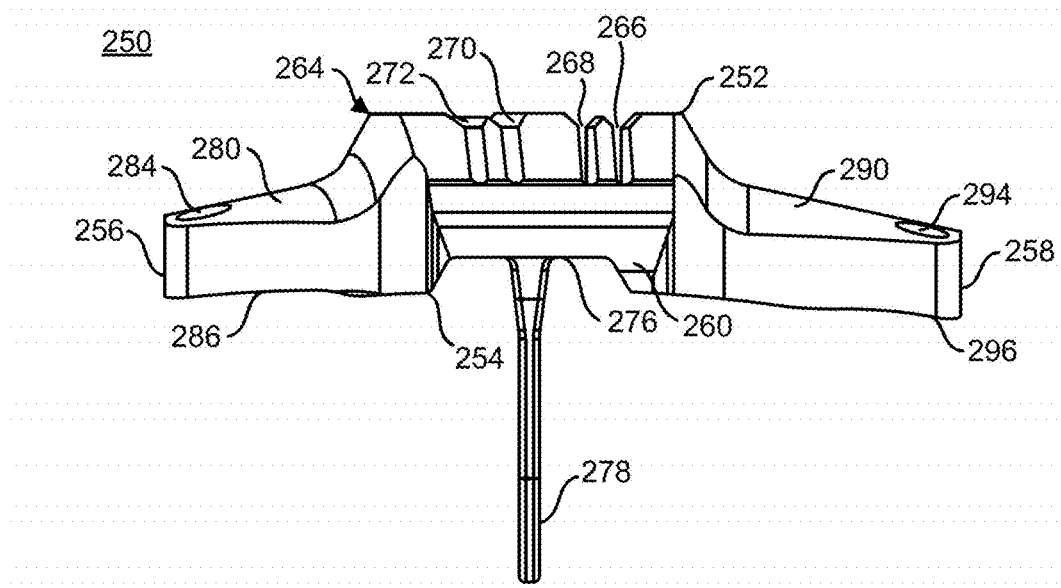
FIG. 22 is another side view of the cut guide of FIG. 19, in accordance with an aspect of the present disclosure.
Figure 23:
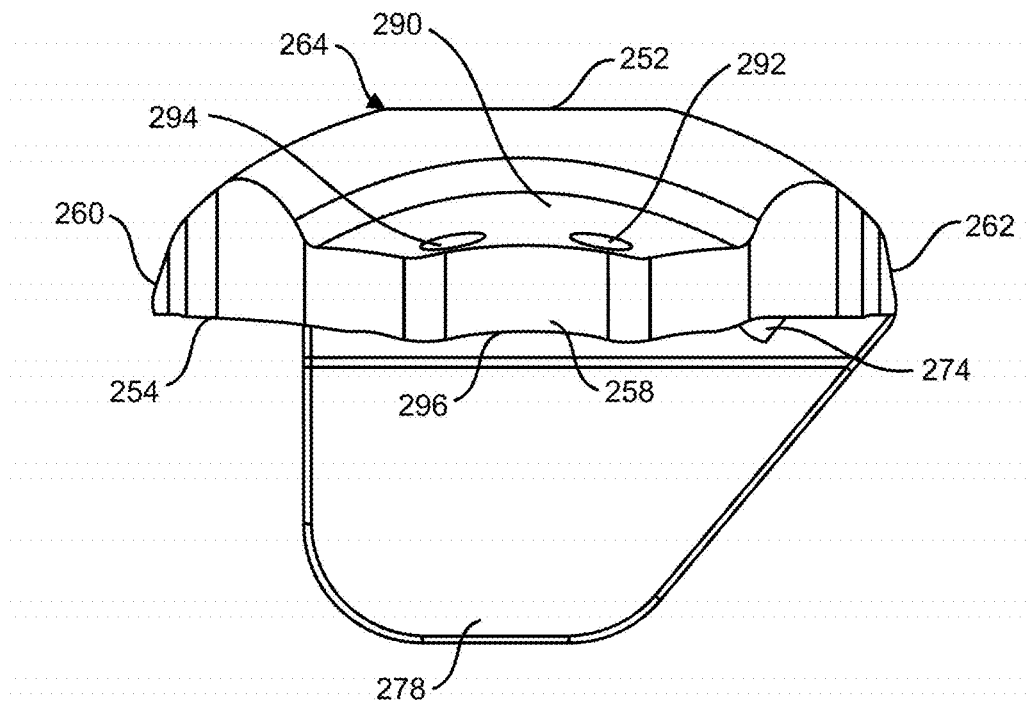
FIG. 23 is an end view of the cut guide of FIG. 19, in accordance with an aspect of the present disclosure.
Figure 24:
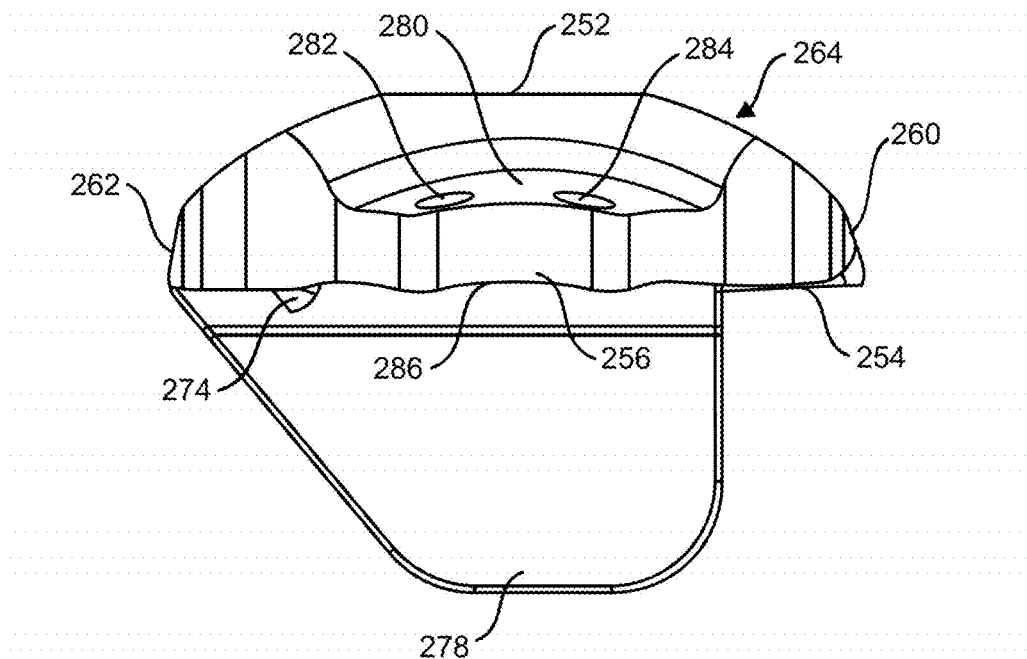
FIG. 24 is another end view of the cut guide of FIG. 19, in accordance with an aspect of the present disclosure.
Figure 25:
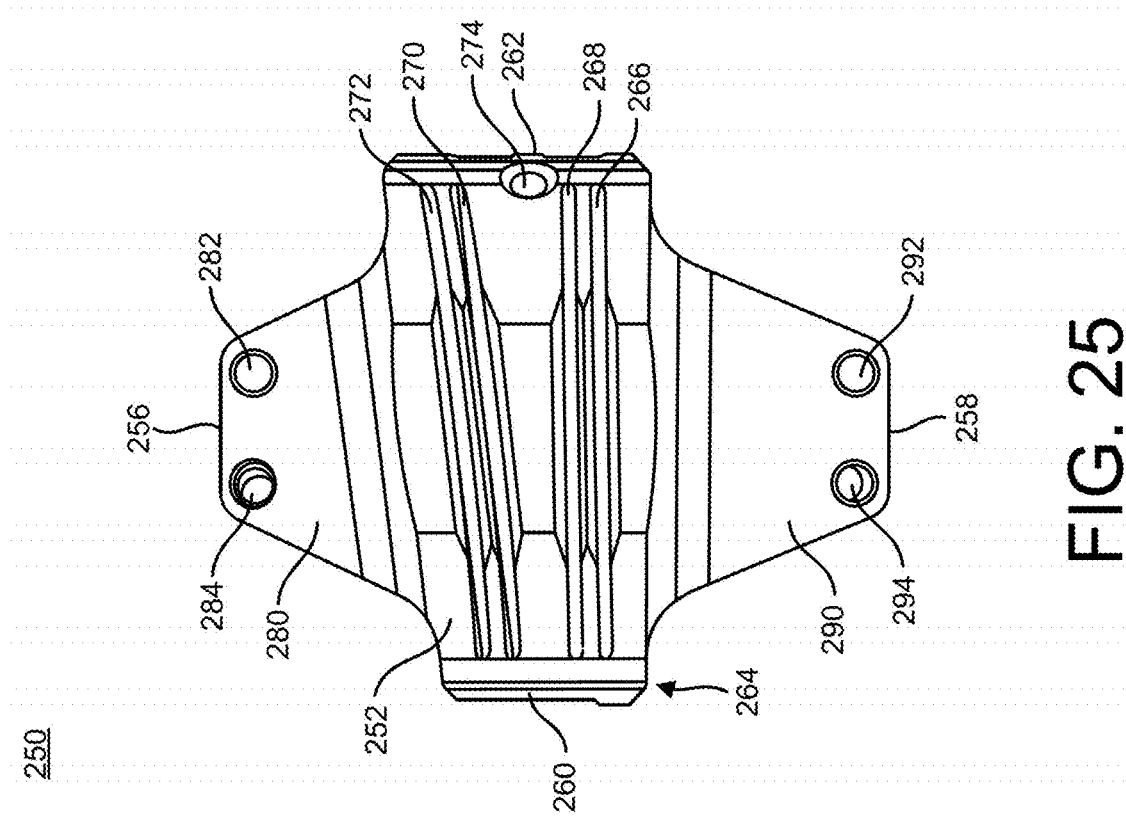
FIG. 25 is a top view of the cut guide of FIG. 19, in accordance with an aspect of the present disclosure.

As shown in FIGS. 19, 23 and 24, the top surface 252 of the base portion 264 may be, for example, curved or arced between the first side 260 and the second side 262. The top surface 252 of the base portion 264 may include, for example, a flat or planar portion positioned between a first curvature or arc extending from the first side 260 to the flat portion and a second curvature or arc extending from the second side 262 to the flat portion, as shown in FIGS. 23 and 24. The end of the base portion 264 near the first end 256 of the cut guide 250 may be, for example, angled from the second side 262 to the first side 260, as shown in FIG. 25. The end of the base portion 264 near the second end 258 of the cut guide 250 may extend, for example, perpendicularly between the first side 260 and the second side 262, as shown in FIG. 25.

The base portion 264 also includes at least one slot 266, 268, 270, 272, as shown in FIGS. 19-22, 25 and 26. In the depicted embodiment, the base portion 264 includes a first slot 266 adjacent to a second slot 268 and a third slot 270 adjacent to a fourth slot 272. The first and second slots 266, 268 are positioned on the base portion 264 near the second end 258 of the cut guide 250 and the third and fourth slots 270, 272 are positioned on the base portion 264 near the first end 256 of the cut guide 250. The slots 266, 268, 270, 272 may extend, for example, linearly through the base portion 264 from the top surface 252 to the bottom surface 254. The slots 266, 268, 270, 272 may also be, for example, angled as the slots 266, 268, 270, 272 extend from the top surface 252 to the bottom surface 254. The slots 266, 268, 270, 272 may be angled, for example, approximately 1° to 4° an more specifically, approximately 2°, as the slots 266, 268, 270, 272 extend from the top surface 252 to the bottom surface 254. It is also contemplated that some of the slots 256, 258, 230, 232 may be angled and other slots 256, 258, 260, 262 may be linear as they extend through the base portion 254 from the top surface 252 to the bottom surface 254.

The slots 266, 268 may also extend, for example, relatively perpendicular to the first side 260 and the second side 262 as the slots 266, 268 extend from the first side 260 to the second side 262, as shown in FIGS. 19-22, 25 and 26. The slots 270, 272 may be, for example, angled as the slots 270, 272 extend between the second side 262 and the first side 260. The slots 270, 272 may also be, for example, angled toward the slots 266, 268 as the slots 270, 272 extend from the second side 262 to the first side 260. The slots 270, 272 may be positioned to extend parallel to the end of the base portion 264 near the first end 256 of the cut guide 250. The slots 270, 272 may be, for example, angled at approximately 10°, 12°, 14°, and 16° as they extend between the first side 260 and the second side 262 providing for angulation corrections of 8°, 10°, 12°, and 14°, respectively. The slots 266, 268, 270, 272 may be configured or sized and shaped to receive a saw blade and may have a width of, for example, approximately 0.58 mm to 0.92 mm. The slots 266, 268, 270, 272 may be positioned, for example, to allow for removal of the articular cartilage. To prevent resecting more tissue than absolutely necessary, the slots 266, 268, 270, 272 may be positioned, for example, such that the medial portion of the slots 266, 268, 270, 272 are aligned with the intersection of the cartilage and bone or the cartilage-bone line.

Figure 26:
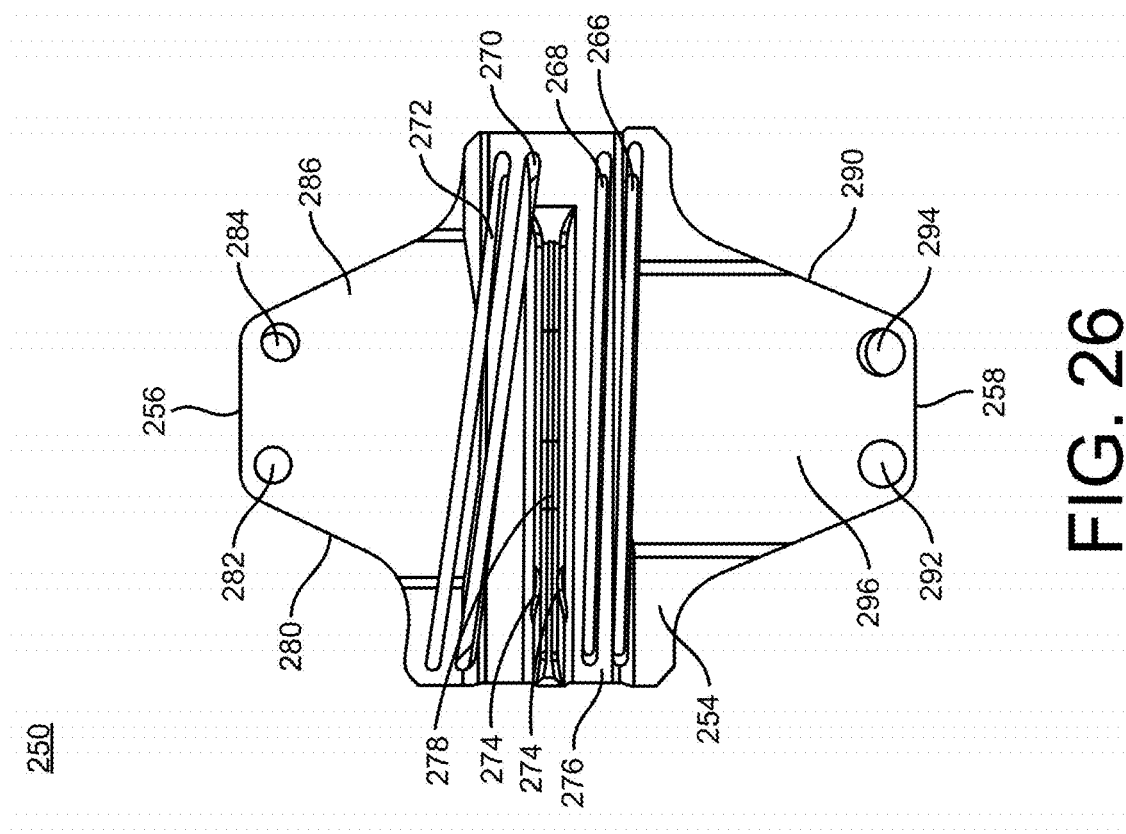
FIG. 26 is a bottom view of the cut guide of FIG. 19, in accordance with an aspect of the present disclosure.

The base portion 264 may also include a hole or dorsal hole 274, as shown in at least FIGS. 19-21 and 23-26. The hole 274 is positioned between the second slot 268 and the third slot 270 near the second side 262 of the base portion 264. The hole 274 may extend, for example, through the base portion 264 from the top surface 252 of the cut guide 250 and to an intersection point within the extension member 278. As shown in FIGS. 23, 24 and 26, as the hole 274 extends into the extension member 278, the hole 274 forms an opening in a proximal-distal direction through the extension member 278. The hole 274 may, for example, extend into the cut guide 250 parallel to the angled portion of the extension member 278, as shown in FIGS. 23 and 24. The hole 274 may also be sized and shaped or configured, for example, to receive a wire, alignment wire, k-wire, guide wire or the like to provide information on the position of the cut guide 250 in a joint. For example, the wire inserted into hole 274 should align approximately with the long axis of the tibia to provide the proper orientation of the cut guide 250 relative to the joint, which may be, for example, approximately 45° from dorsal and 45° from medial in the frontal plane.

Referring now to FIGS. 19-22 and 26, the base portion 264 may also include a recessed region 276 positioned on the bottom surface 254. The recessed region 276 extends from the first side 260 to the second side 262 and into the base portion 264 from the bottom surface 254 toward the top surface 252. The extension member 278 is coupled to the recessed region 276 of the base portion 264 and extends away from the recessed region 276. In addition, the extension member 278 is positioned between the second slot 268 and the third slot 270 and extends from the second side 262 toward the first side 260, as shown in FIGS. 20, 23, 24 and 26. The extension member 278 may include a perpendicular portion near the first side 260 that extends perpendicularly away from the bottom surface 254. The perpendicular portion of the extension member 278 may be, for example, angled when the cut guide 250 is inserted into a patient's joint and the angle that the perpendicular portion is positioned at may correspond to the angle of the first tarsometatarsal joint medially. The extension member 278 may also include an angled portion extending from the second side 262 to the end of the extension member 278. The extension member 278 may be shaped, for example, to fit within the joint space between two adjacent bones, such as, a first metatarsal and cuneiform, as well as to make contact with the two side of an articular joint. The angled portion of the extension member 278 may, for example, be oriented laterally and should align with the long axis of the tibia, as well as fit within the joint to rest against the relatively straight surface of the adjacent bone, for example, the second metatarsal. When the angled portion of the extension member 228 is oriented against the second metatarsal, the cut guide 250 will be positioned at a 45° angle in the frontal plane.

As shown in FIGS. 19, 20, 25 and 26, the first or proximal arm 280 may extend away from an end of the base portion 264 and may be, for example, tapered from the base portion 264 to the first end 256 of the cut guide 250. The side of the first arm 280 on the first side 260 of the cut guide 250 may be, for example, longer than the side of the first arm 280 on the second side 262 of the cut guide 250. The first arm 280 includes at least one opening 282, 284. In the depicted embodiment, the first arm 280 includes a first opening 282 and a second opening 284 positioned near the first end 256. The first opening 282 may be spaced apart from the second opening 284. The openings 282, 284 may extend from a top surface 252 to a bottom surface 254 of the cut guide 250. The openings 282, 284 may extend through the first arm 280, for example, parallel to the extension member 278, angled as they extend from the top surface 252 toward the bottom surface 254, or a combination of parallel and angled orientations. In one embodiment, the first opening 282 may extend, for example, parallel to the extension member 278 and the second opening 284 may be, for example, angled with respect to the extension member 278. Alternative, combinations of orientations of the openings 282, 284 are also contemplated, as would be understood by one of ordinary skill in the art from the above description. The first arm 280 may be shaped to provide a bone contacting surface 236 that corresponds to the shape of the bone that it will engage. The first arm 280 may be, for example, curved or arced as it extends between the first side 260 and the second side 262 of the cut guide 250.

As shown in FIGS. 19, 20, 25 and 26, the second or distal arm 290 may extend away from an end of the base portion 264 and may be, for example, tapered from the base portion 264 to the second end 258 of the cut guide 250. The second arm 290 includes at least one opening 292, 294. In the depicted embodiment, the second arm 290 includes a third opening 292 and a fourth opening 294 positioned near the second end 258. The third opening 292 may be spaced apart from the fourth opening 294. The openings 292, 294 may extend from the top surface 252 to the bottom surface 254 of the cut guide 250. The openings 292, 294 may extend through the second arm 290, for example, parallel to the extension member 278, angled as they extend from the top surface 252 toward the bottom surface 254, or a combination of parallel and angled. In one embodiment, the third opening 292 may extend, for example, parallel to the extension member 278 and the fourth opening 294 may be, for example, angled with respect to the extension member 278. Alternative combinations of the orientations of the openings 292, 294 are also contemplated, as would be understood by one of ordinary skill in the art from the above description. In one embodiment, the openings 282, 292 may be, for example, positioned such that they are parallel to one another as they extend between the top and bottom surfaces 252, 254. By positioning the openings 282, 292 parallel to each other, the cut guide 250 may be, for example, removed from guide wires inserted through openings 282, 292 without removing the guide wires. In addition, parallel openings 282, 292 allow for the relative rotation between the two guide wires to be measured or calculated after the bones are cut using cut guide 250. Further the openings 282, 292 may be, for example, spaced apart from the extension member 278 a standard or set distance to allow for interchangeability with alternative cut guides 100, 200, 300, 400, if a different or additional resection is needed. The second arm 290 may be shaped to provide a bone contacting surface 296 that corresponds to the shape of the bone surface that it will engage. The second arm 290 may be, for example, curved or arced as it extends between the first side 260 and the second side 262. The second arm 290 may have, for example, a larger length and width than the first arm 280.

The openings 282, 284, 292, 294 may be positioned such that wires inserted into the first and second openings 282, 284 and wires inserted into the third and fourth openings 292, 294 all cross above the cut guide 250. By positioning the openings 282, 284 and openings 292, 294 such that inserted wires cross above the openings 282, 284 and openings 292, 294, respectively, the surgeon can make a smaller surgical incision and reduce the interaction or interference with other instruments during the procedure. The openings 282, 284, 292, 294 being positioned to allow wires to cross also allows for the cut guide 250 to be, for example, suspended above and/or in contact with the bone surfaces being cut. Suspending the cut guide 250 above the bone surfaces prevents the cut guide 250 from being tilted on the irregular bone surface and therefore avoids moving the slots 282, 284, 292, 294, which would affect the proposed cut angles.

Another cut guide 300 is shown in FIGS. 27-34. The cut guide 300 includes a top surface 302, a bottom surface 304, a first end 306, a second end 308, a first side 310, and a second side 312. The first end 306 may be, for example, a proximal end, and the second end 308 may be, for example, a distal end, or vice versa. The first side 310 may be, for example, a medial side, and the second side 312 may be, for example, a lateral side, or vice versa. The cut guide 300 also includes a base portion 314, a paddle, fin or extension member 322 extending away from the bottom surface 304 of the base portion 314, and an arm 330 extending away from the base portion 314 on the second end 308. As shown in FIGS. 27-34, the cut guide 300 may be, for example, a right foot cut guide. The cut guide 300 may provide, for example, a 4° angulation from dorsal to plantar on the metatarsal.

Cut guide 300 may be used, for example, when a surgeon decides that correction of the first metatarsal in plantarflexion is not sufficient enough and needs to take off more of the metatarsal from the dorsal to plantar direction. Alternatively, cut guide 300 may be used, for example, when a surgeon knows from pre-operative radiographs that the first ray is dorsiflexed in order to cut more bone of the metatarsal plantarly to correct the dorsiflexion. For example, when guide 300 is used, it will be inserted into the patient's joint, the surgeon will use cut guide 300 to cut the first metatarsal, then cut guide 300 will be removed and replaced with another cut guide, such as, cut guide 100, 200, 250, to cut the cuneiform. The second guide 100, 200, 250 will be selected based on the size and desired angular correction of the cuneiform. The cut guide 300 may be removed from the patient's bones, for example, by sliding the guide 300 off a guide wire inserted through the opening 332 and inserting the second cut guide 100, 200, 250 onto the guide wire to properly align the second cut guide 100, 200, 250 on the patient's bones with respect to the first cut made to the metatarsal.

Figure 27:
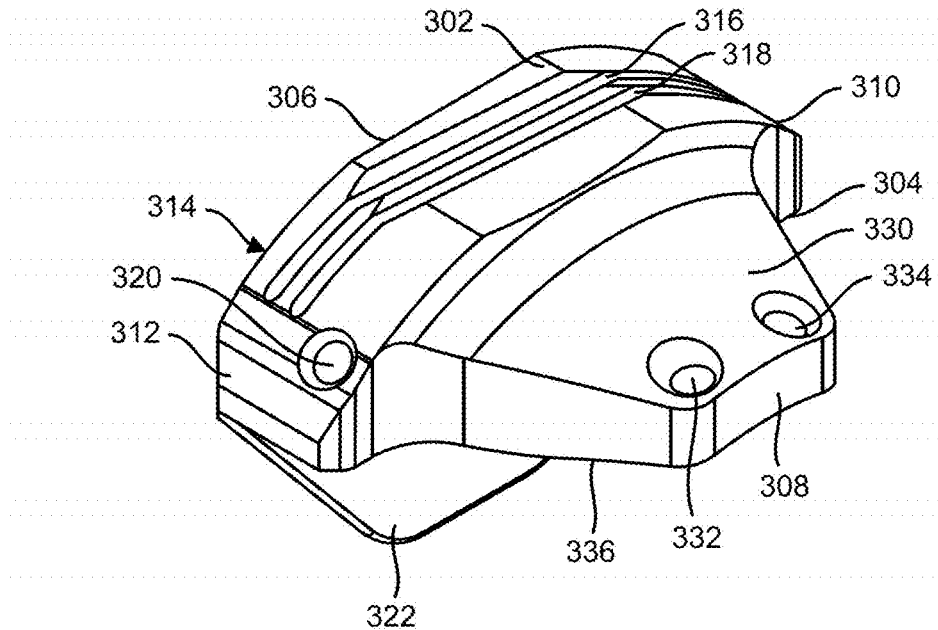
FIG. 27 is a top perspective view of another cut guide, in accordance with an aspect of the present disclosure.
Figure 28:
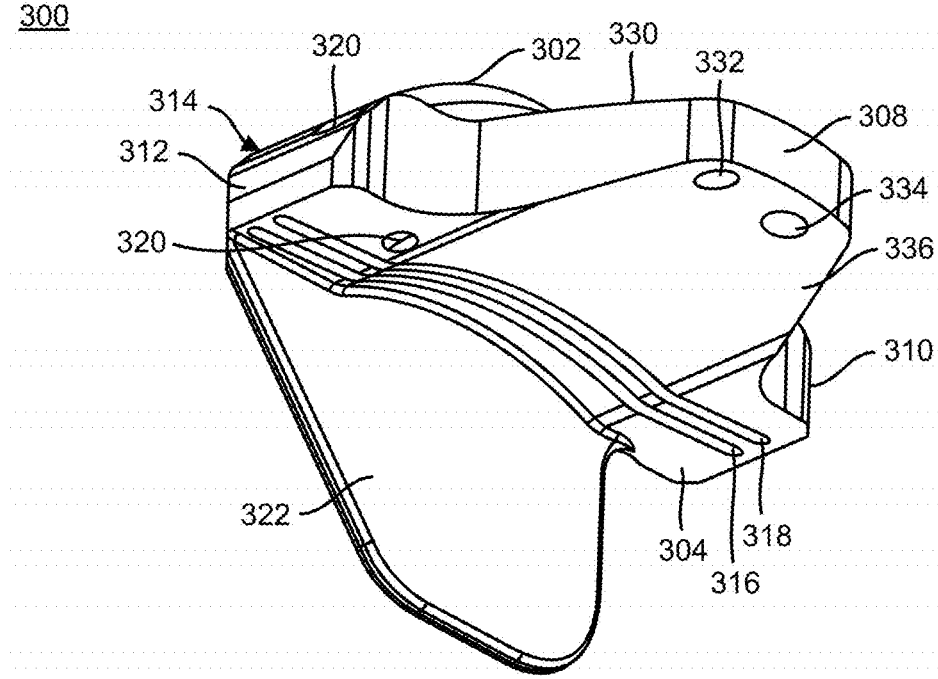
FIG. 28 is a bottom perspective view of the cut guide of FIG. 27, in accordance with an aspect of the present disclosure.
Figure 29:
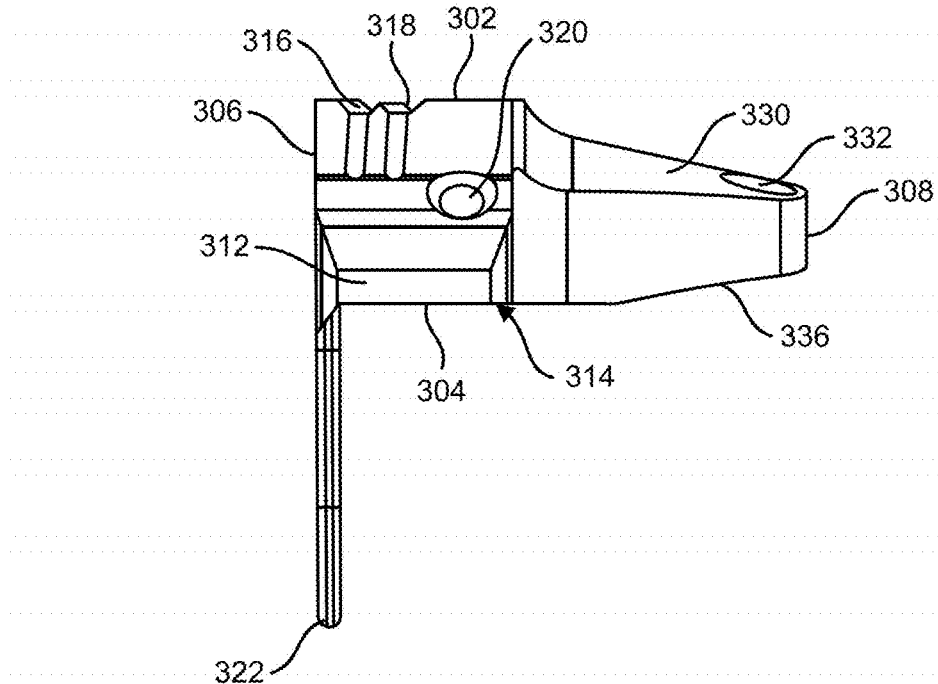
FIG. 29 is a side view of the cut guide of FIG. 27, in accordance with an aspect of the present disclosure.
Figure 30:
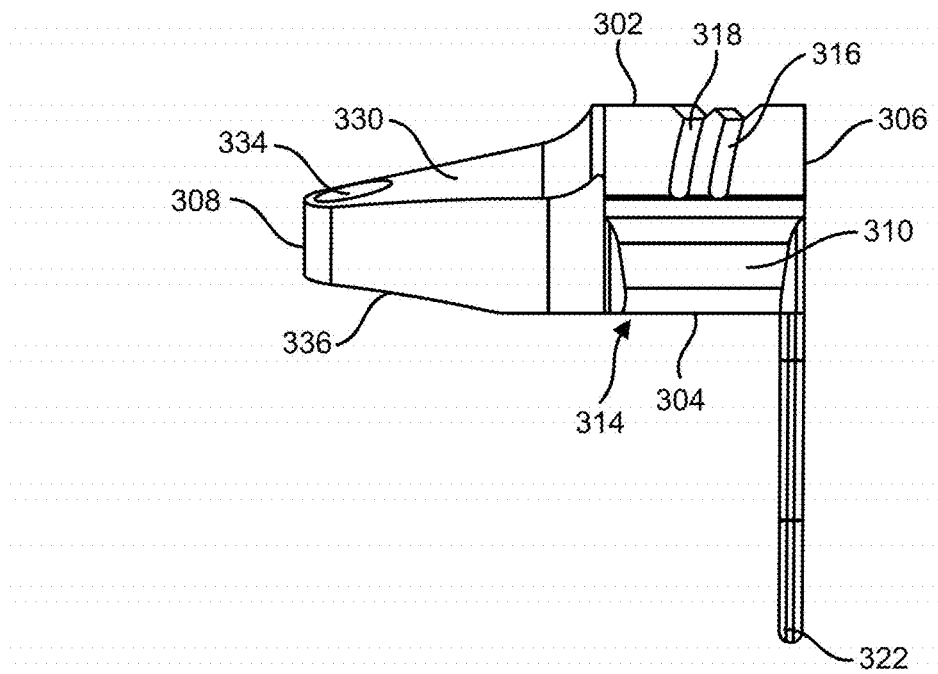
FIG. 30 is another side view of the cut guide of FIG. 27, in accordance with an aspect of the present disclosure.
Figure 31:
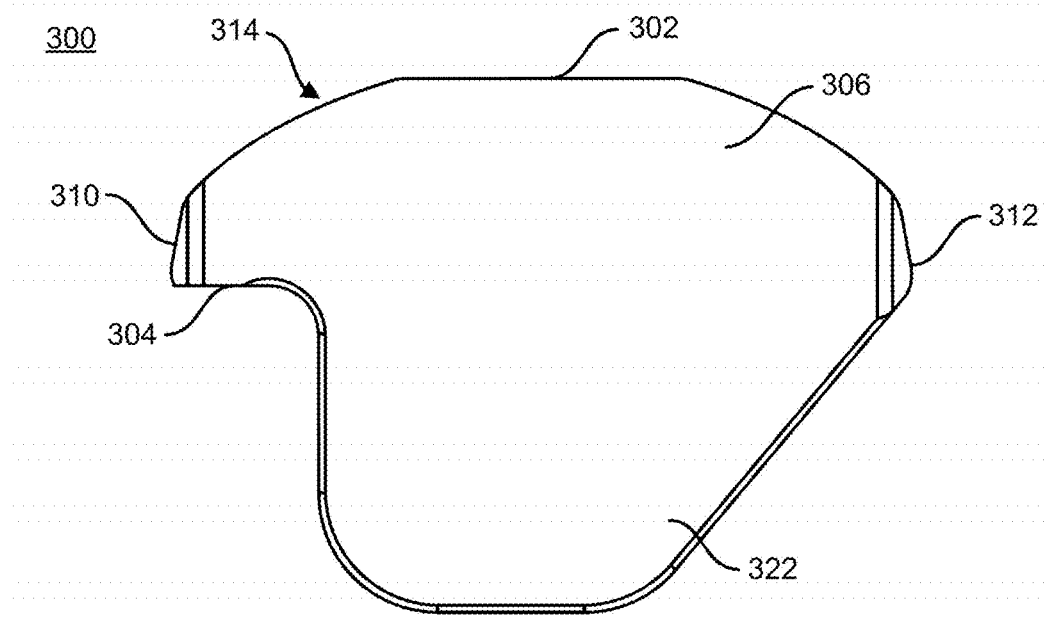
FIG. 31 is an end view of the cut guide of FIG. 27, in accordance with an aspect of the present disclosure.
Figure 32:
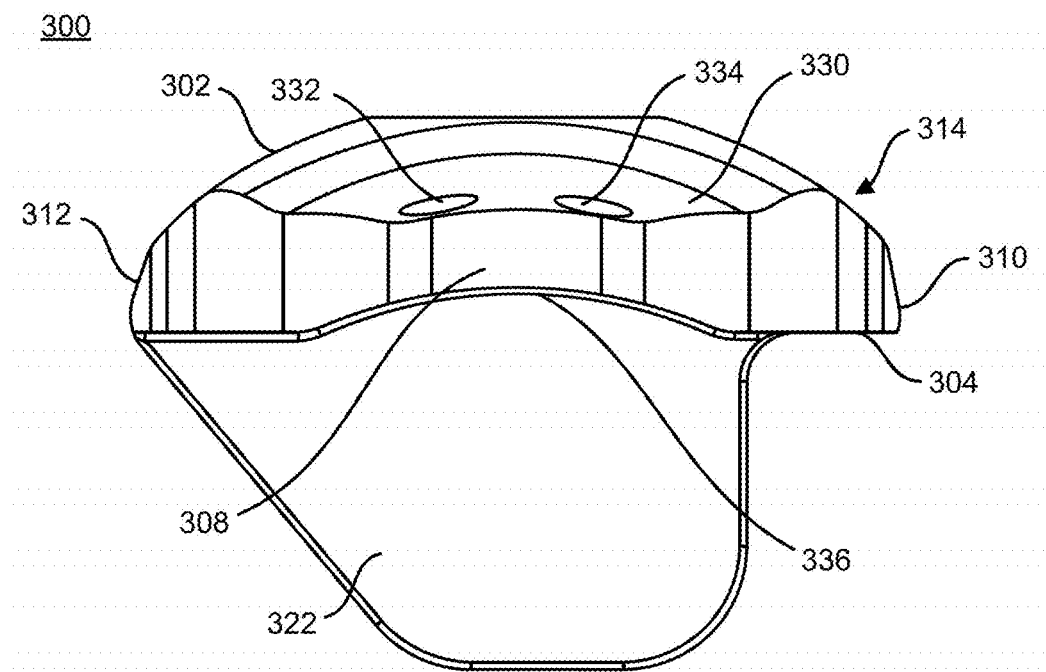
FIG. 32 is another end view of the cut guide of FIG. 27, in accordance with an aspect of the present disclosure.

As shown in FIGS. 27, 31 and 32, the top surface 302 of the base portion 314 may be, for example, curved or arced between the first side 310 and the second side 312. In an embodiment, the top surface 302 of the base portion 314 may include, for example, a flat or planar portion positioned between a first curvature or arc extending from the first side 310 to the flat portion and a second curvature or arc extending from the second side 312 to the flat portion. The base portion 314 also includes at least one slot 316, 318, as shown in FIGS. 27-30, 33 and 34. In the depicted embodiment, the first slot 316 is positioned adjacent to a second slot 318. The slots 316, 318 may extend, for example, through the base portion 314 from the top surface 302 to the bottom surface 304 of the cut guide 300. The slots 316, 318 may be, for example, angled as the slots 316, 318 extend from the top surface 302 to the bottom surface 304. The slots 316, 318 may be angled, for example, approximately 1° to 4° and more specifically, approximately 2°, as the slots 316, 318 extend between the top surface 302 and the bottom surface 304. It is also contemplated that the interior slot 316 may be angled while the exterior slot 318 may be linear as they extend between the top and bottom surfaces 302, 304.

Figure 33:
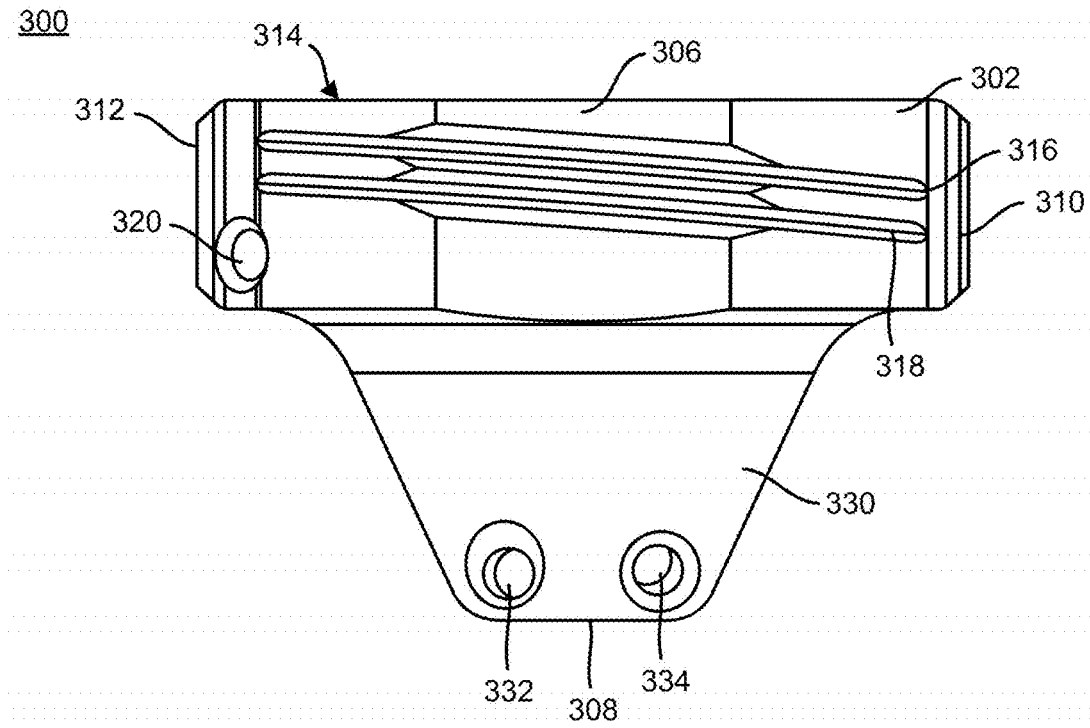
FIG. 33 is a top view of the cut guide of FIG. 27, in accordance with an aspect of the present disclosure.
Figure 34:
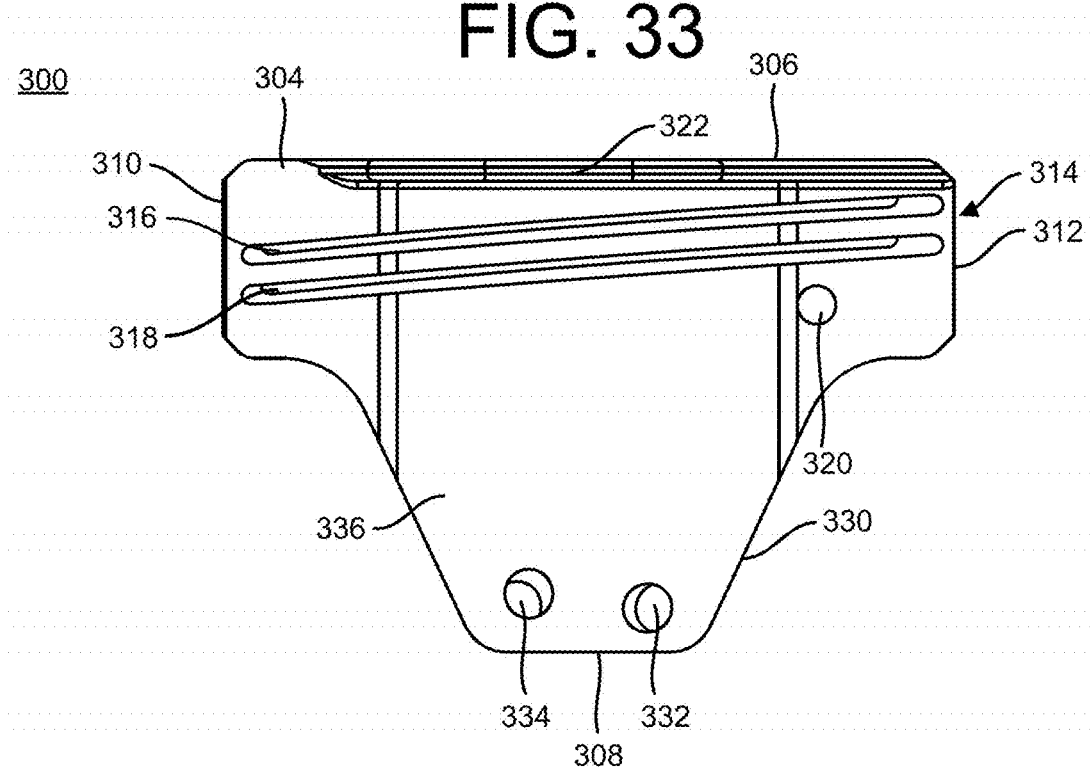
FIG. 34 is a bottom view of the cut guide of FIG. 27, in accordance with an aspect of the present disclosure.

In addition, the slots 316, 318 may be angled as they extend across the base portion 314 from the first side 310 to the second side 312, as shown in FIGS. 33 and 34. The slots 316, 318 may be, for example, angled at approximately 6° as they extend between the first and second sides 310, 312 providing for an angulation correction of 4°. The slots 316, 318 may be configured or sized and shaped to receive a saw blade and may have a width of, for example, approximately 0.58 mm to 0.92 mm. As shown in FIG. 33, the slots 316, 318 may be angled from a distal-medial position to a proximal-lateral position of the cut guide 300. The slots 316, 318 may be positioned, for example, to allow for removal of the articular cartilage only. To prevent resecting too much tissue, the slots 316, 318 may be positioned, for example, such that the medial portion of the slots 316, 318 are aligned with the cartilage and bone boundary.

The base portion 314 also includes a hole or dorsal hole 320, as shown in at least FIGS. 27-29, 33 and 34. The hole 320 is positioned between the second slot 318 and the arm 330. The hole 320 may extend, for example, through the base portion 314 from the top surface 302 to the bottom surface 304. The hole 320 may, for example, extend through the base portion 314 of the cut guide 300 parallel to the angled portion of the extension member 322, as shown in FIG. 27. The hole 320 may be sized and shaped or configured, for example, to receive a wire, alignment wire, k-wire, guide wire, directional wire or the like to provide information on the position of the cut guide 300 in a joint. For example, the wire inserted into hole 320 should align approximately with the long axis of the tibia to provide the proper orientation of the cut guide 300 in the joint, which may be, for example, approximately 45° from dorsal and 45° from medial in the frontal plane.

Referring now to FIGS. 28-32 and 34, the extension member 322 is attached to a bottom surface 304 of the base portion 314. The extension member 322 also extends away from the base portion 314 and is positioned on the first end 306 of the cut guide 300. In addition, the extension member 322 extends from the second side 312 toward the first side 310, as shown in at least FIGS. 28, 31 and 32. The extension member 322 may include a portion near the first side 310 that extends perpendicularly away from the bottom surface 304. The perpendicular portion of the extension member 322 may be, for example, angled when the cut guide 300 is inserted into a patient's joint and the angle that the perpendicular portion is positioned at may correspond to the angle of the first tarso-metatarsal joint medially. The extension member 322 may also include an angled portion extending from the second side 312 to the end of the extension member 322. The extension member 322 may be shaped, for example, to fit within the joint space between the two bones, such as, a first metatarsal and cuneiform, as well as to mate with the two sides of an articular joint. The angled portion of the extension member 322 may, for example, be oriented laterally and should align with the long axis of the tibia, as well as fit within the joint to rest against the relatively straight surface of the adjacent bone, for example, the second metatarsal. When the angled portion of the extension member 322 is oriented against the second metatarsal, the cut guide 300 will be positioned at a 45° angle in the frontal plane.

As shown in FIGS. 27-30 and 32-34, the arm 330 may extend away from an end of the base portion 314 and may be, for example, tapered from the base portion 314 to the second end 308 of the cut guide 300. The arm 330 may be, for example, a distal arm. The arm 330 may include at least one opening 332, 334. In the depicted embodiment, the arm 330 includes a first opening 332 and a second opening 334 positioned near the second end 308. The first opening 332 may be spaced apart from the second opening 334. The openings 332, 334 may extend from a top surface 302 to a bottom surface 304 of the cut guide 300. The openings 332, 334 may extend through the arm 330, for example, parallel to the extension member 322, be angled as the openings 332, 334 extend from the top surface 302 toward the bottom surface 304, or a combination of being parallel and angled. In one embodiment, the first opening 332 may extend, for example, parallel to the extension member 322 and the second opening 334 may be, for example, angled with respect to the extension member 322 resulting in the inserted wires, guide wires, k-wires and the like to cross above the cut guide 300. By positioning the openings 332, 334 such that the inserted wires cross above the openings 332, 334, the surgeon may make a smaller surgical incision and there will be less interaction or interference with other instruments during the procedure. Alternative combinations of the orientations of the openings 332, 334 are also contemplated, as would be understood by one of ordinary skill in the art from the above description. The arm 330 may be shaped, for example, to provide a bone contacting surface 336 that corresponds to the surface or shape of the bone that the arm 330 will engage. The arm 330 may be, for example, curved or arced as it extends between the first side 310 and the second side 312.

Figure 35:
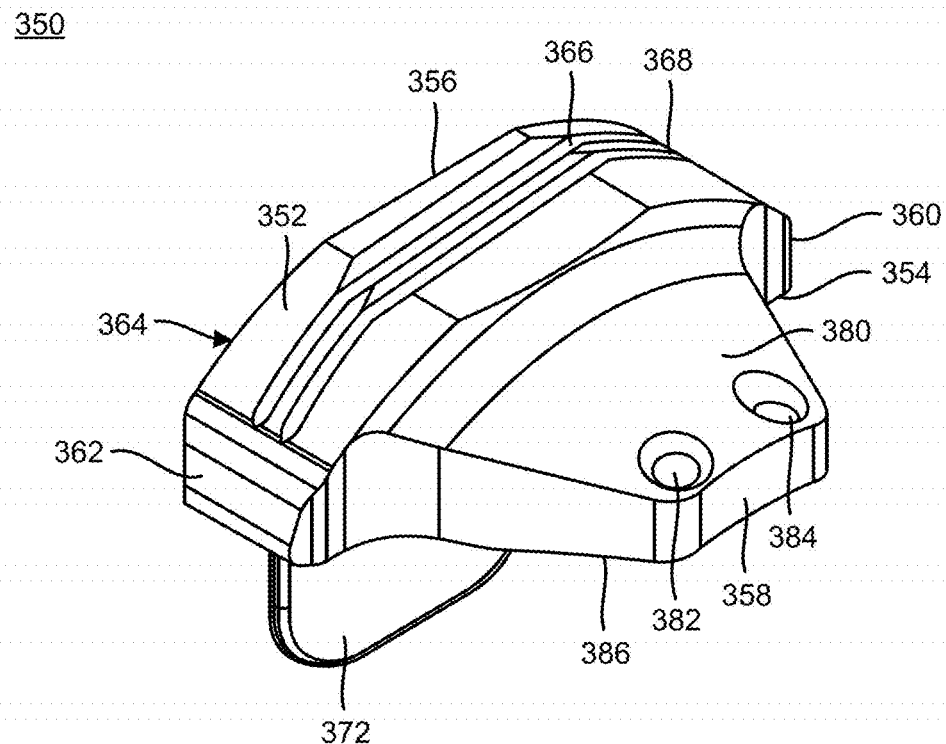
FIG. 35 is a top perspective view of another cut guide, in accordance with an aspect of the present disclosure.
Figure 36:
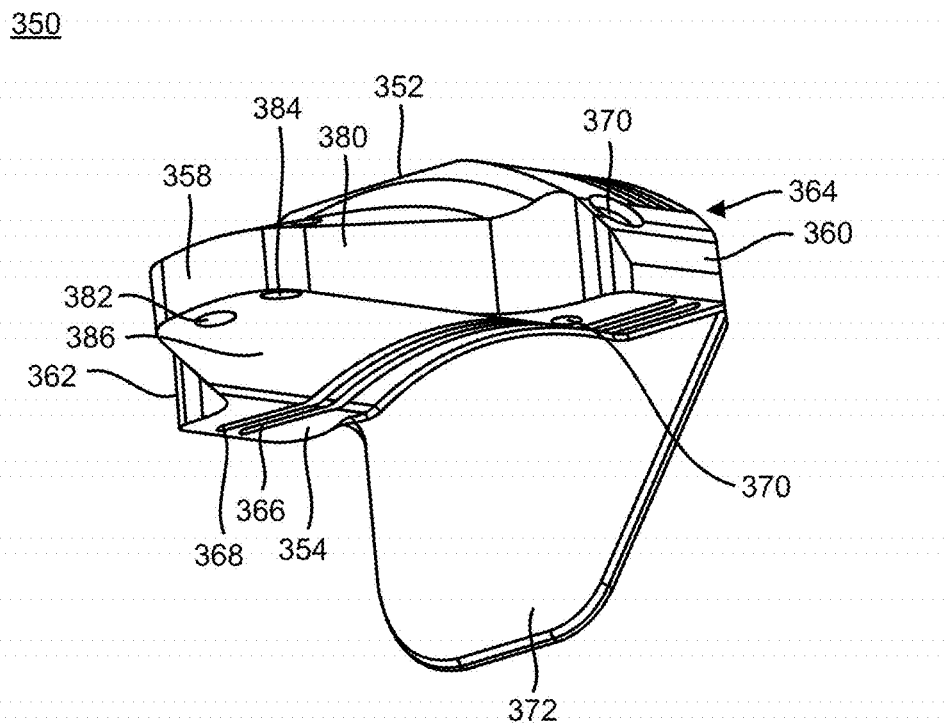
FIG. 36 is a bottom perspective view of the cut guide of FIG. 35, in accordance with an aspect of the present disclosure.
Figure 37:
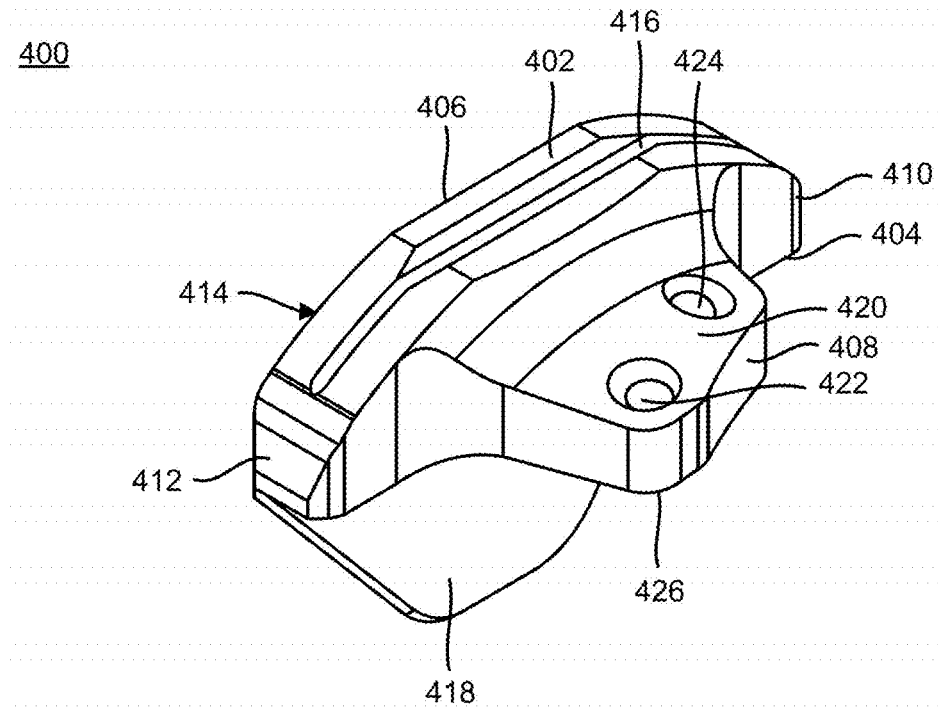
FIG. 37 is a top perspective view of another cut guide, in accordance with an aspect of the present disclosure.
Figure 38:
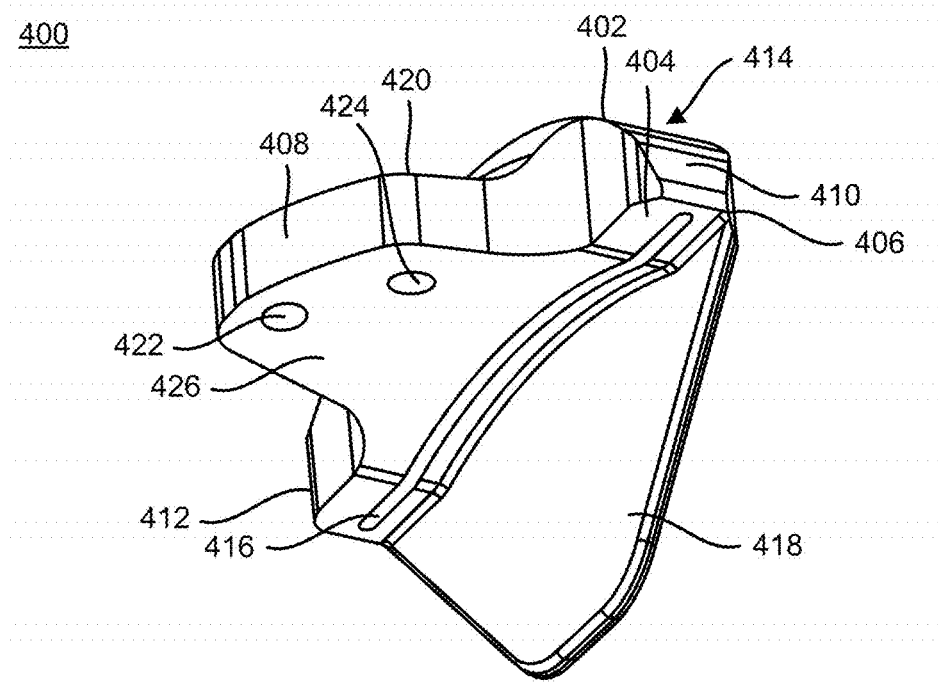
FIG. 38 is a bottom perspective view of the cut guide of FIG. 37, in accordance with an aspect of the present disclosure.
Figure 39:
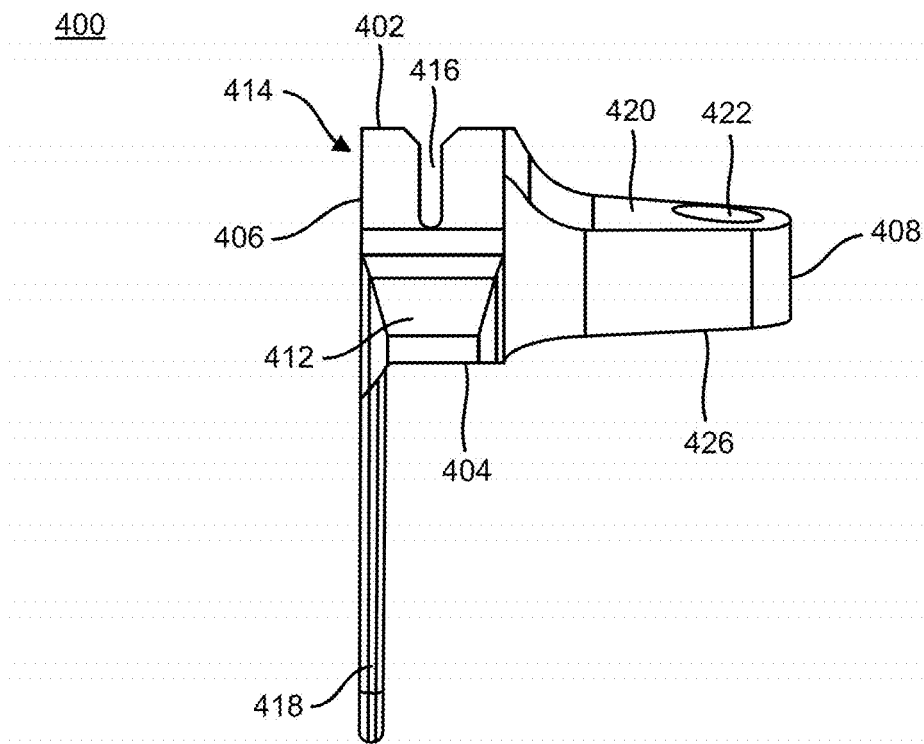
FIG. 39 is a side view of the cut guide of FIG. 37, in accordance with an aspect of the present disclosure.
Figure 40:
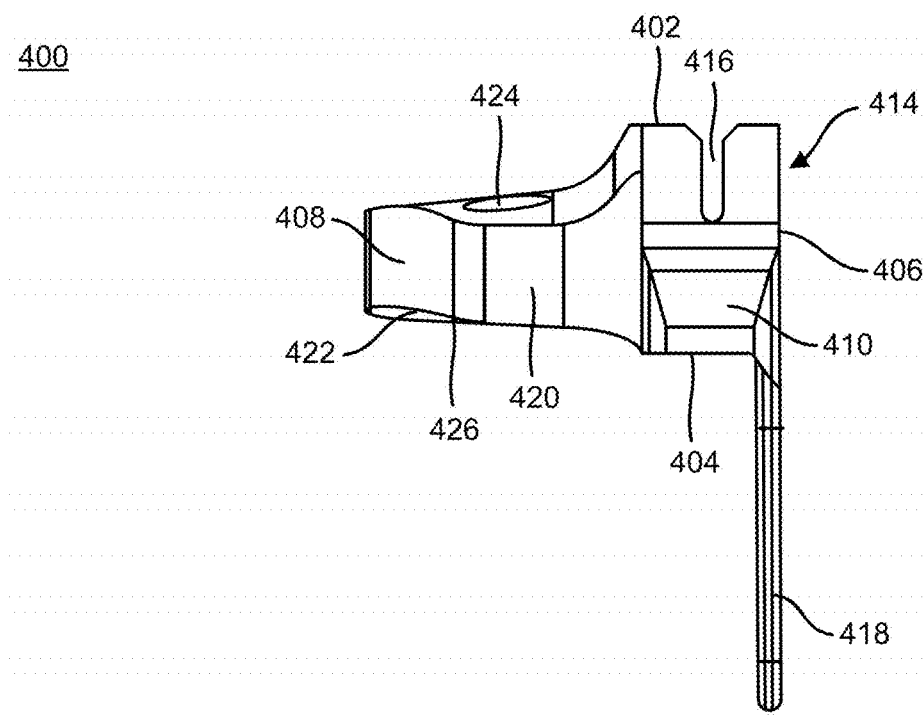
FIG. 40 is another side view of the cut guide of FIG. 37, in accordance with an aspect of the present disclosure.

Referring now to FIGS. 35 and 36, another cut guide 350 is shown. As shown, the cut guide 350 may be a mirror image of the cut guide 300 in a medial-lateral direction, therefore, the cut guide 350 will not be described in full detail for brevity purposes. Therefore, the cut guide 350 may be, for example, for a left foot. The cut guide 350 may include a top surface 352, a bottom surface 354, a first or proximal end 356, a second or distal end 358, a first or medial side 360, and a second or lateral side 362, which may be as described above with respect to the top surface 302, the bottom surface 304, the first or proximal end 306, the second or distal end 308, the first or medial side 310, and the second or lateral side 312, respectively, which will not be described again here for brevity sake. As the cut guide 350 is a mirror image of the cut guide 300, the cut guide 350 may also include a base portion 364 which may be the mirror image of the base portion 314 as described above. In addition, the hole 320 is positioned on a left side of the cut guide 300 when in an insertion position and the hole 370 is positioned on the right side of the cut guide 350 when in an insertion position. The slots 366, 368 and the hole 370 may be similar to the slots 316, 318 and hole 320, as described in greater detail above. Specifically, as the cut guide 350 is a mirror image of the cut guide 300, the slots 366, 368 may be angled from a distal-lateral position to a proximal-medial position of the cut guide 350 resulting in 4° of cumulative dorsal to plantar cutting, as described in greater detail above with reference to cut guide 300. Further, the cut guide 350 may include a fin, paddle or extension member 372 and an arm 380, which may be as described above with respect to the fin, paddle or extension member 322 and the arm 330, respectively. The openings 382, 384 and bone contacting surface 386 may be as described above with reference to the openings 332, 334 and bone contacting surface 336, which will not be described again here for brevity purposes.

Another cut guide 400 is shown in FIGS. 37-44. The cut guide 400 includes a top surface 402, a bottom surface 404, a first end 406, a second end 408, a first side 410, and a second side 412. The first end 406 may be, for example, a proximal end, and the second end 408 may be, for example, a distal end, or vice versa. The first side 410 may be, for example, a medial side, and the second side 412 may be, for example, a lateral side, or vice versa. The cut guide 400 also includes a base portion 414, a paddle, fin or extension member 418 extending away from the bottom surface 404 of the base portion 414, and an arm 420 extending away from the base portion 414 on the second end 408. The cut guide 400 may be, for example, used on a right foot or a left foot.

The cut guide 400 may be, for example, used after any one of cut guides 100, 150, 200, 250, 300, 350 to take off additional tissue or bone when the original cut does not take off enough tissue or bone. The cut guide 400 may be positioned so that the extension member 418 is against and parallel to a previous cut in the joint, to cut away additional tissue or bone without changing the angulation of the prior cut.

Figure 41:
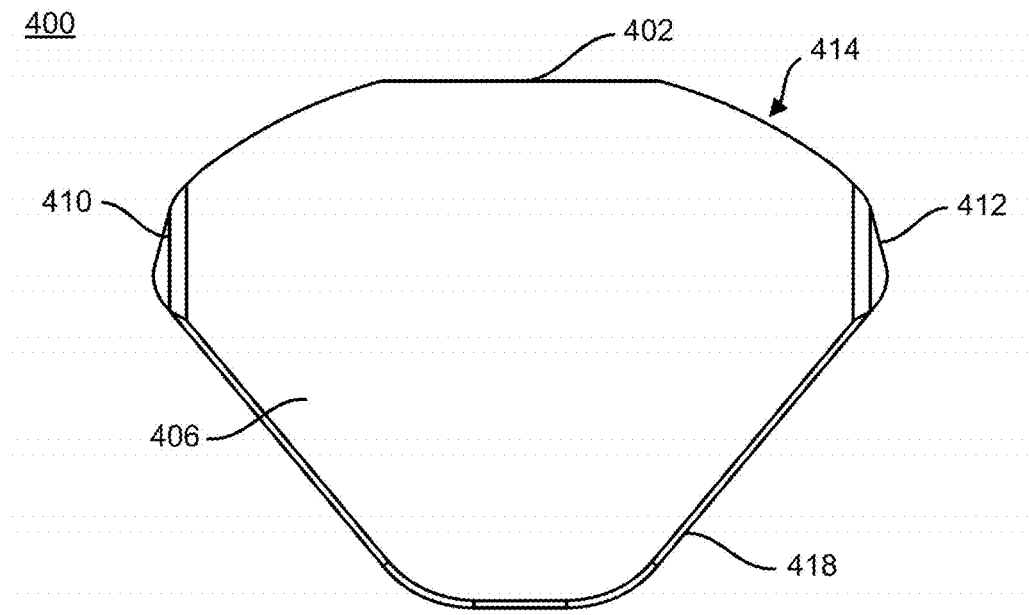
FIG. 41 is a first end view of the cut guide of FIG. 37, in accordance with an aspect of the present disclosure.
Figure 42:
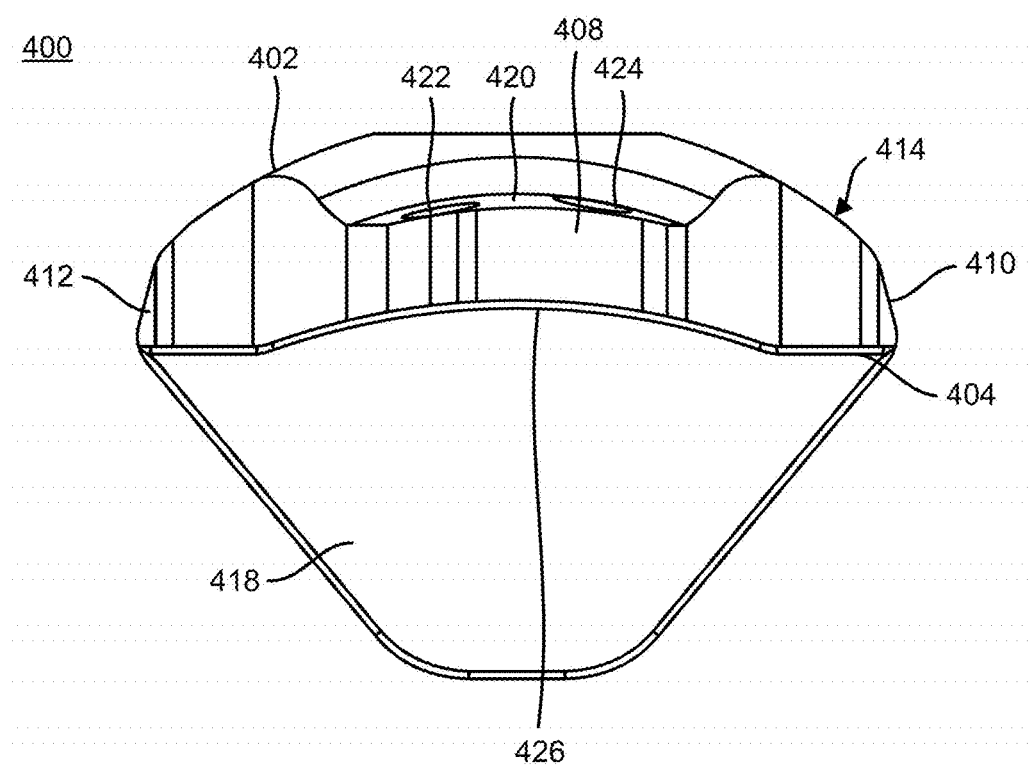
FIG. 42 is a second end view of the cut guide of FIG. 37, in accordance with an aspect of the present disclosure.
Figure 43:
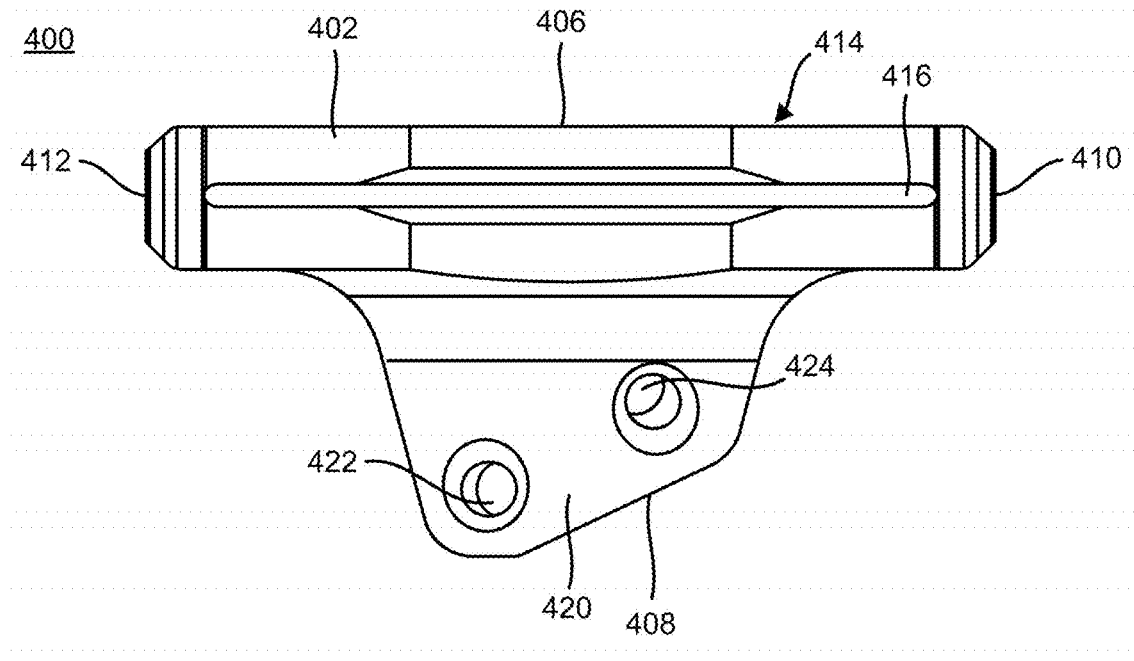
FIG. 43 is a top view of the cut guide of FIG. 37, in accordance with an aspect of the present disclosure.
Figure 44:
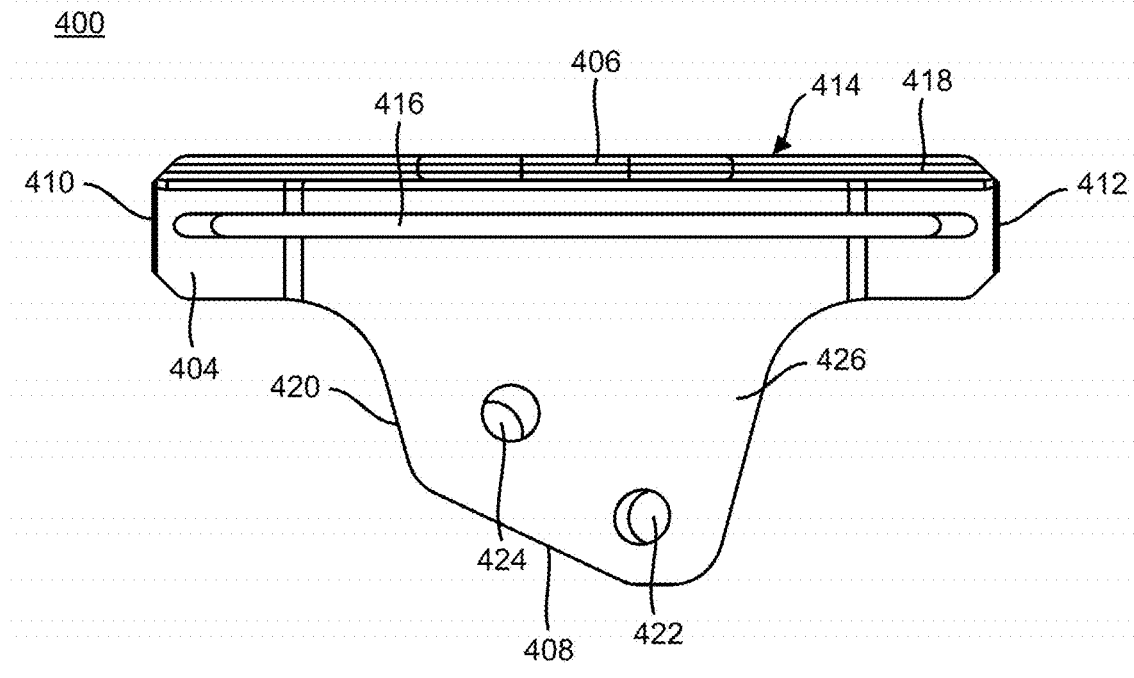
FIG. 44 is a bottom view of the cut guide of FIG. 37, in accordance with an aspect of the present disclosure.

As shown in FIGS. 41 and 42, the top surface 402 of the base portion 414 may be, for example, curved or arced between the first side 410 and the second side 412. In an embodiment, the top surface 402 of the base portion 414 may include, for example, a flat or planar portion positioned between a first curvature or arc extending from the first side 410 to the flat portion and a second curvature or arc extending from a second side 412 to the flat portion. The base portion 414 also includes at least one slot 416, as shown in FIGS. 37-40, 43 and 44. In the depicted embodiment, the slot 416 is positioned near a center or longitudinal axis of the base portion 414. The slot 416 may extend, for example, linearly through the base portion 414 from the top surface 402 to the bottom surface 404 of the cut guide 400. The slot 416 may also be, for example, positioned parallel with the extension member 418, as the slot 416 extends from between the top surface 402 and the bottom surface 404. The slot 416 may be positioned, for example, to allow for removal of the articular cartilage layer of the bones. To prevent resecting more bone than absolutely necessary, the slot 416 may be positioned, for example, such that the medial portion of the slot 416 is aligned with the cartilage-bone border. The slot 416 may be positioned, for example, a first distance from the extension member 418. The slot 416 may be configured or sized and shaped to receive a saw blade and may have a width of, for example, approximately 0.58 mm to 0.92 mm.

Referring now to FIGS. 37-42 and 44, the extension member 418 is coupled to a bottom surface 404 of the base portion 414. The extension member 418 also extends away from the base portion 414 and is positioned on the first end 406 of the cut guide 400. In addition, the extension member 418 extends from the second side 412 to the first side 410, as shown in at least FIGS. 38, 41 and 42. The extension member 418 may be tapered and include a first angled portion extending from the first side 410 to the end of the extension member 418 and a second angled portion extending from the second side 412 to the end of the extension member 418. As the cut guide 400 may be used on either a right or left foot, extension member 418 is angled on both the first and second sides 410, 412 to allow for an angled portion to mate with the lateral side of the joint. Further, the angled portion may rest against the relatively straight surface of the adjacent bone, for example, the second metatarsal. When an angled portion of the extension member 418 is oriented against the second metatarsal, the cut guide 400 will be positioned at a angle medial in the frontal plane. The extension member 418 may be shaped, for example, to fit within the joint space between two bones, such as, a first metatarsal and cuneiform, as well as to mate with the surface of an articular joint.

As shown in FIGS. 37-40 and 42-44, the arm 420 may extend away from an end of the base portion 414 and may be, for example, tapered from the base portion 414 to the second end 408 of the cut guide 400. The portion of the arm 420 at the second end 408 of the cut guide 400 may be, for example, angled as the arm 420 extends from the second side 412 to the first side 410. The arm 420 may be, for example, a distal arm. The arm 420 may include at least one opening 422, 424. In the depicted embodiment, the arm 420 includes a first opening 422 and a second opening 424 positioned near the second end 408. The first opening 422 may be spaced apart from the second opening 424. The openings 422, 424 may extend from the top surface 402 through the bottom surface 404. The openings 422, 424 may extend through the arm 420, for example, parallel to the extension member 418, angled with respect to the top surface 402 and the bottom surface 404, or a combination of being parallel and angled. In one embodiment, the first opening 422 may extend, for example, parallel to the extension member 418 and the second opening 424 may be, for example, angled with respect to the extension member 418 to cause the inserted wires, guide wires, k-wires and the like to cross above the cut guide 400. By positioning the openings 422, 424 such that inserted wires cross above the openings 422, 424, a smaller surgical incision may be made and less interaction or interference with other instruments will be experienced during the procedure. The openings 422, 424 positioning the wires to cross also allows for the cut guide 400 to be, for example, suspended above and/or against the bone surfaces being cut. The ability to suspend the cut guide 400 above the bone surfaces prevents the cut guide 400 from being angled or tilted because of the inconsistent bone surface which avoids moving the slot 416 and prevents the proposed cut angles from being moved. Alternative combinations of the orientations of the openings 422, 424 are also contemplated, as would be understood by one of ordinary skill in the art from the above description. The arm 420 may be shaped, for example, to provide a bone contacting surface 426 that corresponds to the shape of the bone surface that the arm 420 will engage. The arm 420 may be, for example, curved or arced as it extends between the first side 410 and the second side 412.

With continued reference to the cut guide 400 of FIGS. 37-44, an alternative embodiment cut guide 430 and insertion handle 450 are shown in FIGS. 66-74. The cut guide 430 includes a top surface 402, a bottom surface 404, a first end 406, a second end 408, a first side 410, and a second side 412, as described in greater detail above with reference to cut guide 400 and which will not be described again here for brevity sake. The cut guide 430 also includes a base portion 414, a paddle, fin or extension member 418 extending away from the bottom surface 404 of the base portion 414, and an arm 420 extending away from the base portion 414 on the second end 408, as described in greater detail above with reference to cut guide 400 and which will not be described again here for brevity sake. The base portion 414 also includes at least one slot 416, as also described in greater detail above with reference to cut guide 400 and which will not be described again here for brevity sake. The arm 420 may include at least one opening 422, 424, as described in greater detail above with reference to cut guide 400 and which will not be described again here for brevity sake. The arm 420 may be shaped, for example, to provide a bone contacting surface 426 that corresponds to the shape of the bone surface that the arm 420 will engage, as described in greater detail above with reference to cut guide 400 and which will not be described again here for brevity sake. The cut guide 430 may be, for example, used on a right foot or a left foot.

As shown in FIGS. 66-69 and 71, the cut guide 430 may also include a recess or opening 432 inset into the surface of the base portion 414 on the first end 406. The recess 432 may have, for example, an oval, round, or a polygonal shaped recess for receiving a correspondingly shaped protrusion 460 on an insertion handle 450. The insertion handle 450 allows for a surgeon to apply pressure against a patient's joint to achieve maximum contact between the cut guide 430 and the previously cut bone. As shown in FIGS. 66-74, the insertion handle 450 includes a handle portion 452 with a stem portion 454 extending away from a distal end of the handle portion 452. The stem portion 454 includes a tip 456 at the distal end of the stem portion 454. The tip 456 includes an end surface 458 which may be, for example, angled with respect to the proximal end of the handle portion 452. The end surface 458 may be, for example, angled to provide the desired angle for insertion of the cut guide 430. The insertion handle 450 may further include an engagement member or protrusion 460 extending away from the end surface 458. The engagement member 460 may be, for example, shaped to correspond to the recess 432 in the cut guide 430. The engagement member 460 may have, for example, an oval, round or polygonal shape.

Figure 45:
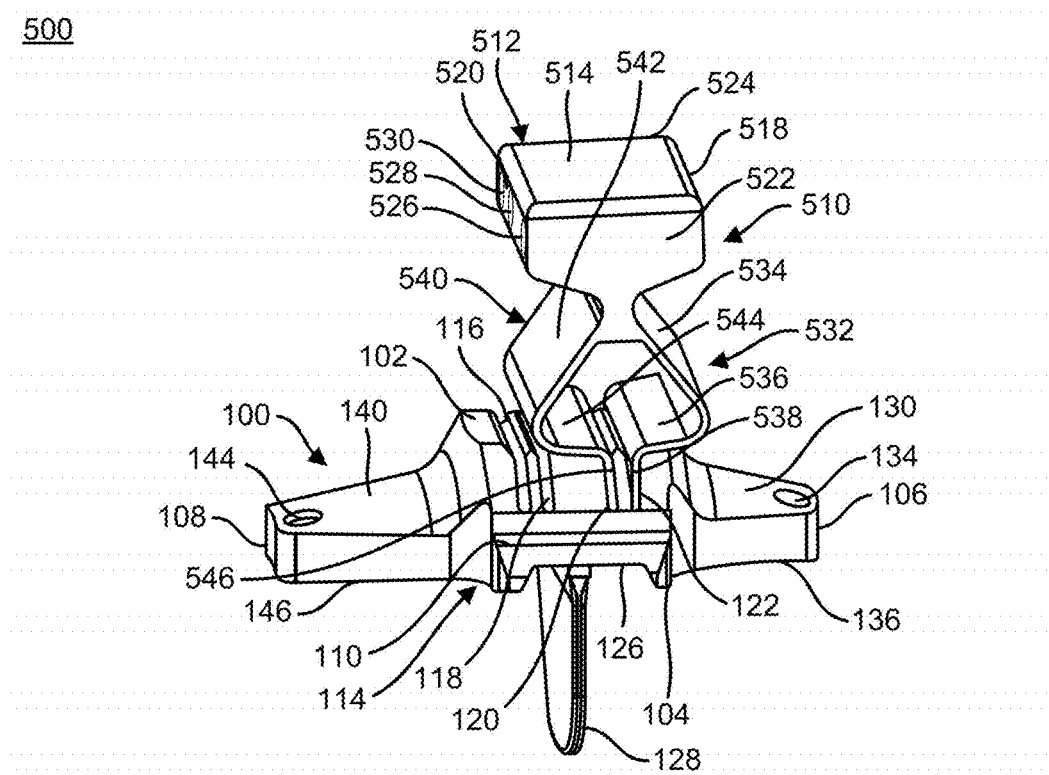
FIG. 45 is a first side, perspective view of a guide system including an alignment guide and the cut guide of FIG. 1, in accordance with an aspect of the present disclosure.
Figure 46:
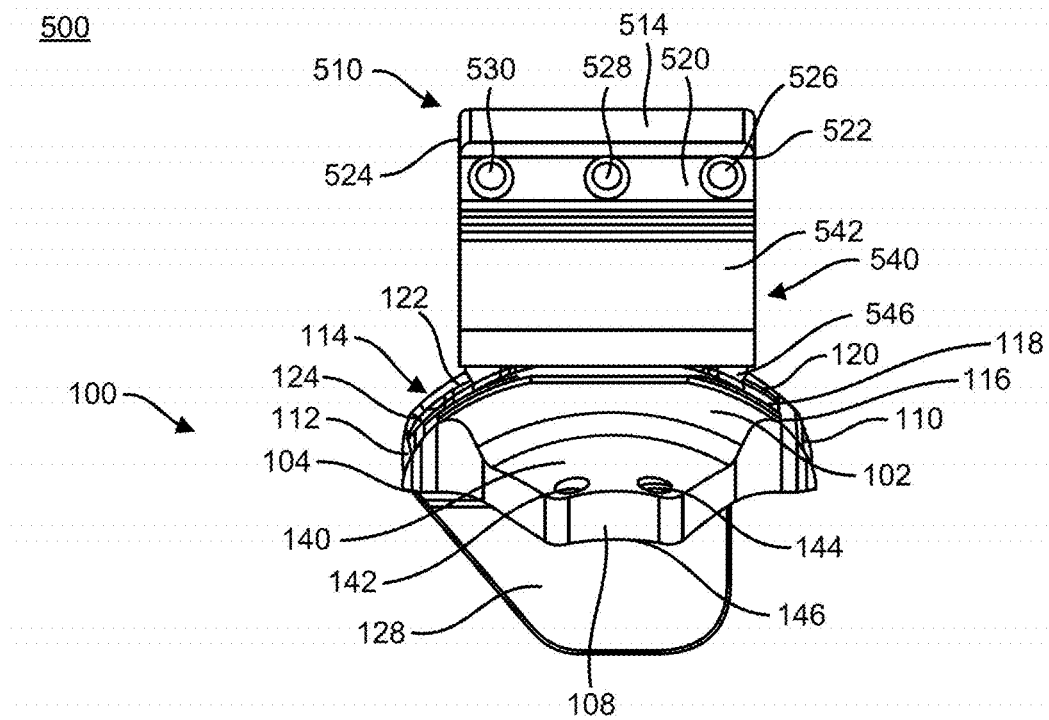
FIG. 46 is a first end, perspective view of the guide system of FIG. 45, in accordance with an aspect of the present disclosure.
Figure 47:
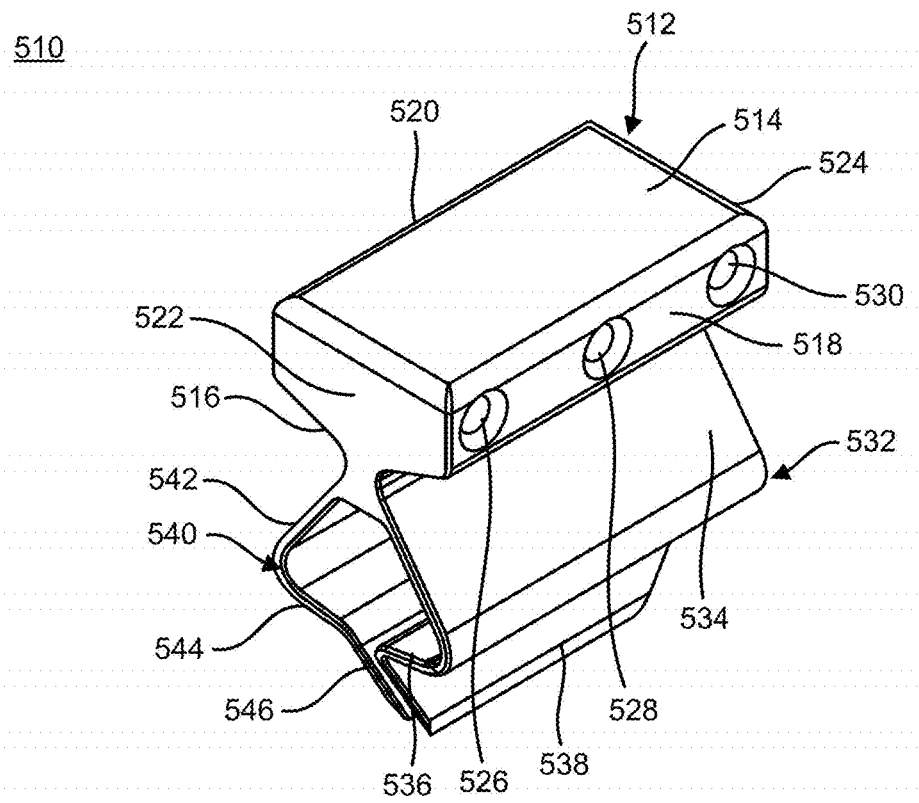
FIG. 47 is a first side, perspective view of the alignment guide of FIG. 45, in accordance with an aspect of the present disclosure.
Figure 48:
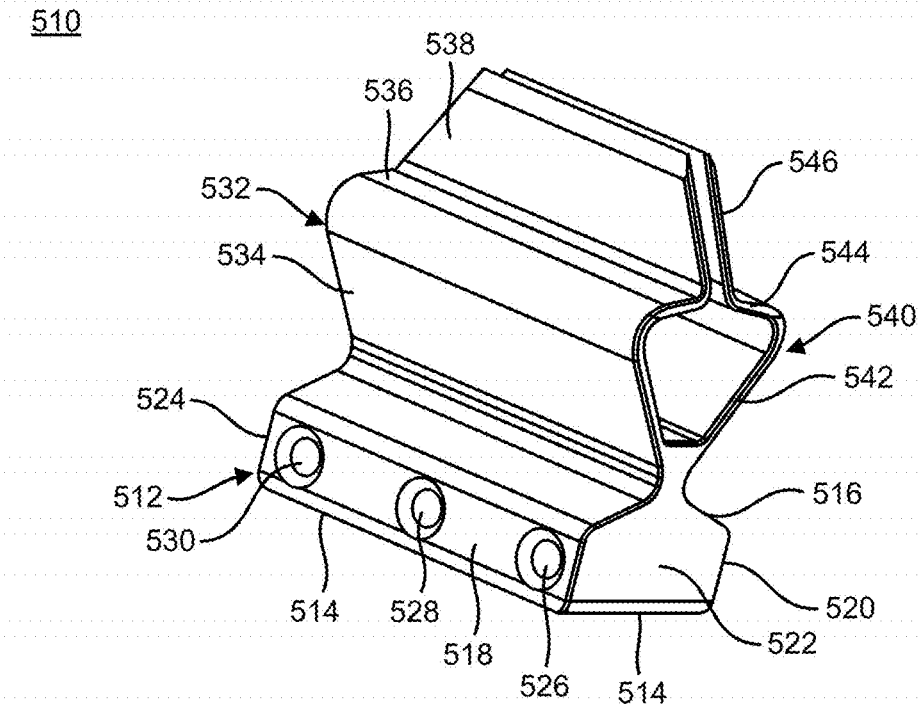
FIG. 48 is a second side, perspective view of the alignment guide of FIG. 47, in accordance with an aspect of the present disclosure.
Figure 49:
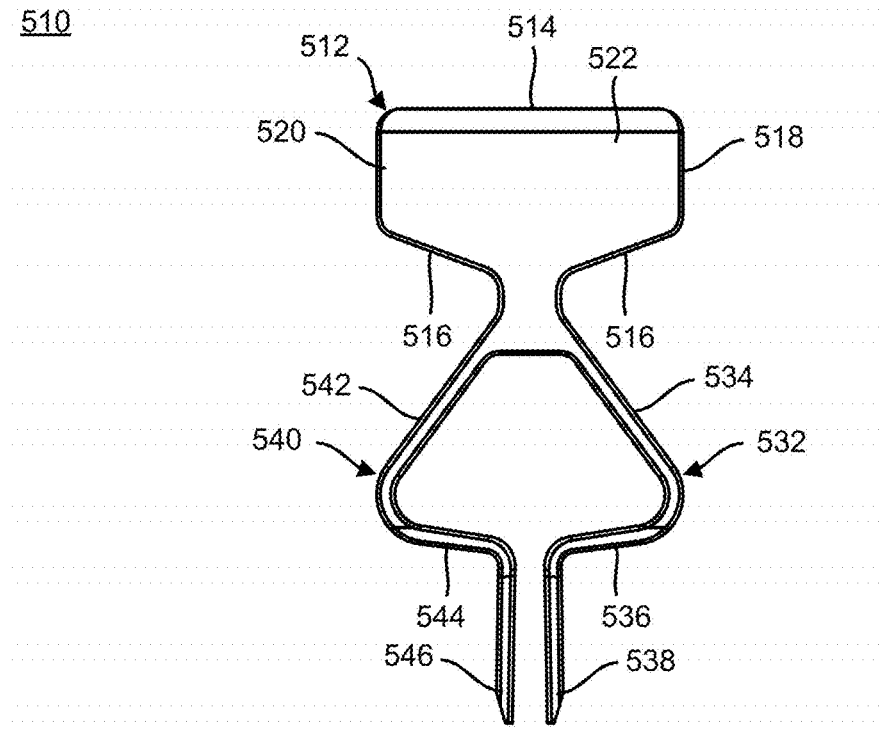
FIG. 49 is a side view of the alignment guide of FIG. 47, in accordance with an aspect of the present disclosure.
Figure 50:
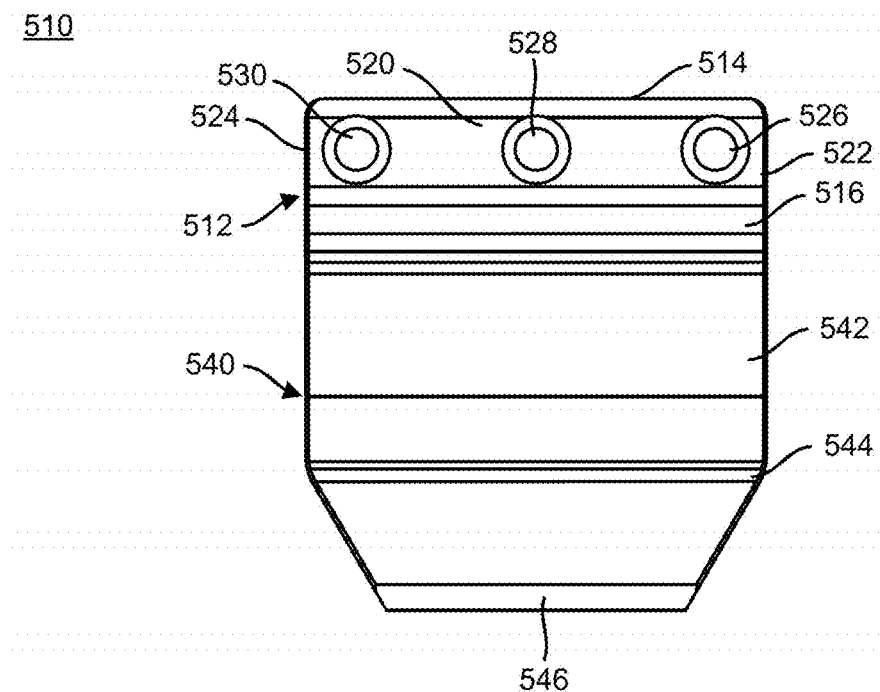
FIG. 50 is an end view of the alignment guide of FIG. 47, in accordance with an aspect of the present disclosure.
Figure 51:
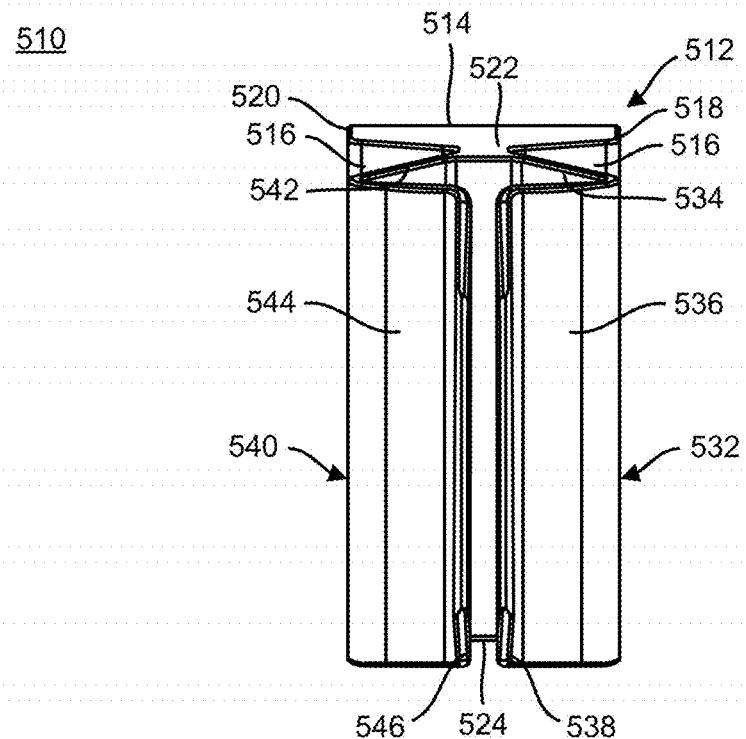
FIG. 51 is a bottom perspective view of the alignment guide of FIG. 47, in accordance with an aspect of the present disclosure.
Figure 52:
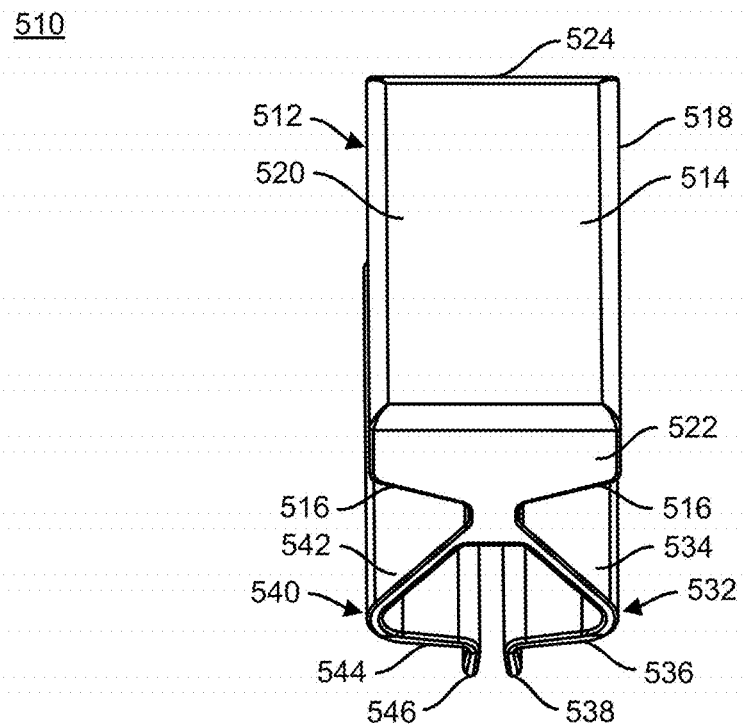
FIG. 52 is a top perspective view of the alignment guide of FIG. 47, in accordance with an aspect of the present disclosure.
Figure 57:
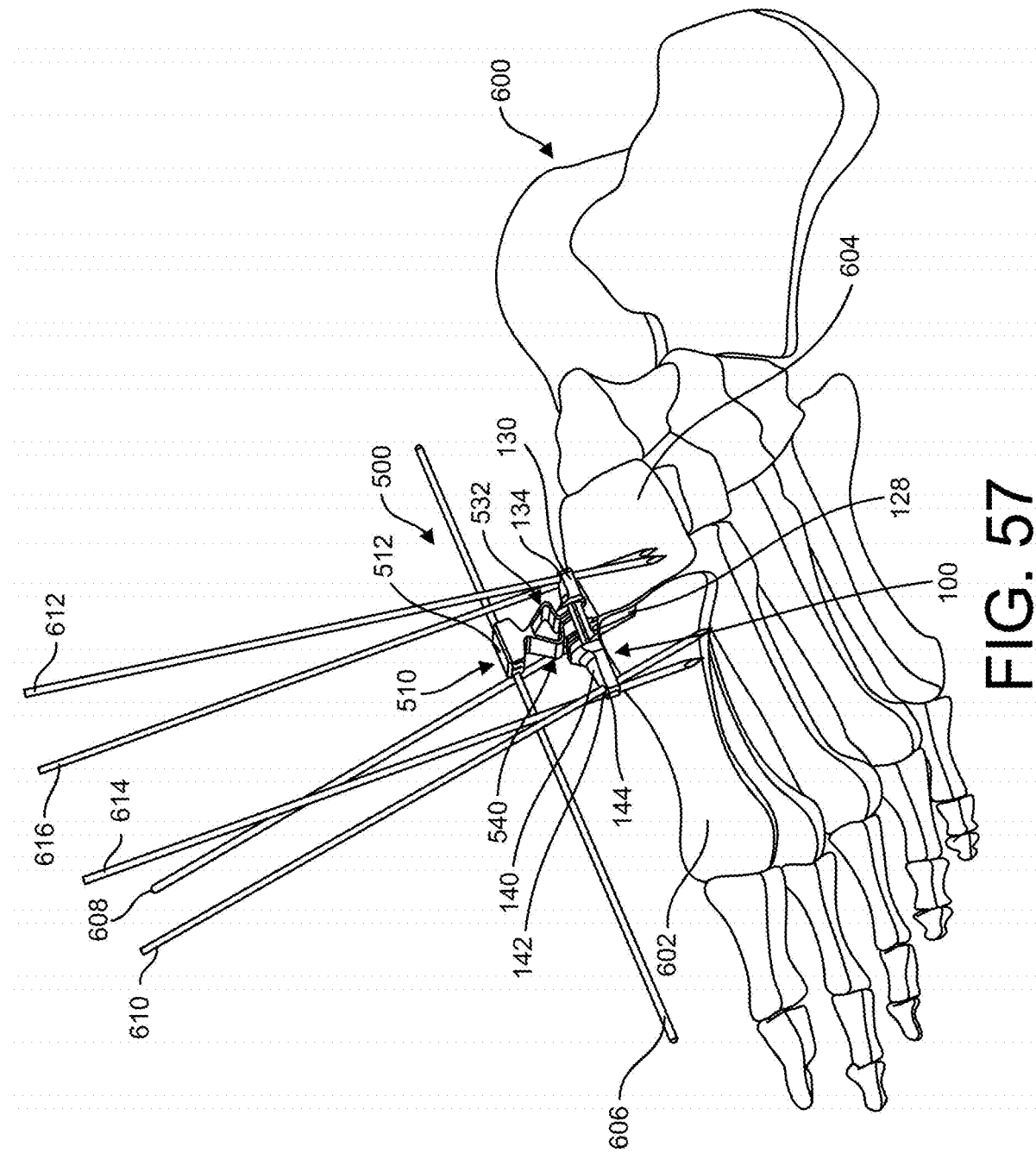
FIG. 57 is a bottom perspective view of FIGS. 55 and 56 with guide wires inserted through the cut guide into the bones of the foot, in accordance with an aspect of the present disclosure.
Figure 58:
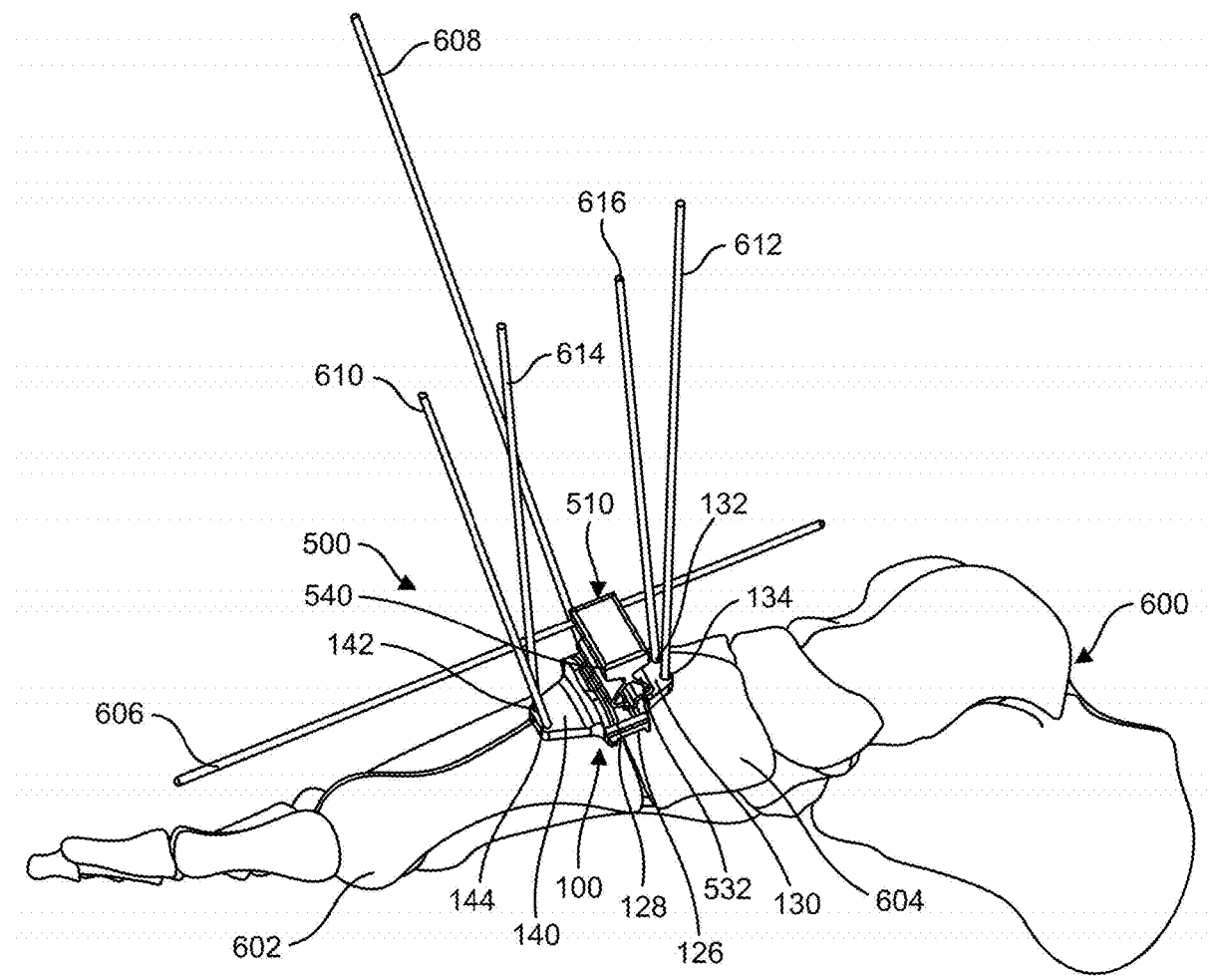
FIG. 58 is a side view of FIG. 57, in accordance with an aspect of the present disclosure.
Figure 59:
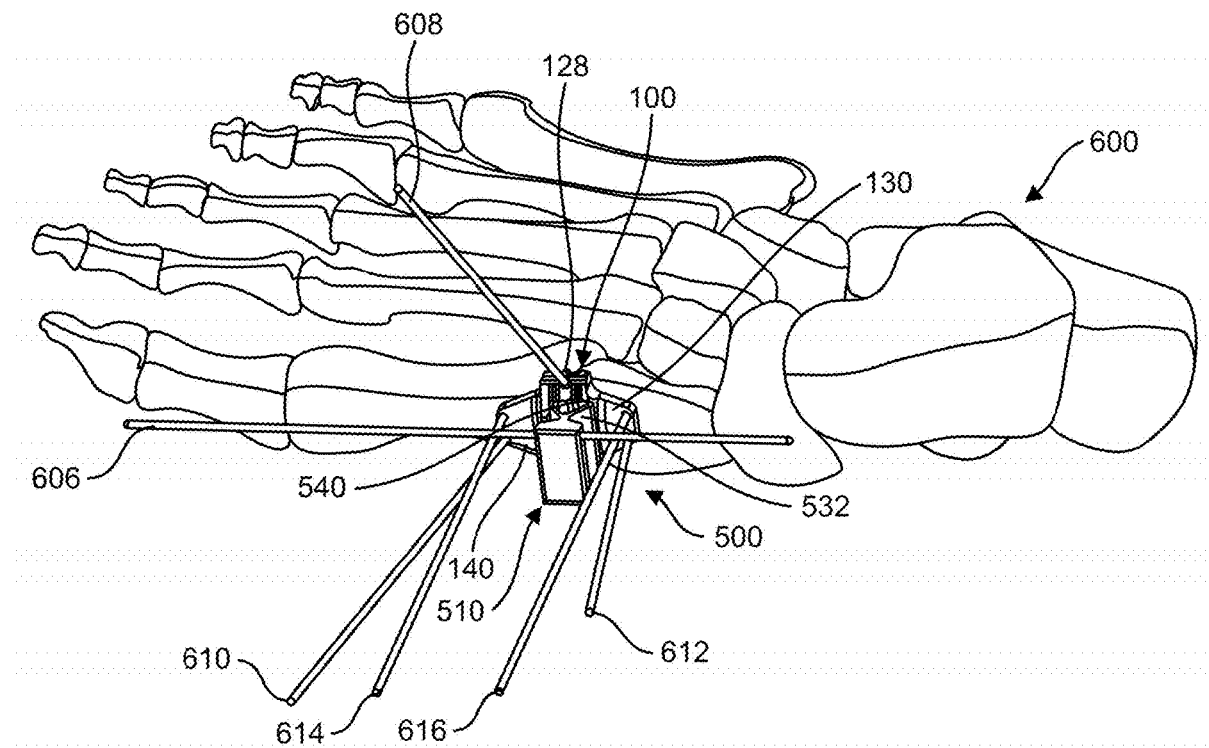
FIG. 59 is a top view of FIG. 57, in accordance with an aspect of the present disclosure.
Figure 64:
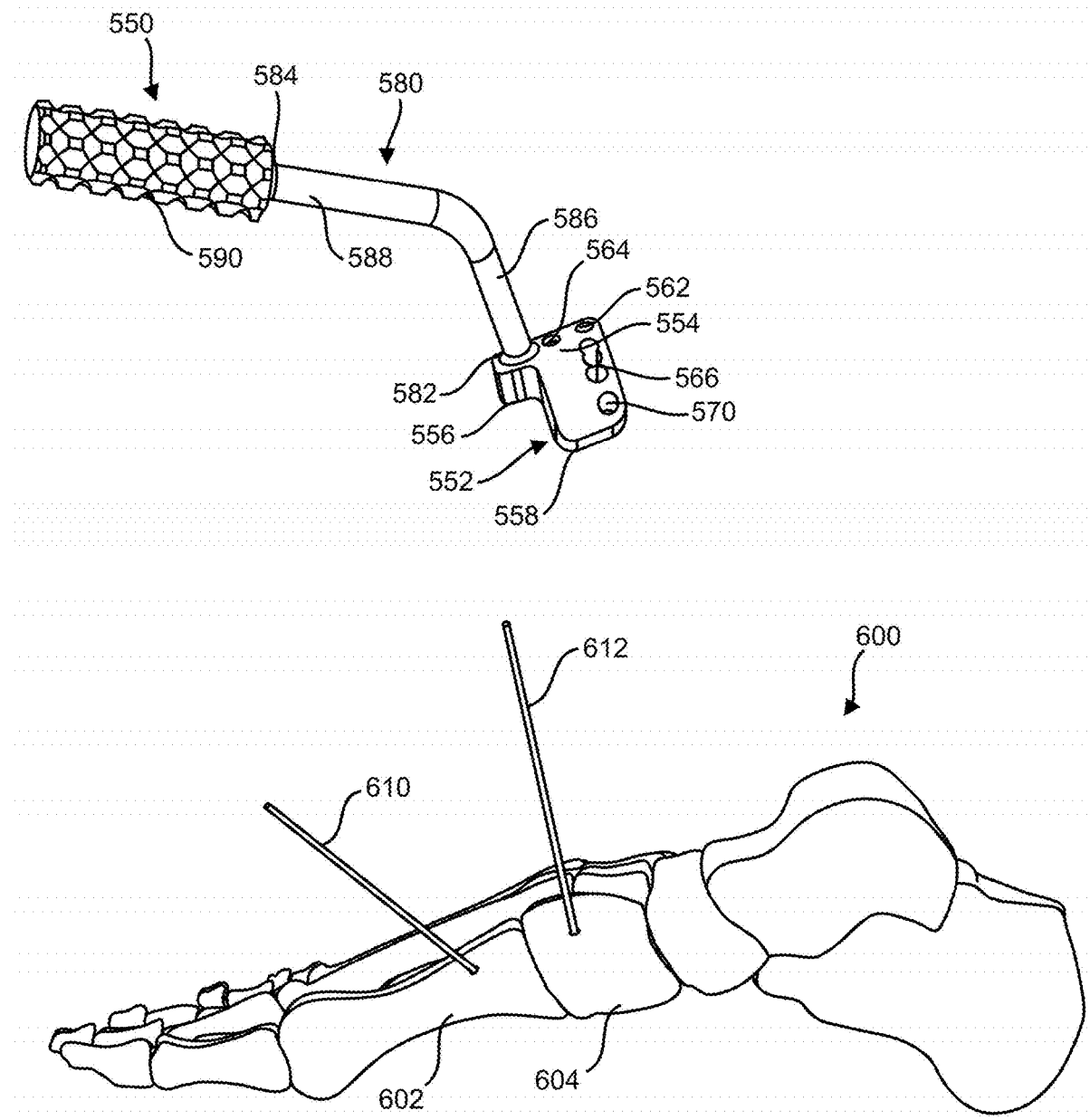
FIG. 64 is a partially exploded, side perspective view of the foot and two guide wires of FIG. 63 with a position rotation device being inserted onto at least one of the guide wires, in accordance with an aspect of the present disclosure.

Referring now to FIGS. 45 and 46, a guide system 500 is shown. The guide system 500 includes a cut guide 100, 150, 200, 250, 300, 350 and an alignment guide 510. The guide system 500 may also include the cut guide or revision cut guide 400. The guide system 500 may also include a position rotation device 550, as shown in FIG. 64. Further, the guide system 500 may include at least one directional wire 606 and at least two wires, guide wires, k-wires, or the like 608, 610, 612, 614, 616, as shown in FIGS. 57-59. In the depicted embodiment of FIGS. 45 and 46, the guide system 500 includes the cut guide 100 and the alignment guide 510. Although not shown, it is also contemplated that cut guides 150, 200, 250, 300, 350 may be interchangeable with cut guide 100 in the below described method or alternatively, used in conjunction with the cut guide 100 as described in greater detail below. The various embodiments of the cut guides 100, 150, 200, 250, 300, 350 are described in greater detail above and will not be described again here for brevity sake. As shown in FIGS. 45 and 46, the alignment guide 510 removably engages the cut guide 100. The alignment guide 510 may, for example, couple to at least one slot 116, 118, 120, 122 of the cut guide 100. In one embodiment, the alignment guide 510 couples to two slots 116, 118, 120, 122 and, for example, it is preferable that the alignment guide 510 couple to the two proximal slots 120, 122.

As shown in FIGS. 45-52, the alignment guide 510 includes a base portion 512 with a top surface 514, a bottom surface 516, a first end 518, a second end 520, a first side 522, and a second side 524. The a first end 518 may be, for example, a proximal end, a second end 520 may be, for example, a distal end, a first side 522 may be, for example, a medial side, and a second side 524 may be, for example, a lateral side. The base portion 512 may also include at least one opening 526, 528, 530 extending between the first end 518 and the second end 520. In the depicted embodiment, the base portion 512 includes a first opening 526 positioned near the first side 522, a third opening 530 positioned near the second side 524, and a second opening 528 positioned between the first opening 526 and the third opening 530, as shown in FIGS. 45-48 and 50. The openings 526, 528, 530 may be, for example, sized and shaped to receive a wire, guide wire, k-wire, directional wire, or the like, as shown in FIGS. 55-59.

The alignment guide 510 may also include a first extension member or leg member 532 extending away from a bottom surface 516 of the base portion 512, as shown in FIGS. 45, 47-49, 51, and 52. The first extension member 532 may include a first portion 534, a second portion 536 and a first engagement member 538. The first portion 534 may be coupled to the bottom surface 516 of the base portion 512 at a first end, extend away from a position near a center of the base portion 512 in the direction of the first end 518 at an angle, and be coupled to the second portion 536 at a second end. The first end of the second portion 536 may extend from the second end of the first portion 534 in a direction toward the second end 520 of the base portion 512 and be coupled to the first engagement member 538 at a second end. The first engagement member 538 may be coupled to the second portion 536 at a first end and extend in a plantar direction away from the second portion 536 to a second end. The second end of the first engagement member 538 may be shaped to engage the slots in a cut guide, for example, the slots 116, 118, 120, 122 of cut guide 100, as shown in FIGS. 45 and 46. The second end of the second engagement member 546 may also engage the slots of alternative cut guides, such as, cut guides 150, 200, 250, 300, 350.

The alignment guide 510 may also include a second extension member or leg member 540 extending away from a bottom surface 516 of the base portion 512, as shown in FIGS. 45, 47-49, 51, and 52. The second extension member 540 may include a third portion 542, a fourth portion 544 and a second engagement member 546. The third portion 542 may be coupled to the bottom surface 516 of the base portion 512 at a first end, extend away from a position near a center of the base portion 512 in the direction of the second end 520 at an angle, and be coupled to the fourth portion 544 at a second end. The first end of the second extension member 540 may also couple to or engage the first end of the first extension member 532. The first end of the fourth portion 544 may extend from the second end of the third portion 542 in a direction toward the first end 518 of the base portion 512 and be coupled to the second engagement member 546 at a second end. The second engagement member 546 may be coupled to the fourth portion 544 at a first end and extend in a plantar direction away from the fourth portion 544 to a second end. The second end of the second engagement member 546 may be shaped to engage slots in a cut guide, for example, the slots 116, 118, 120, 122 of cut guide 100, as shown in FIGS. 45 and 46. The second end of the second engagement member 546 may also engage the slots of alternative cut guides, such as, cut guides 150, 200, 250, 300, 350.

Referring now to FIGS. 45, 47-49, and 52, the first extension member 532 and second extension member 540 may be, for example, mirror images of each other as the members 532, 540 extend away from the bottom surface 516 of the base portion 512. The extension members 532, 540 may be shaped, for example, to form a triangular shape with the first portion 534 forming a first side, the third portion 542 forming a second side, and the second portion 536 and the fourth portion 544 together forming a third side. The shape of the extension members 532, 540 allows for the alignment guide 510 to be positioned with respect to a cut guide 100, 150, 200, 250, 300, 350 to create a visual depiction of the angle of deformity correction in both the dorsal and lateral planes. The first engagement member 538 may extend away from the second portion 536, for example, generally parallel to the second engagement member 546 as the second engagement member 546 extends away from the fourth portion 544. The engagement members 538, 546 may extend away from the second and fourth portions 536, 544, respectively, for example, generally perpendicular to the top surface 514 of the base portion 512. Alternatively, it is also contemplated that the engagement members 538, 546 may extend, for example, away from the second and fourth portions 536, 544, respectively, at an angle with respect to the top surface 514 of the base portion 512. The extension members 532, 540 may act to create, for example, a spring like mechanism in the engagement members 538, 546 to allow the engagement members 538, 546 to couple to the cut guides 100, 150, 200, 250, 300, 350.

Figure 65:
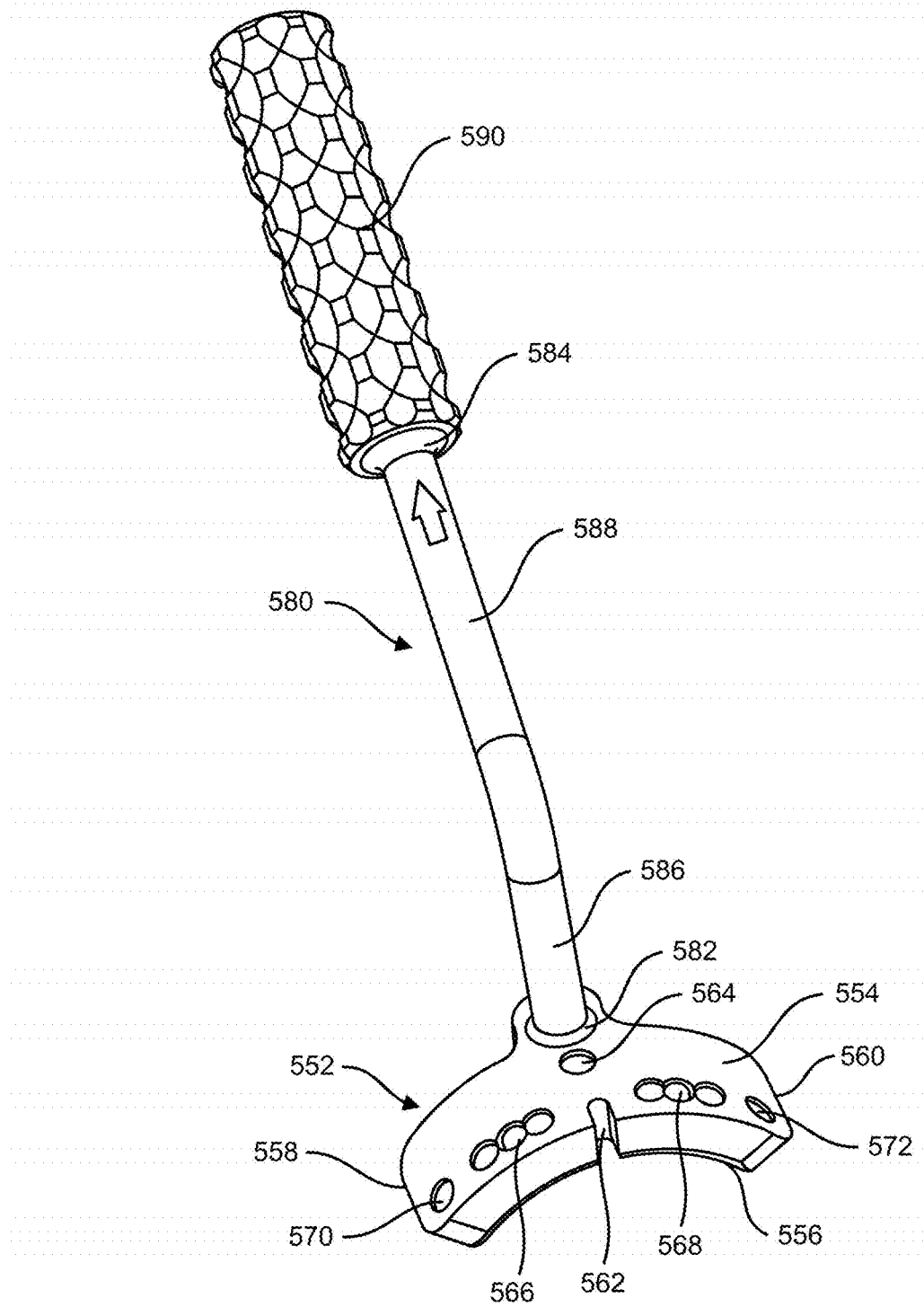
FIG. 65 is a front perspective view of the position rotation device, in accordance with an aspect of the present disclosure.
Figure 66:
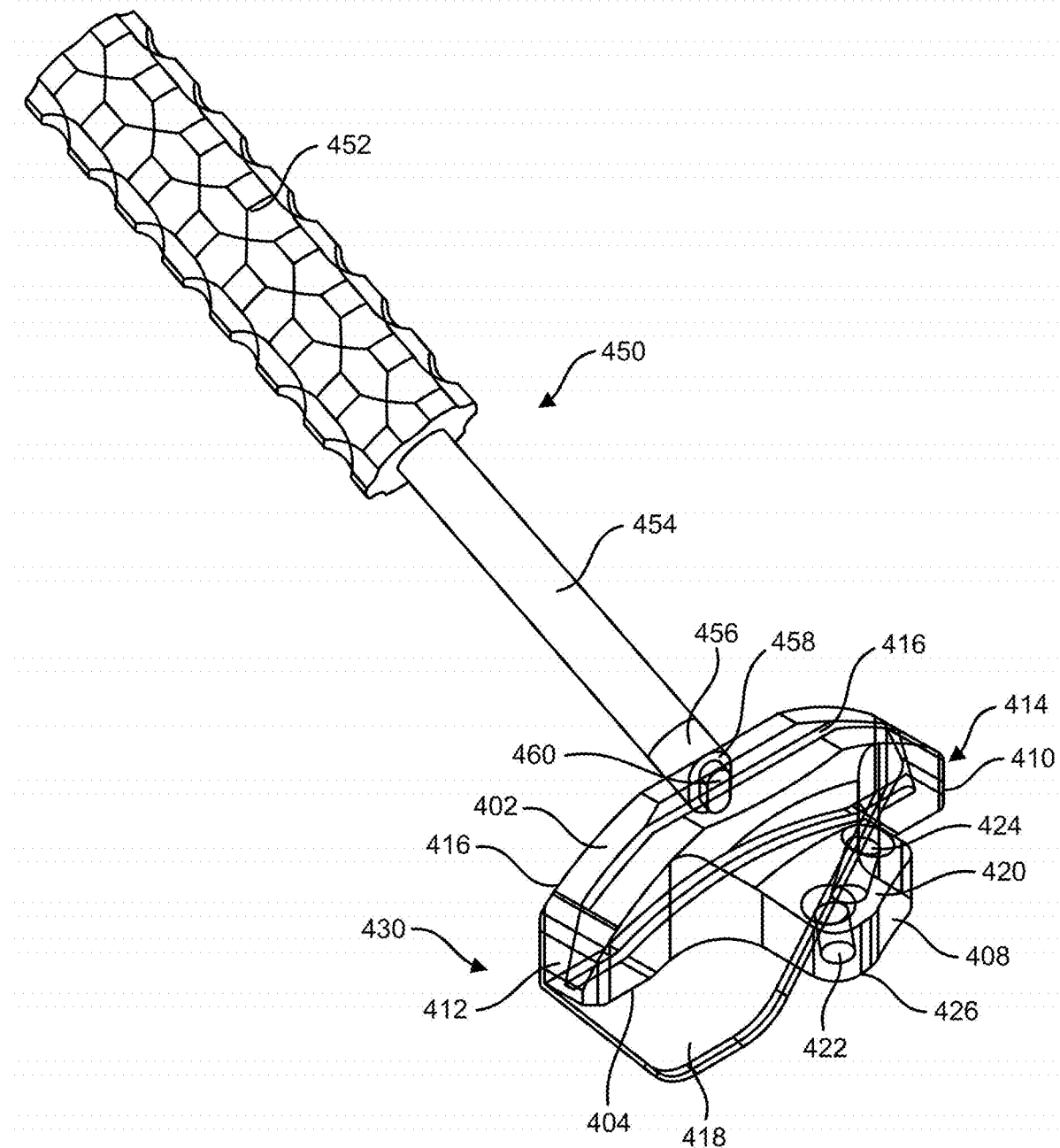
FIG. 66 is a top perspective view of an embodiment of a cut guide system including a transparent cut guide and insertion handle, in accordance with an aspect of the present disclosure.
Figure 67:
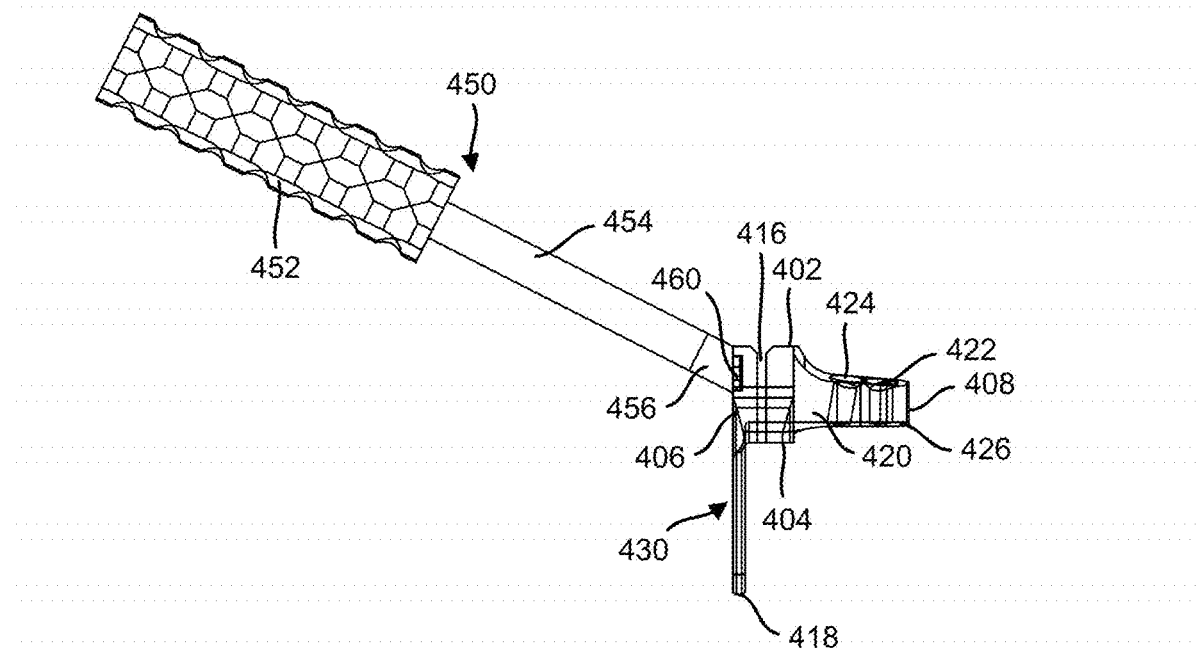
FIG. 67 is a side view of the cut guide system of FIG. 66, in accordance with an aspect of the present disclosure.
Figure 68:
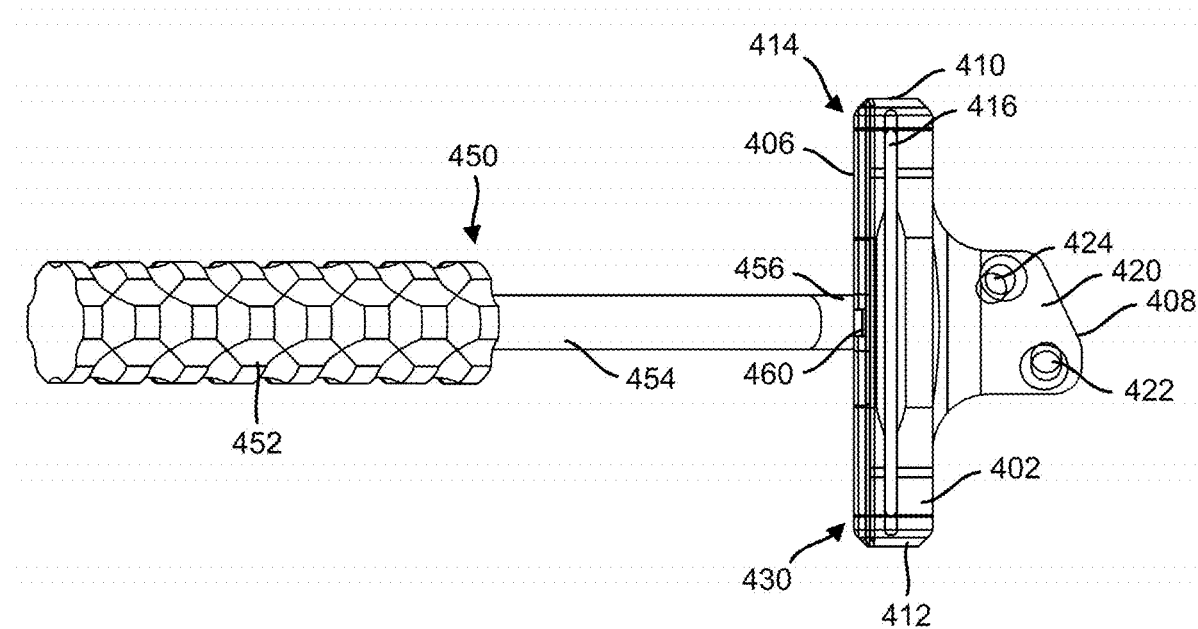
FIG. 68 is a top view of the cut guide system of FIG. 66, in accordance with an aspect of the present disclosure.
Figure 69:
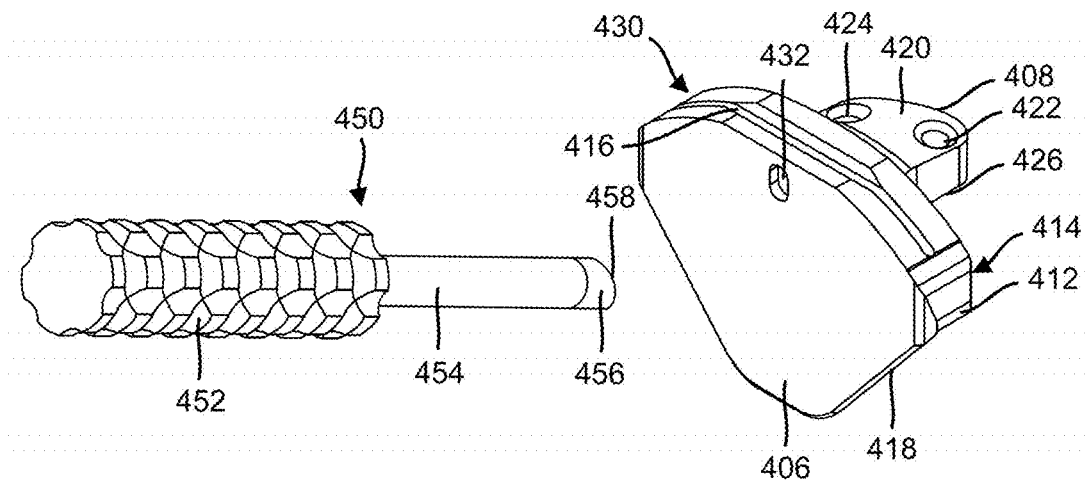
FIG. 69 is an exploded, first end perspective view of the cut guide system of FIG. 66 with a solid cut guide, in accordance with an aspect of the present disclosure.
Figure 70:
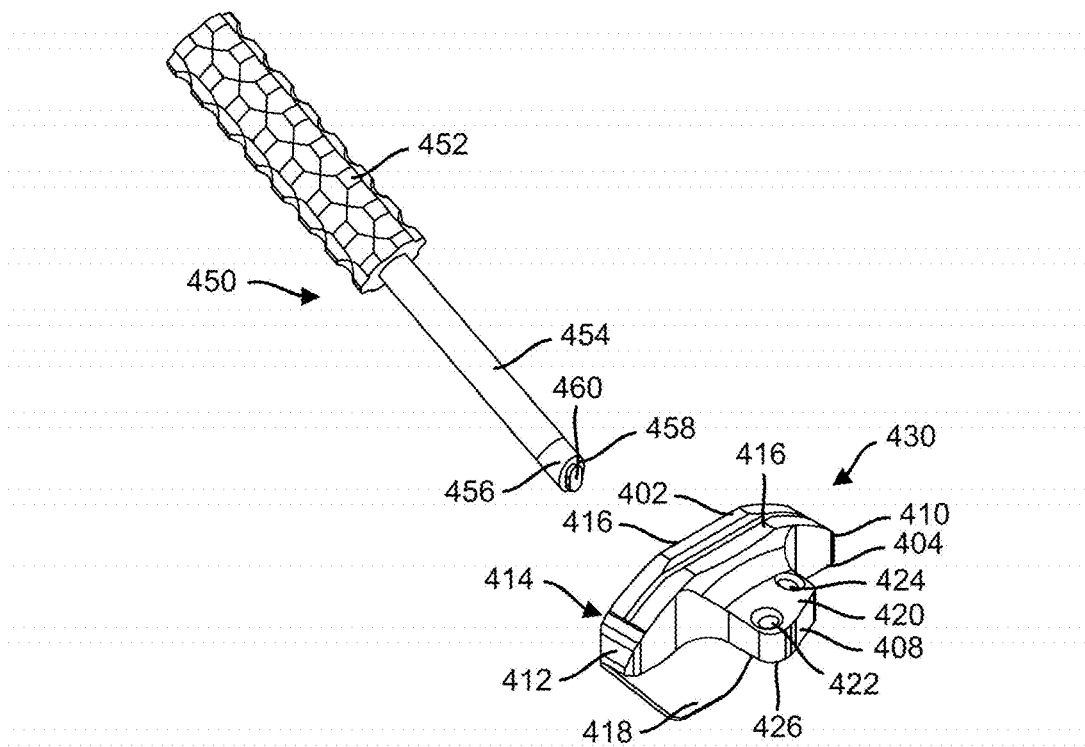
FIG. 70 is an exploded, second end perspective view of the cut guide system of FIG. 69, in accordance with an aspect of the present disclosure.
Figure 72:
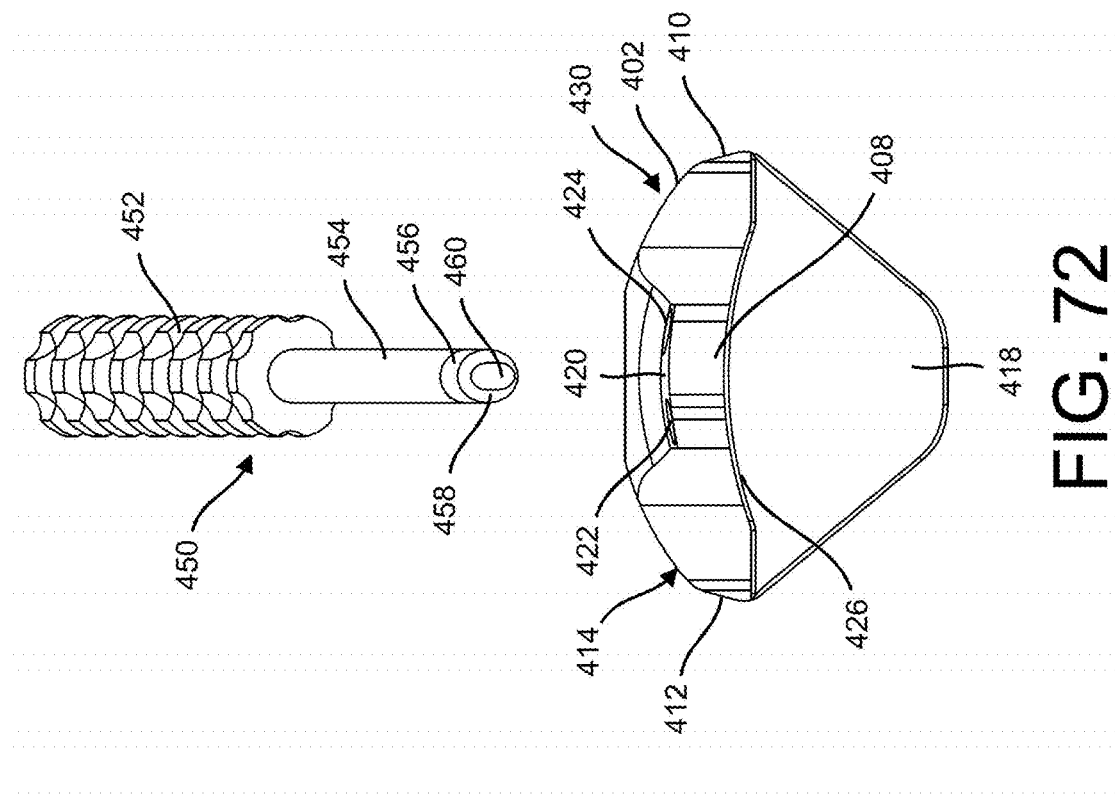
FIG. 72 is an exploded second end view of the cut guide system of FIG. 69, in accordance with an aspect of the present disclosure.
Figure 71:
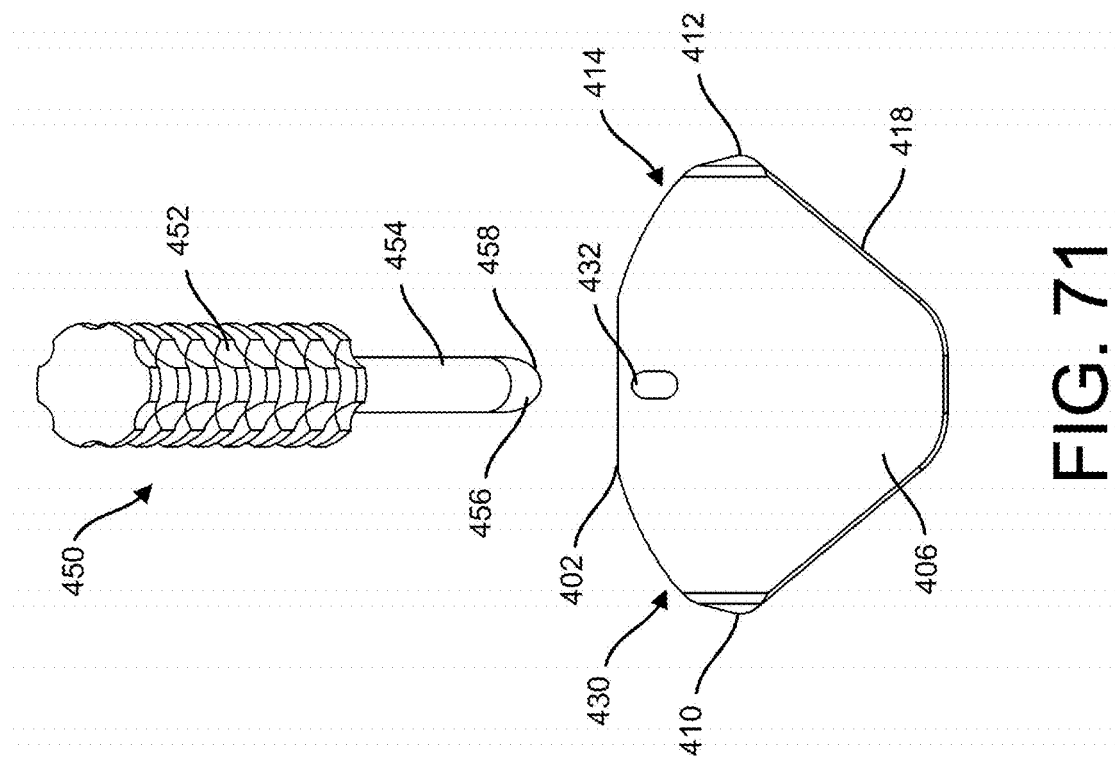
FIG. 71 is an exploded first end view of the cut guide system of FIG. 69, in accordance with an aspect of the present disclosure.
Figure 73:
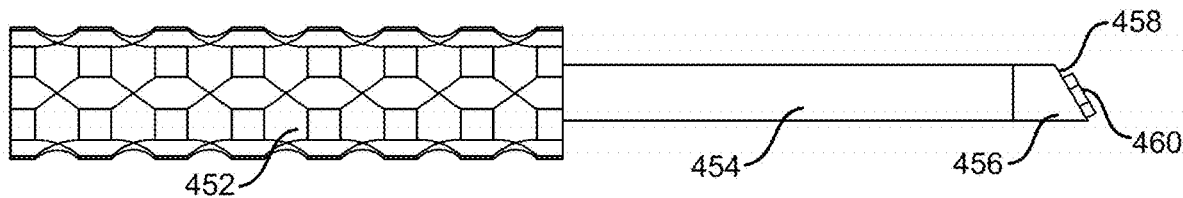
FIG. 73 is a side view of the insertion handle of FIG. 66, in accordance with an aspect of the present disclosure.
Figure 74:
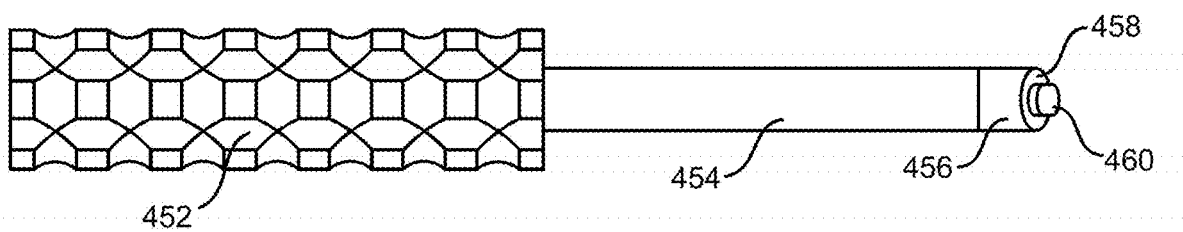
FIG. 74 is a top view of the insertion handle of FIG. 66, in accordance with an aspect of the present disclosure.

The position rotation device 550 is shown in FIGS. 64 and 65. The rotation device includes a base 552 with a top surface 554 opposite a bottom surface 556. The base 552 also includes a first end 558 opposite a second end 560. The base 552 may be, for example, curved to form a semi-circle or arc as the base 552 extends from the first end 558 to the second end 560. The base 552 may also optionally include a center alignment groove 562. The alignment groove 562 may be inset into a front side of the base 552 and may extend from the top surface 554 through the base 552 to the bottom surface 556.

With continued reference to FIGS. 64 and 65, the base 552 further includes a first or zero opening 564 positioned, for example, centered between the first end 558 and the second end 560 of the base 552. The zero opening 564 may be positioned adjacent to the first end 582 of the shaft 580. The zero opening 564 may also be positioned, for example, near a back side of the base 552. The zero opening 564 may have, for example, an insertion angle for a guide wire, k-wire or the like of 0° as the opening 564 extends from the top surface 554 to the bottom surface 556. The zero opening 564 may be used for positioning and aligning the position rotation device 550 on a patient. The zero opening 564 may be, for example, sized and shaped or configured to receive a guide wire, k-wire or the like, for aligning the rotation device 550 on a patient's bone.

As shown in FIGS. 64 and 65, the base 552 may also include a first set of overlapping openings 566. The openings 566 may be positioned along the front side of the rotation device 550 between the groove 562 and the first end 558. The base 552 may also include a second set of overlapping openings 568. The openings 568 may be positioned along the front side of the rotation device 550 between the groove 562 and the second end 560. The base 552 may also include a third opening 570 positioned along the front side of the rotation device 550 between the first set of openings 566 and the first end 558. The base 552 may also include a fourth opening 572 positioned along the front side of the rotation device 550 between the second set of openings 568 and the second end 560. The openings 566, 568, 570, 572 may be, for example, angled as they extend from the top surface 554 to the bottom surface 556. The first set of overlapping openings 566 and the second set of overlapping openings 568 may each include, for example, three openings. The three overlapping openings 566, 568 may each have an angle of rotation relative to the zero opening 564, for example, the openings 566, 568 closest to the groove 562 may have a rotation angle of approximately 10° to 19°. The next openings 566, 568 may have a rotation angle of, for example, approximately 20° to 29° and the outer most opening 566, 568 from the groove 562 may have a rotation angle of, for example, approximately 30° to 39°. Finally, the third and fourth openings 570, 572 may have rotation angles relative to the zero opening 564 of, for example, approximately 40° to 50°. In one embodiment, the rotation angles may be, for example, 15°, 25°, 35°, and 45°. In yet another embodiment, the rotation angles may be, for example, 15°, 22°, 30°, and 45°. The openings 566, 568, 570, 572 may be positioned linearly along the base 552 as it curves from the first end 558 to the second end 560 and offset from the zero opening 564. Alternatively, each of the openings 566, 568, 570, 572 may be, for example, offset from each other and the zero opening 564.

Referring now to FIGS. 53-64, a method of using the guide system 500 is shown. As shown in FIGS. 53-63, the guide system 500 may include the cut guide 100, the alignment guide 510, the position rotation device 550, at least one directional wire 606, and multiple guide wires 608, 610, 612, 614, 616. Although FIGS. 53-63 show the method using the cut guide 100, it is also contemplated that the method may include using any one of cut guides 100, 150, 200, 250, 700, 750, 800, 850, 900, 950. Alternatively, the method may include using a combination of one of cut guides 300, 350, 1000, 1050 on the first metatarsal and then any one of cut guides 100, 150, 200, 250, 700, 750, 800, 850, 900, 950 on the cuneiform.

Figure 53:
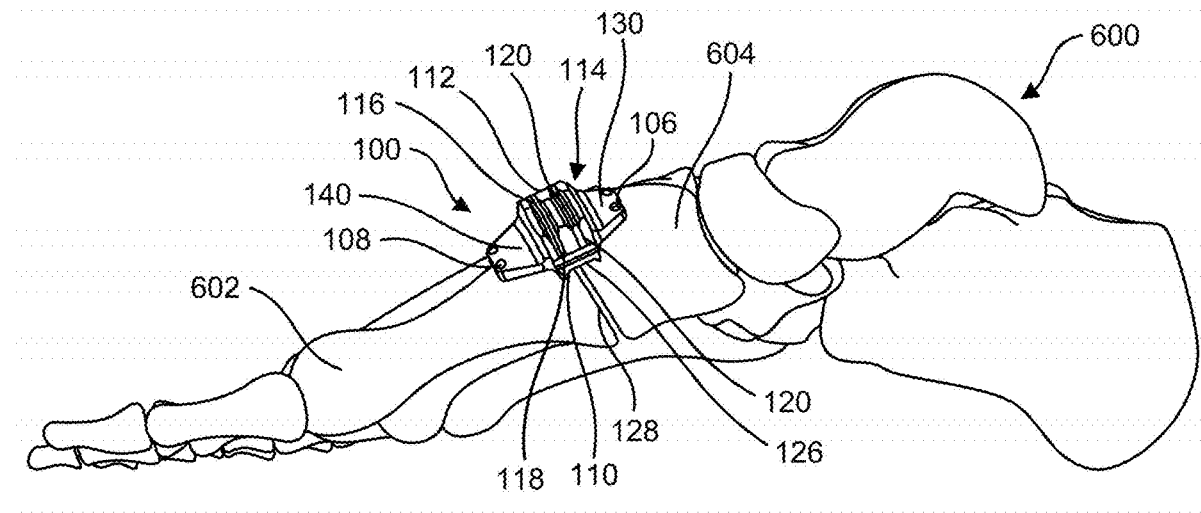
FIG. 53 is a side perspective view of the cut guide of FIG. 1 inserted into a foot, in accordance with an aspect of the present disclosure.
Figure 54:
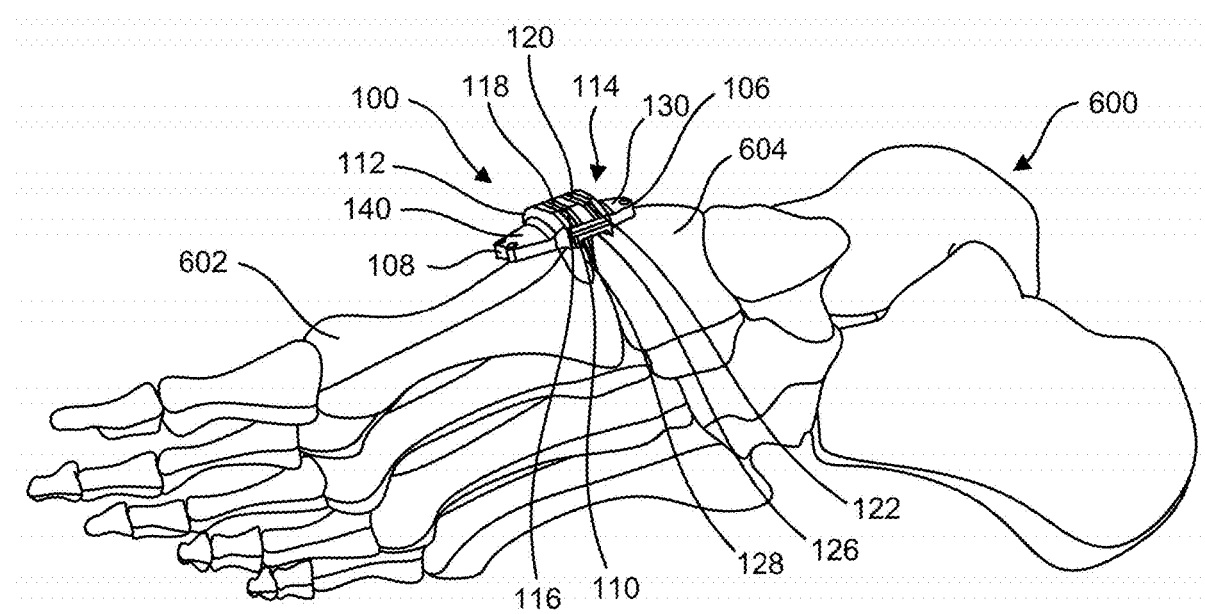
FIG. 54 is a bottom, side perspective view of the cut guide and foot of FIG. 53, in accordance with an aspect of the present disclosure.

The method may include inserting the extension member 128 of the cut guide 100 into the joint space between a first bone or first metatarsal 602 and a second bone or medial cuneiform 604, as shown in FIGS. 53 and 54. The extension member 128 fits between the first bone 602 and second bone 604 to align the slots 116, 118, 120, 122 of the base portion 114 to produce the desired angled cut. The slots 116, 118, 120, 122 may be angled relative to the extension member 128 to account for the extension member 128 shifting during resection of the bone. The extension member 128 may be inserted so that the first arm 130 is positioned on the second bone 604 and the second arm 140 is positioned on the first bone 602.

Figure 55:
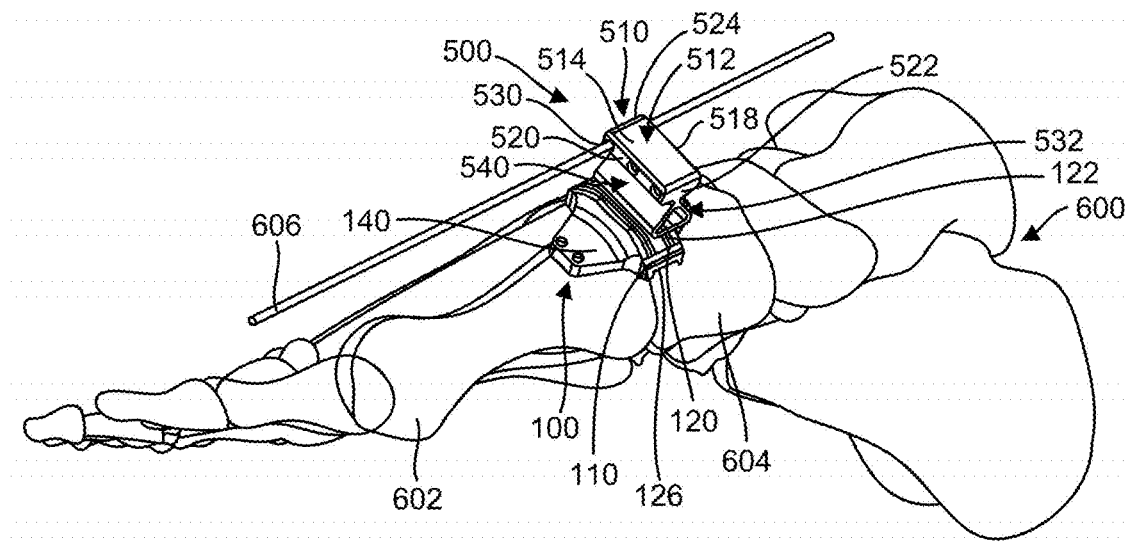
FIG. 55 is a side perspective view of the foot and cut guide of FIG. 53 with the alignment guide of FIG. 47 inserted into the cut guide and a directional wire inserted into the alignment guide, in accordance with an aspect of the present disclosure.
Figure 56:
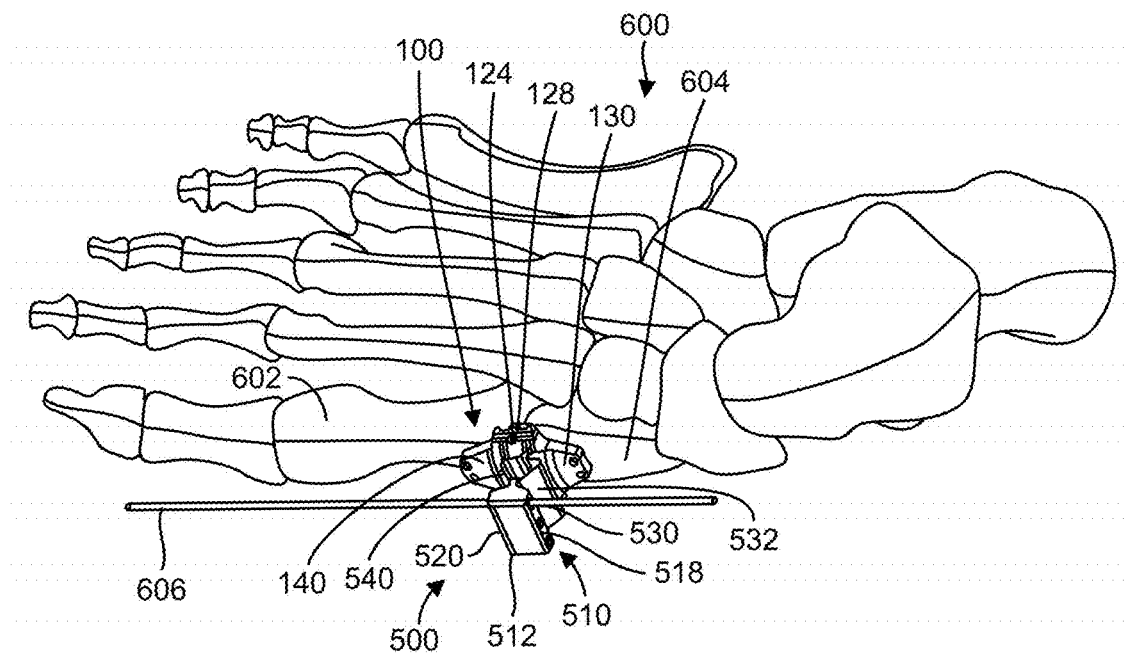
FIG. 56 is a top perspective view of FIG. 55, in accordance with an aspect of the present disclosure.

Next, the alignment guide 510 may be coupled to the cut guide 100, as shown in FIGS. 55 and 56. The first engagement member 538 may be, for example, inserted into a first slot 120, 122 and the second engagement member 546 may be, for example, inserted into a second slot 120, 122. For example, as shown in FIGS. 55 and 56, the first engagement member 538 may be inserted in the slot 120 and the second engagement member 546 may be inserted into the slot 122. The method may also include inserting at least one directional wire 606 into at least one opening 526, 528, 530 in the alignment guide 510. As further shown in FIGS. 55 and 56, a directional wire 606 is inserted into the opening 530 in the alignment guide 510. The directional wire 606 inserted into the alignment guide 510 depicts the exact angle of deformity correction in both the dorsal and lateral planes. The mating of the engagement members 538, 546 and the slots 120, 122 produces the resulting angle of correction and illustrates the correction angle during surgery.

After inserting a direction wire 606 into the alignment guide 510, the method may optionally include changing the cut guide 100 to a cut guide with a different angular size. For example, if the alignment guide 510 shows an over-correction or under-correction of the hallux valgus deformity, then the surgeon may go down or up an angular size of cut guide, respectively. Each of the cut guides 100, 150, 200, 250, 300, 350, 700, 750, 800, 850, 900, 950, 1000, 1050 may have different angular sizes and/or be for a right or left foot. If the alignment guide 510 shows an over-correction or under-correction, then the cut guide 100 may be removed from the foot 600 and replaced with an alternative size cut guide 150, 200, 250, 300, 350. If the cut guide 700, 750 is used, then the cut guide 700, 750 may be removed from the foot 600 and replaced with an alternative size cut guide 800, 850, 900, 950, 1000, 1050. Once the new cut guide is inserted into the foot 600, the surgeon may re-check the correction by inserting the alignment guide 510 into the new cut guide and the directional wire 606 into the alignment guide 510, as described in greater detail above, to determine whether the new cut guide provides the desired correction.

Once the cut guide 100, 150, 200, 250, 300, 350, 700, 750, 800, 850, 900, 950, 1000, 1050 with the desired correction is inserted into the patient's joint space, then a k-wire, guide wire or dorsal wire 608 may be inserted into the dorsal hole 124 of the cut guide 100 between the slot 118 and the slot 120, as shown in FIGS. 57-59. The guide wire 608 may be used to check the orientation of the cut guide 100 by checking that the wire 608 is parallel to a patient's tibia and perpendicular to the weight-bearing surface. After the desired orientation is achieved, k-wires, guide wires, wires 610, 612, 614, 616 may be inserted through the holes 132, 134, 142, 144 in the cut guide 100 and into the bones 602, 604, to secure the cut guide 100 to the bones 602, 604, as shown in FIGS. 57-59. For example, a distal-medial wire, k-wire, guide wire 610 may be inserted into the fourth opening 144 in the cut guide 100, a proximal-medial wire, k-wire, guide wire 612 may be inserted into the second opening 134, a distal-lateral wire, k-wire, guide wire 614 may be inserted into the third opening 142, and a proximal-lateral wire, k-wire, guide wire 616 may be inserted into the first opening 132, as shown in FIGS. 57-59.

Figure 60:
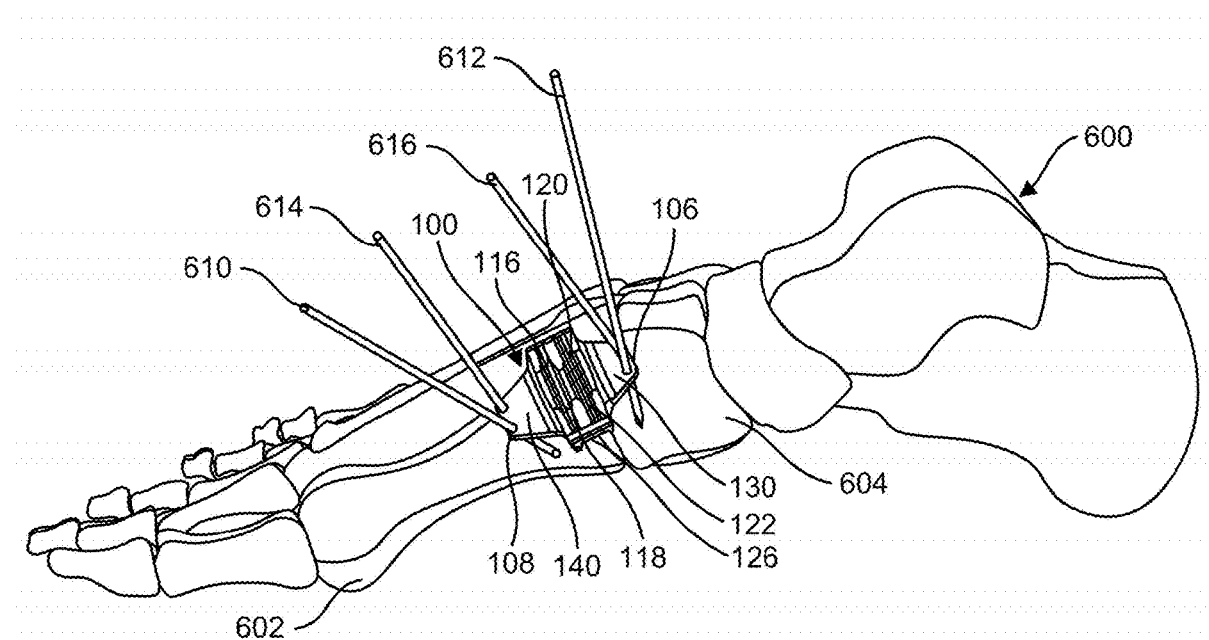
FIG. 60 is a side view of FIGS. 57-59 after removal of the directional wire, the alignment guide, and the lateral guide wire, in accordance with an aspect of the present disclosure.
Figure 61:
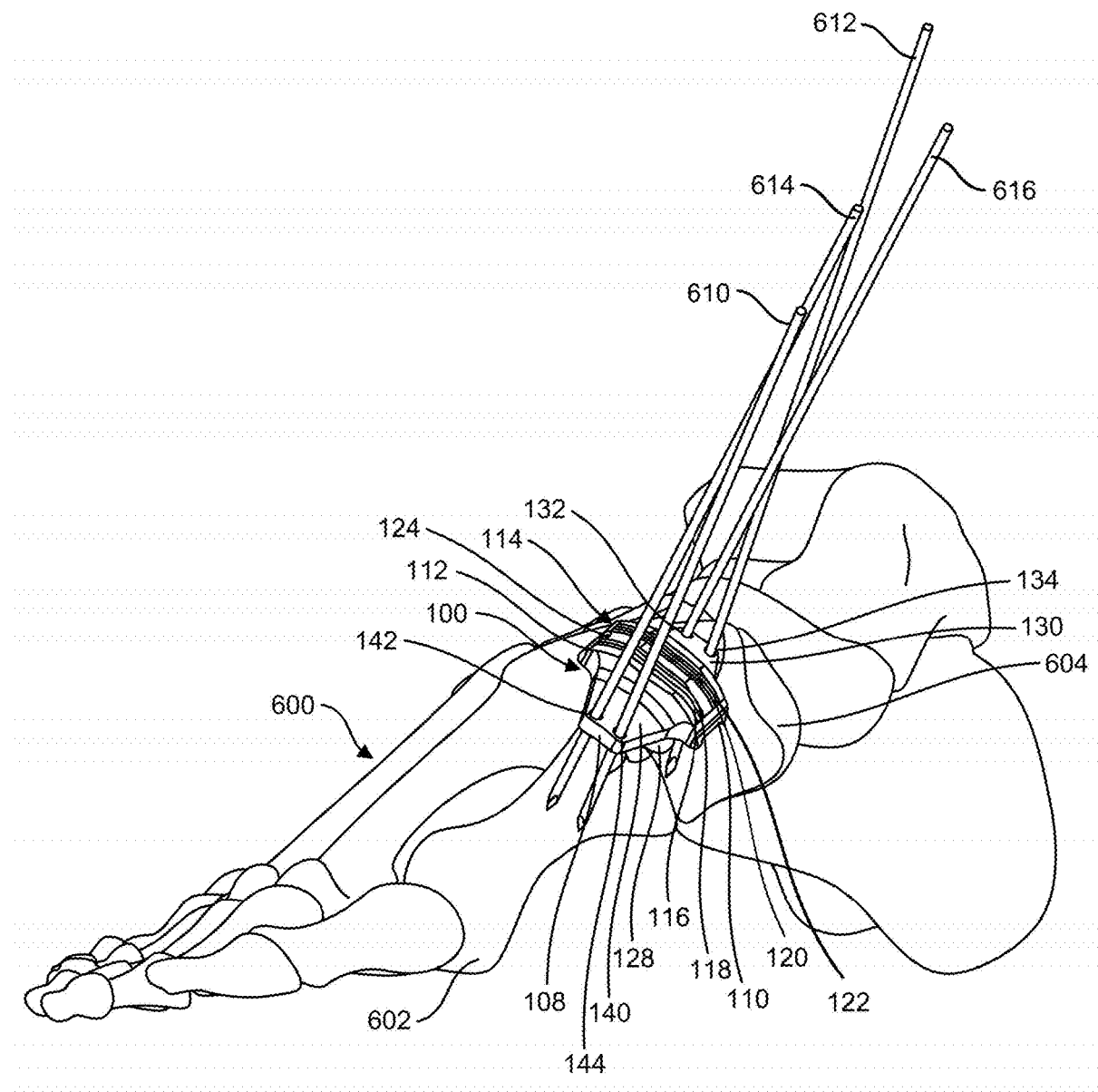
FIG. 61 is a first end, perspective view of FIG. 60, in accordance with an aspect of the present disclosure.
Figure 62:
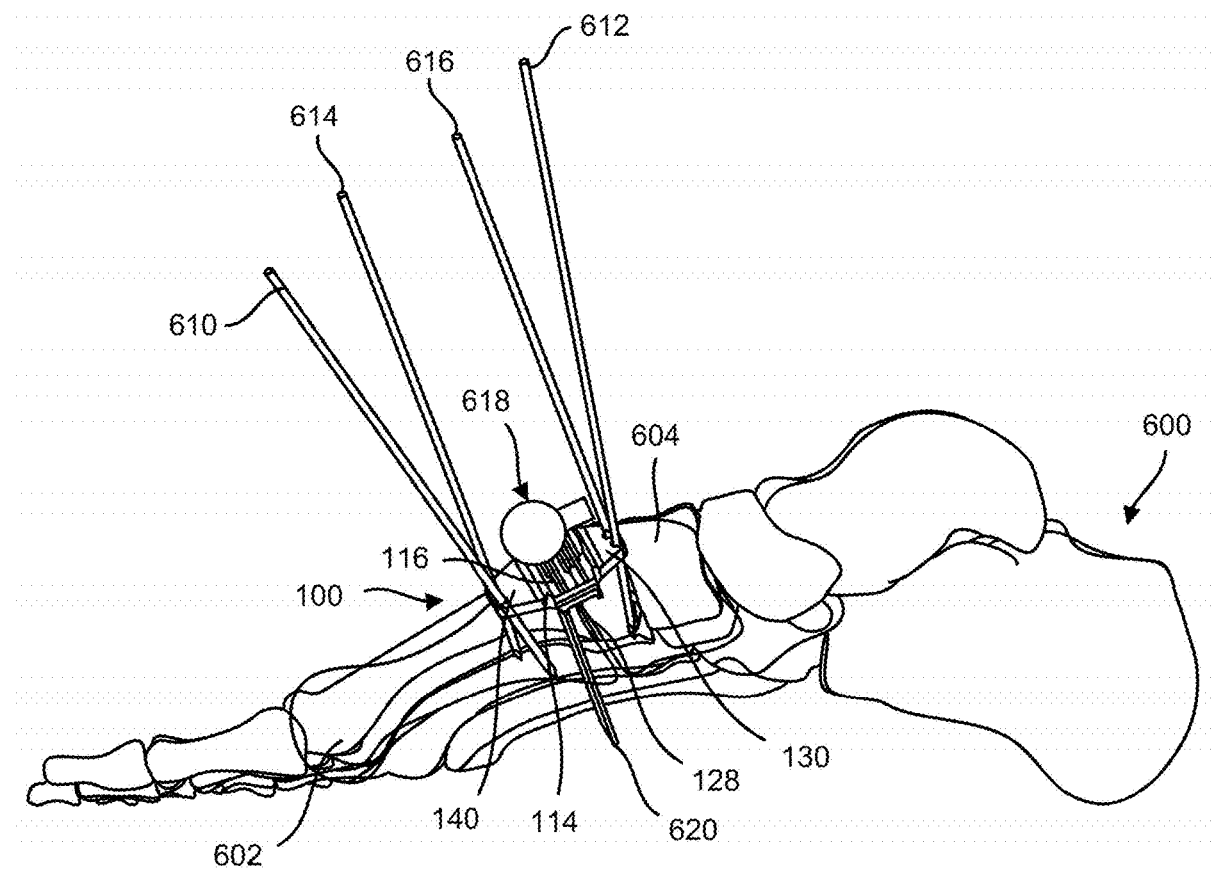
FIG. 62 is a perspective, side view of the foot, cut guide and guide wires of FIGS. 60 and 61 with a saw blade inserted into a first slot of the cut guide, in accordance with an aspect of the present disclosure.
Figure 63:
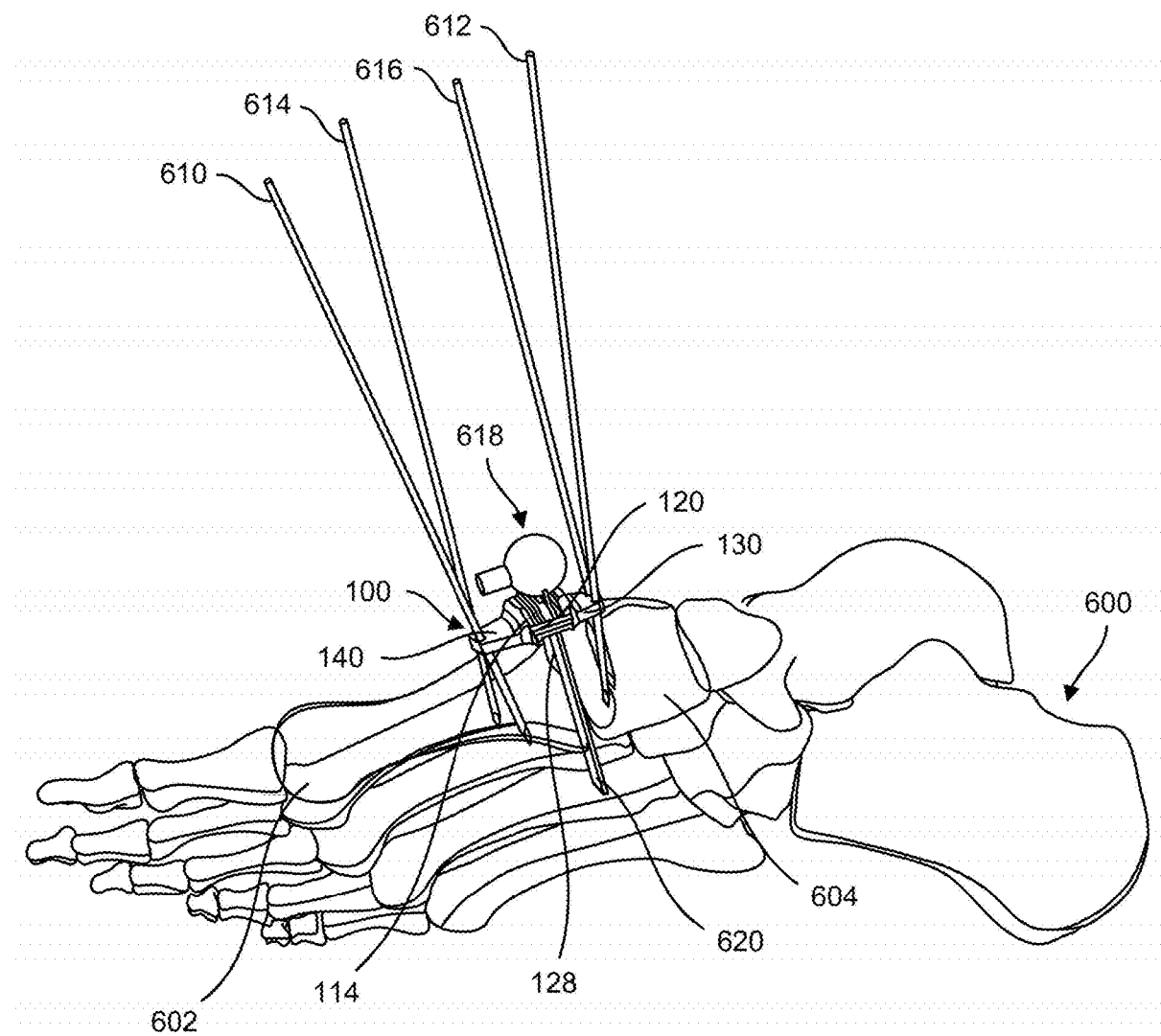
FIG. 63 is a side, perspective view of the foot, cut guide, and guide wires of FIG. 62 with the saw blade inserted into a second slot of the cut guide, in accordance with an aspect of the present disclosure.

Next, the dorsal k-wire 608 and the alignment guide 510 may be removed from the cut guide 100, as shown in FIGS. 60 and 61. After the cut guide 100 is coupled to the bones 602, 604 and the alignment guide 510 and dorsal k-wire 608 are removed from the cut guide 100, the bones 602, 604 may be cut using the desired slots 116, 118, 120, 122, as shown in FIGS. 62 and 63. For example, a saw blade 620 of saw 618 may be inserted through the first slot 116 to cut the first bone 602, as shown in FIG. 62, then the saw blade 620 may be removed and inserted through the third slot 120 to cut the second bone 604, as shown in FIG. 63. After the bones 602, 604 are cut, the lateral k-wires 614, 616 and the cut guide 100 may be removed from the bones 602, 604 and the medial k-wires 610, 612 may be left in the bones 602, 604, as shown in FIG. 64. The medial k-wires 610, 612 may be positioned, for example, parallel to each other. If the angle of correction is not accurate the surgeon may insert another cut guide 200, 250, 300 over the medial k-wires 610, 612 and perform additional cutting to achieve the desired angle of correction. Alternatively or additionally, if more tissue or bone needs to be removed from the patient's bones, then the cut guide 400 may be inserted over one of the medial k-wires 610, 612. The cut guide 400 may then be positioned to align the extension member 418 against the cut surface of the bone to remove additional tissue or bone parallel to the original cut.

Once the desired amount of tissue and/or bone is removed and the desired angle of correction achieved, a position rotation device 550 may be slid over the medial k-wires 610, 612. The cartilage and bone that was resected using the cut guide 100 may also be removed from the joint, as shown in FIG. 64.

After the bones 602, 604 have been cut and the resected bone and cartilage removed, the rotation device 550 may be inserted over the distal-medial wire 610, as shown in FIG. 64. The wire 610 may be inserted into the first opening 564 of the rotation device 550. Then, a second k-wire (not shown) may be inserted into one of the openings 566, 568, 570, 572 corresponding to the desired angulation correction. After the second k-wire (not shown) is inserted through the selected opening 566, 568, 570, 572, the distal-medial wire 610 may be removed from the bone 602 and the rotation device 550. Next, the rotation device 550 may be removed from the foot 600. Then, the method may include rotating the bones 602, 604 to the desired correction where the second k-wire (not shown) in the first metatarsal 602 is positioned parallel to the k-wire 612 in the medial cuneiform 604 and temporarily securing the bones 602, 604 in the rotated position. Finally, the bones 602, 604 may be secured in the rotated position using a plate (not shown) and screws (not shown). Finally, the surgical procedure may include performing incision closure or concomitant procedures.

Referring now to FIGS. 75-82, another cut guide 700 is shown. The cut guide 700 includes a top surface 702, a bottom surface 704, a first or proximal end 706, a second or distal end 708, a first or medial side 710, and a second or lateral side 712. The cut guide 700 also includes a base portion 714 and a paddle, fin or extension member 728 extending away from the bottom surface 704 of the base portion 714. The cut guide 700 further includes a first or proximal arm 730 extending away from the base portion 714 on a first end 706 and a second or distal arm 740 extending away from the base portion 714 on a second end 708. The cut guide 700 may be, for example, a right foot cut guide.

Figure 75:
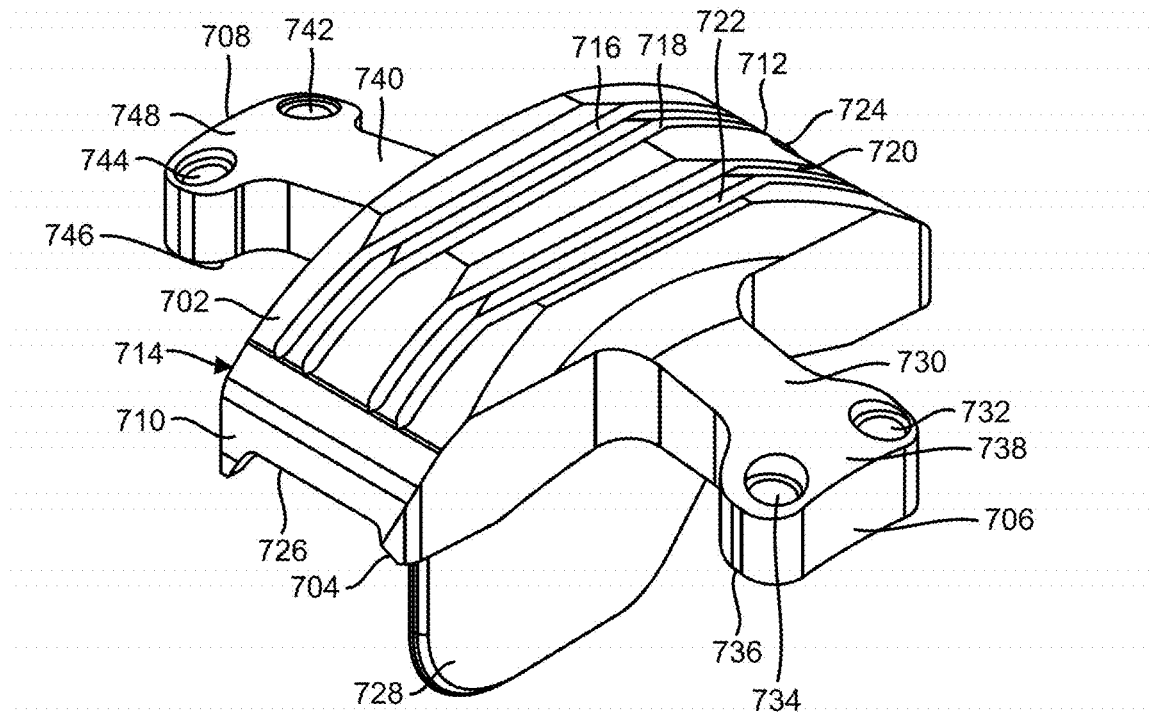
FIG. 75 is a top perspective view of an embodiment of a cut guide, in accordance with an aspect of the present disclosure.
Figure 76:
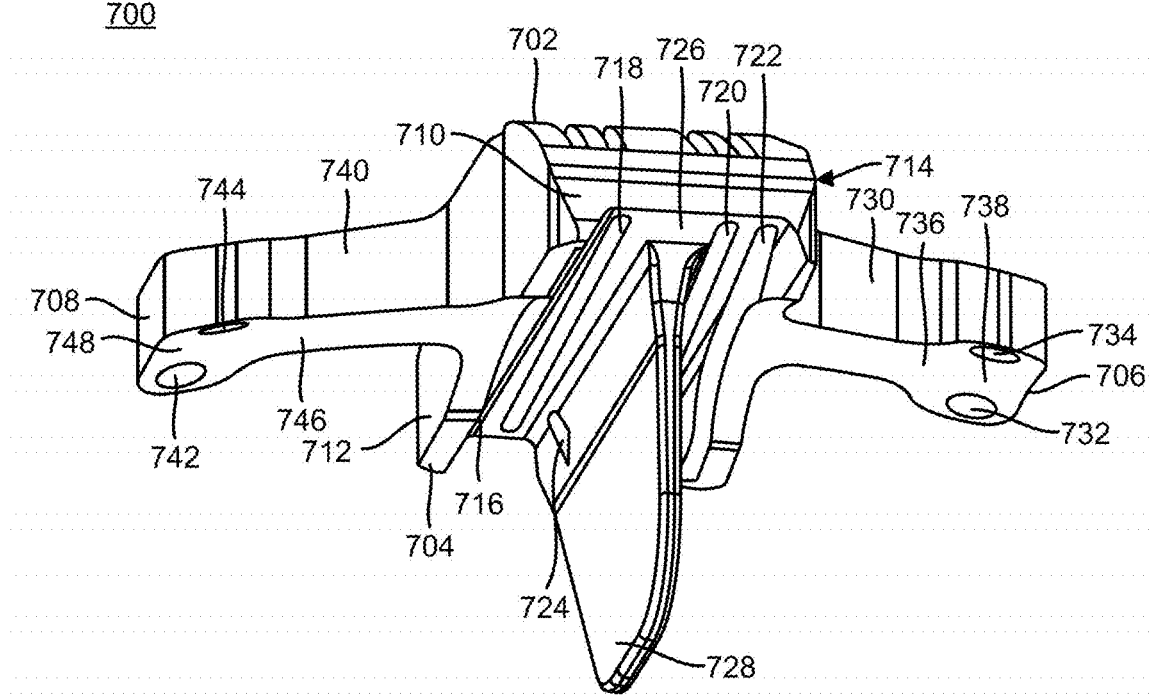
FIG. 76 is a bottom perspective view of the cut guide of FIG. 75, in accordance with an aspect of the present disclosure.
Figure 77:
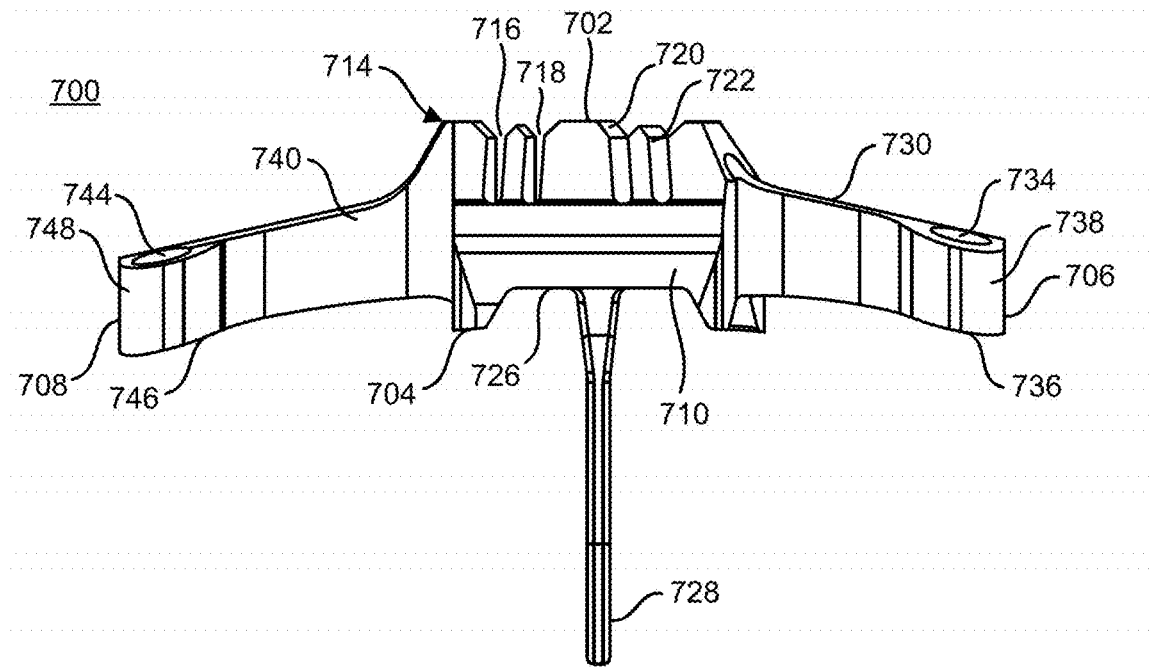
FIG. 77 is a side view of the cut guide of FIG. 75, in accordance with an aspect of the present disclosure.
Figure 78:
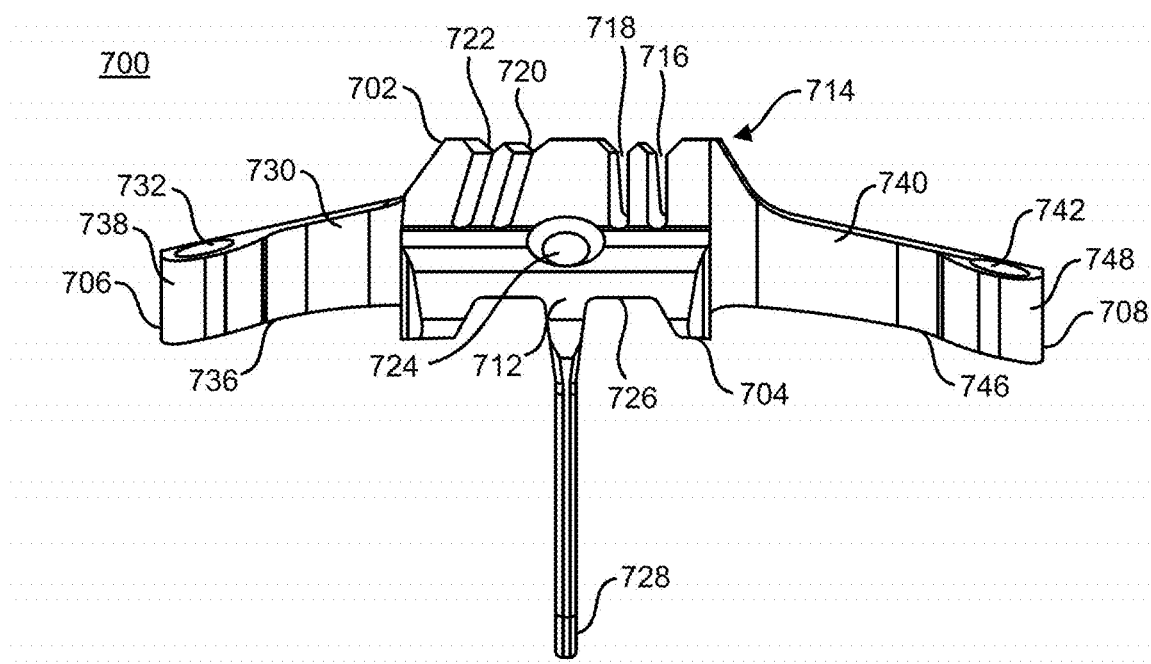
FIG. 78 is another side view of the cut guide of FIG. 75, in accordance with an aspect of the present disclosure.
Figure 79:
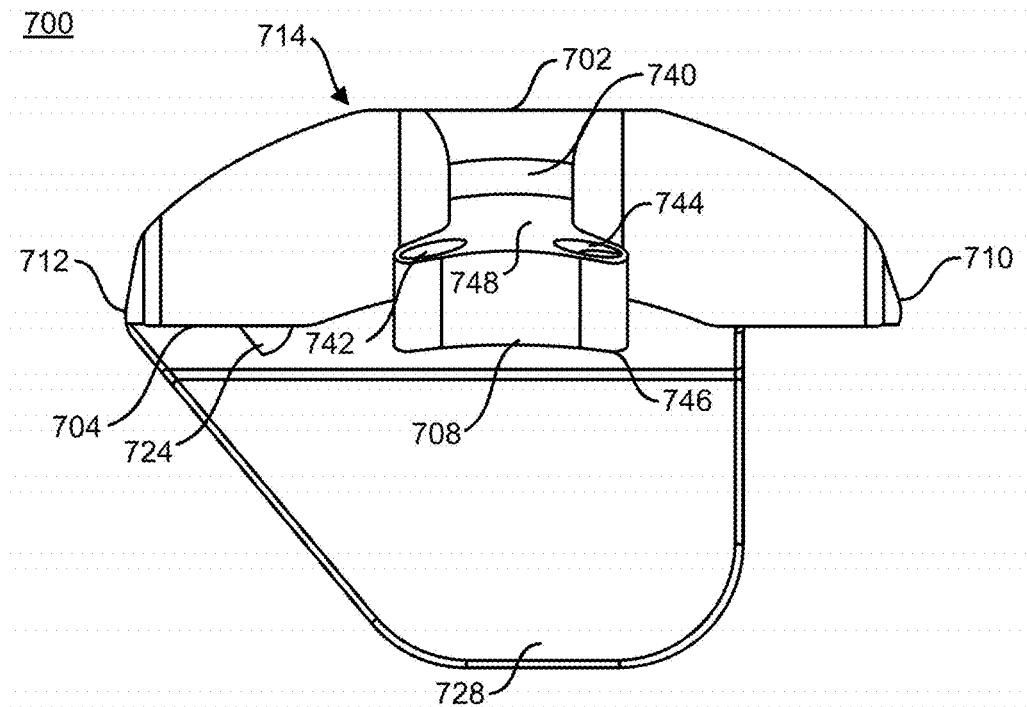
FIG. 79 is an end view of the cut guide of FIG. 75, in accordance with an aspect of the present disclosure.
Figure 80:
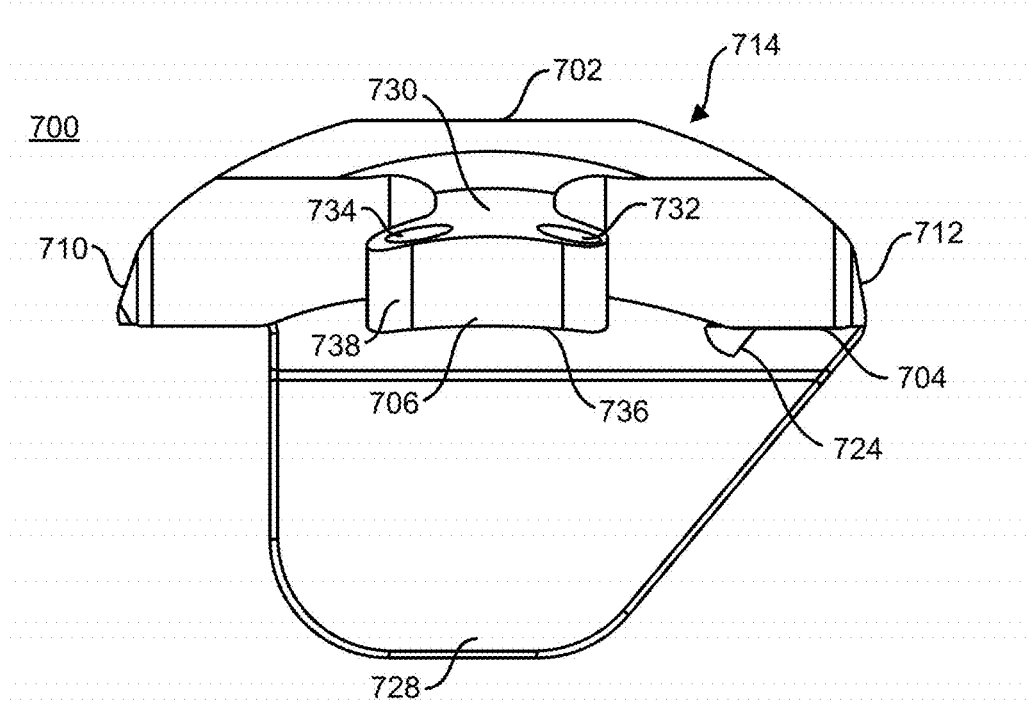
FIG. 80 is another end view of the cut guide of FIG. 75, in accordance with an aspect of the present disclosure.
Figure 81:
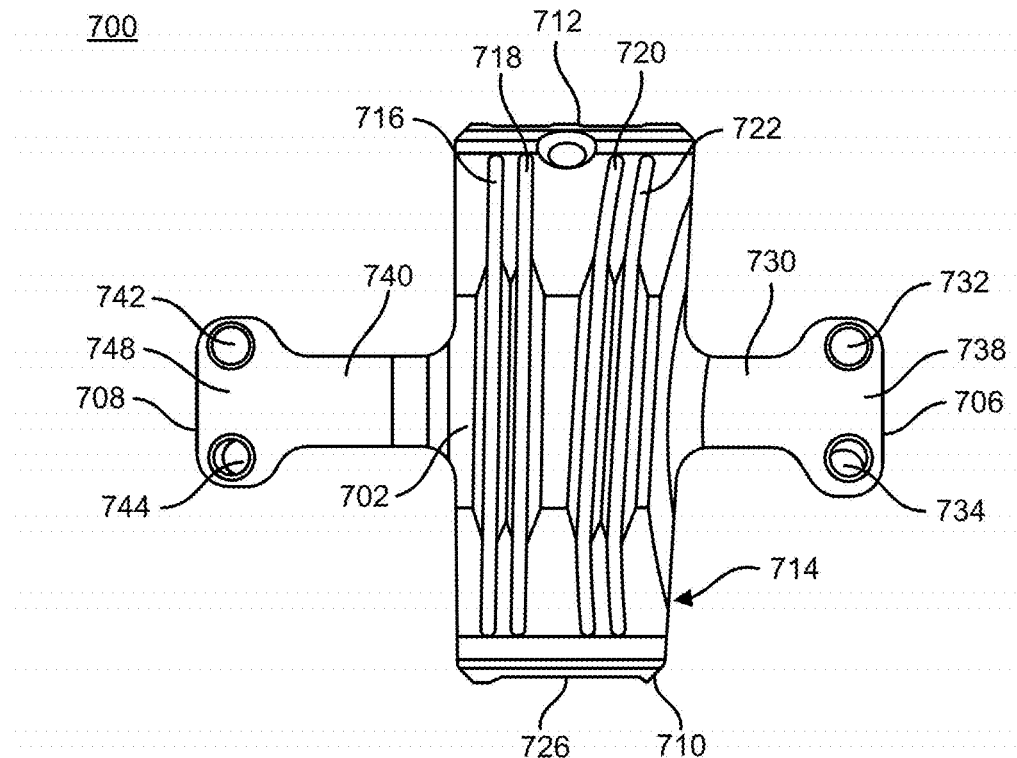
FIG. 81 is a top view of the cut guide of FIG. 75, in accordance with an aspect of the present disclosure.

As shown in FIGS. 75, 79 and 80, the top surface 702 of the base portion 714 may be, for example, curved or arced between the first side 710 and the second side 712. In one embodiment, the top surface 702 of the base portion 714 may include, for example, a flat or planar portion positioned between a first curvature or arc extending from the first side 710 to the flat portion and a second curvature or arc extending from a second side 712 to the flat portion. The end of the base portion 714 near the first end 706 of the cut guide 800 may be, for example, angled from the second side 712 to the first side 710, as shown in FIG. 81. The end of the base portion 714 near the second end 708 of the cut guide 700 may extend, for example, perpendicularly between the first side 710 and the second side 712, as shown in FIG. 81. The base portion 714 also includes at least one slot 716, 718, 720, 722, as shown in FIGS. 75-78, 81 and 82. In the depicted embodiment, the base portion 714 includes a first slot 716 adjacent to a second slot 718 and a third slot 720 adjacent to a fourth slot 722. The first and second slots 716, 718 may be, for example, positioned on the second end 708 of the base portion 714 and the third and fourth slots 720, 722 may be, for example, positioned on the first end 706 of the base portion 714.

With continued reference to FIGS. 75-78 and 81, the slots 716, 718, 720, 722 may extend, for example, linearly through the base portion 714 from the top surface 702 to the bottom surface 704 of the cut guide 700. Alternatively, the slots 716, 718, 720, 722 may also be, for example, angled as the slots 716, 718, 720, 722 extend from the top surface 702 to the bottom surface 704. The slots 716, 718, 720, 722 may be angled, for example, approximately 1° to 4° and more specifically, approximately 2°, as they extend between the top surface 702 and the bottom surface 704. It is also contemplated that some of slots 716, 718, 720, 722 may be angled and other slots 716, 718, 720, 722 may be linear as they extend through the base portion 714 from the top surface 702 to the bottom surface 704.

In addition, the slots 716, 718, 720, 722 may be angled as they extend between the first side 710 and the second side 712, for example, the slots may be angled approximately 0° to 30° as the slots 716, 718, 720, 722 extend between the first and second sides 710, 712. As shown, slots 716, 718 have an angle of 0° as the slots 716, 718 extend between the first and second sides 710, 712 and slots 720, 722 have an angle of 8° as the slots 720, 722 extend between the first and second sides 710, 712. Although not shown with respect to cut guide 700, it is also contemplated that both the first set of slots 716, 718 and the second set of slots 720, 722 may be straight as the slots 716, 718, 720, 722 extend between the first and second sides 710, 712. As shown, the slots 720, 722 are positioned to extend between the first and second sides 710, 712 parallel to the first metatarsal, as discussed in greater detail above with respect to the method of using the cut guide 700. The slots 716, 718, 720, 722 may be configured or sized and shaped to receive a saw blade and may have a width of, for example, approximately 0.58 mm to 0.92 mm. The slots 716, 718, 720, 722 may be positioned, for example, to allow for removal of the articular cartilage layer of the two bones. To prevent resecting more bone than absolutely necessary, the slots 716, 718, 720, 722 may be positioned, for example, such that the medial portion of the slots 716, 718, 720, 722 are aligned with the intersection of the cartilage and bone. In one embodiment, the slots 716, 718 are positioned a first distance from the extension member 728, the slots 720, 722 are positioned a second distance from the extension member 728. The first distance may be measured from the extension member 728 to an inner surface of the slots 716, 718 and the second distance may be measured from the extension member 728 to an inner surface of the slots 720, 722.

Figure 82:
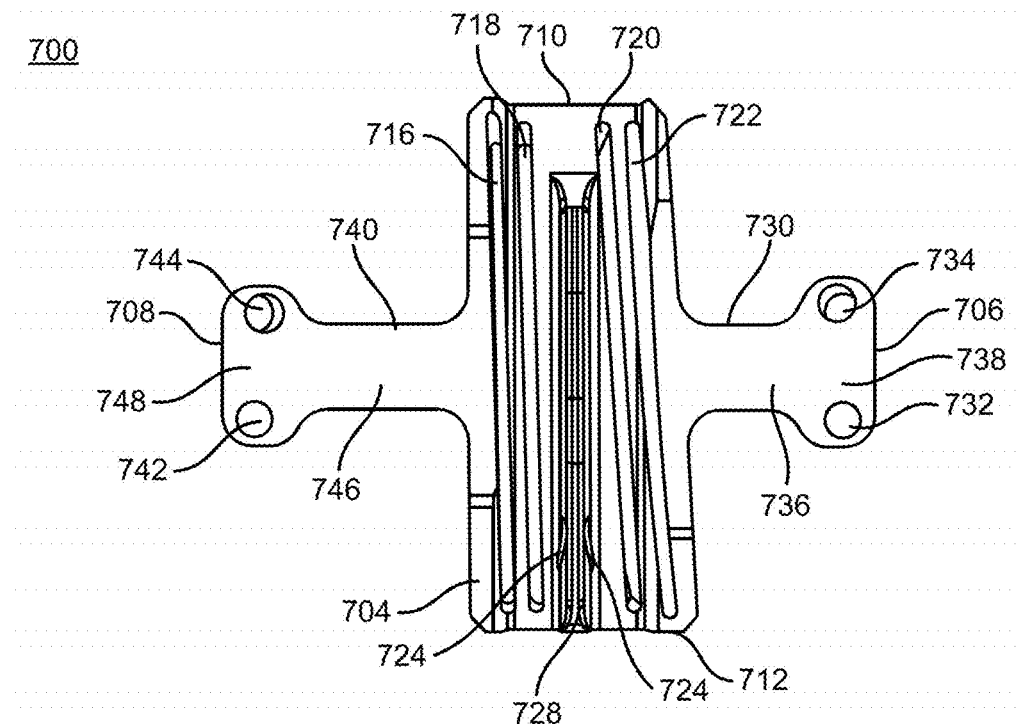
FIG. 82 is a bottom view of the cut guide of FIG. 75, in accordance with an aspect of the present disclosure.

The base portion 714 may also include a hole or dorsal hole 724, as shown in at least FIGS. 78, 81 and 82. The hole 724 may be of the type described above with reference to hole 124, which will not be described again here for brevity sake. As shown in FIGS. 75-78 and 82, the base portion 714 also includes a recessed region 726 positioned on the bottom surface 704. The recessed region 726 extends from the first side 710 to the second side 712 and into the base portion 714 a first distance from the bottom surface 704 toward the top surface 702. The extension member 728 is coupled to the recessed region 726 of the base portion 714 and extends away from the recessed region 726 of the base portion 714. In addition, the extension member 728 is positioned between the second slot 718 and the third slot 720 and also extends from the second side 712 toward the first side 710, as shown in FIGS. 79, 80 and 82. The extension member 728 may be shaped, for example, to fit within the joint space between two bones, such as, a first metatarsal and cuneiform, as well as to make contact with the adjoining articular joint surfaces. The extension member 728 may include a perpendicular portion near the first side 710 that extends perpendicularly away from the bottom surface 704. The perpendicular portion of the extension member 728 may be, for example, angled when the cut guide 700 is inserted into a patient's joint and the angle that the perpendicular portion is positioned at may correspond to the angle of the first tarso-metatarsal joint medially. The extension member 728 may also include an angled portion extending from the second side 712 to the end of the extension member 728. The angled portion of the extension member 728 may, for example, allow for the extension member 728 to fit within a variety of anatomic presentations. The angled portion of the extension member 728 may, for example, be oriented laterally and should align with the long axis of the tibia, as well as fit within the joint to rest against the relatively straight surface of the adjacent bone, for example, the second metatarsal. When the angled portion of the extension member 728 is oriented against the second metatarsal, the cut guide 700 will be positioned at a 45° angle in the frontal plane.

As shown in FIGS. 75, 76, 81 and 82, the first or proximal arm 730 may extend away from an end of the base portion 714 and may have, for example, a first portion extending from the base portion 714 to a coupling portion 738 positioned at the first end 706 of the cut guide 700. The coupling portion 738 may have a width larger than the width of the first portion of the first arm 730. The coupling portion 738 of the first arm 730 includes at least one opening 732, 734. In the depicted embodiment, the first arm 730 includes a first opening 732 and a second opening 734 positioned near the first end 706. The first opening 732 may be spaced apart from the second opening 734. The openings 732, 734 may extend from a top surface 702 to a bottom surface 704 of the coupling portion 738 of the cut guide 700. The openings 732, 734 may extend through the coupling portion 738 of the first arm 730, for example, parallel to the extension member 728, angled as they extend from the top surface 702 toward the bottom surface 704, or a combination of parallel and angled. In one embodiment, the first opening 732 may extend, for example, parallel to the extension member 728 and the second opening 734 may be, for example, angled with respect to the extension member 728 to permit the inserted wires, guide wires, k-wires and the like to cross above the cut guide 700 without intersecting. By positioning the openings 732, 734 such that inserted wires cross above the openings 732, 734 allows for a smaller surgical incision and less interaction or interference with other instruments during the procedure. The openings 732, 734 positioning the wires to cross also allows for the cut guide 700 to be, for example, suspended above and/or proximate to the bone surfaces being cut. The ability to suspend the cut guide 700 above the bone surfaces prevents the cut guide 700 from being titled because of varying patient anatomy and this avoids moving the slots 716, 718, 720, 722 which would affect the proposed cut angles. Alternative combinations of orientations of the openings 732, 734 are also contemplated, as would be understood by one of ordinary skill in the art from the above description. The first arm 730 may be shaped to provide a bone contacting surface 736 that corresponds to the shape of the bone that it will engage. The first arm 730 may be, for example, curved or arced as it extends between the first side 710 and the second side 712.

As shown in FIGS. 75, 76, 81 and 82, the second or distal arm 740 may extend away from an end of the base portion 714 and may have, for example, a first portion extending from the base portion 714 to a coupling portion 748 positioned at the second end 708 of the cut guide 700. The coupling portion 748 may have a width larger than the width of the first portion of the second arm 740. The coupling portion 748 of the second arm 740 includes at least one opening 742, 744. In the depicted embodiment, the second arm 740 includes a third opening 742 and a fourth opening 744 positioned near the second end 708. The third opening 742 may be spaced apart from the fourth opening 744 and extend from a top surface 702 to a bottom surface 704 of the cut guide 700. The openings 742, 744 may extend through the second arm 740, for example, parallel to the extension member 728, angled as they extend from the top surface 702 toward the bottom surface 704, or a combination of parallel and angled. In one embodiment, the third opening 742 may extend, for example, parallel to the extension member 728 and the fourth opening 744 may be, for example, angled with respect to the extension member 728 to permit inserted wires, guide wires, k-wires, and the like to cross above the cut guide 700 without intersecting. By positioning the openings 742, 744 such that the inserted wires cross above the openings 742, 744 allows for a smaller surgical incision and less interaction or interference with other instruments during the procedure. The openings 742, 744 being positioned for the wires to cross, also allows for the cut guide 700 to be, for example, suspended above and/or mated with the bone surfaces being cut. Suspending the cut guide 700 above the bone surfaces prevents the cut guide 700 from being angled because of varying patient anatomy which results in not having to move the slots 716, 718, 720, 722 which would affect the proposed cut angles. In one embodiment, the openings 732, 742 may be, for example, positioned such that they are parallel to one another as they extend between the top and bottom surfaces 702, 704. By positioning the openings 732, 742 parallel to each other, the cut guide 700 may be, for example, removed from guide wires inserted through openings 732, 742 without removing the guide wires. In addition, parallel openings 732, 742 allow for the relative rotation between the two guide wires to be measured or calculated after the bones are cut using cut guide 700. Further, the openings 732, 742 may be, for example, spaced apart from the extension member 728 a standard or set distance to allow for interchangeability with alternative cut guides 800, 900, 1000, if a different or additional resection is needed. Alternative, combinations of orientations of the openings 742, 744 are also contemplated, as would be understood by one of ordinary skill in the art from the above description. The second arm 740 may be shaped to provide a bone contacting surface 746 that corresponds to the shape of the bone that it will engage. The second arm 740 may be, for example, curved or arced as it extends between the first side 710 and the second side 712. The second arm 740 may have, for example, a larger length than the first arm 730.

Figure 83:
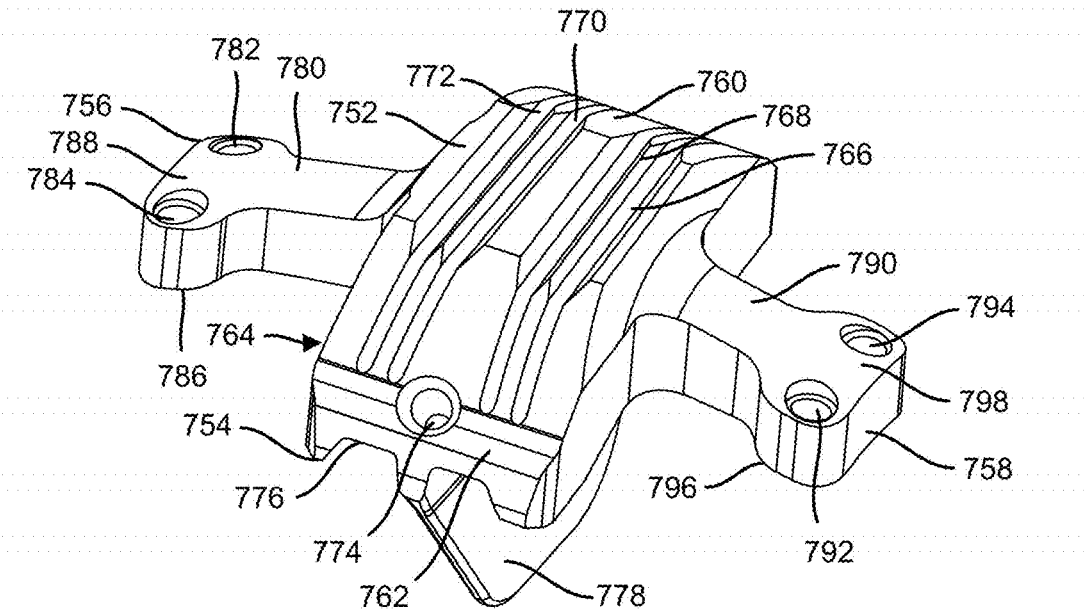
FIG. 83 is a top perspective view of an embodiment of a cut guide, in accordance with an aspect of the present disclosure.
Figure 84:
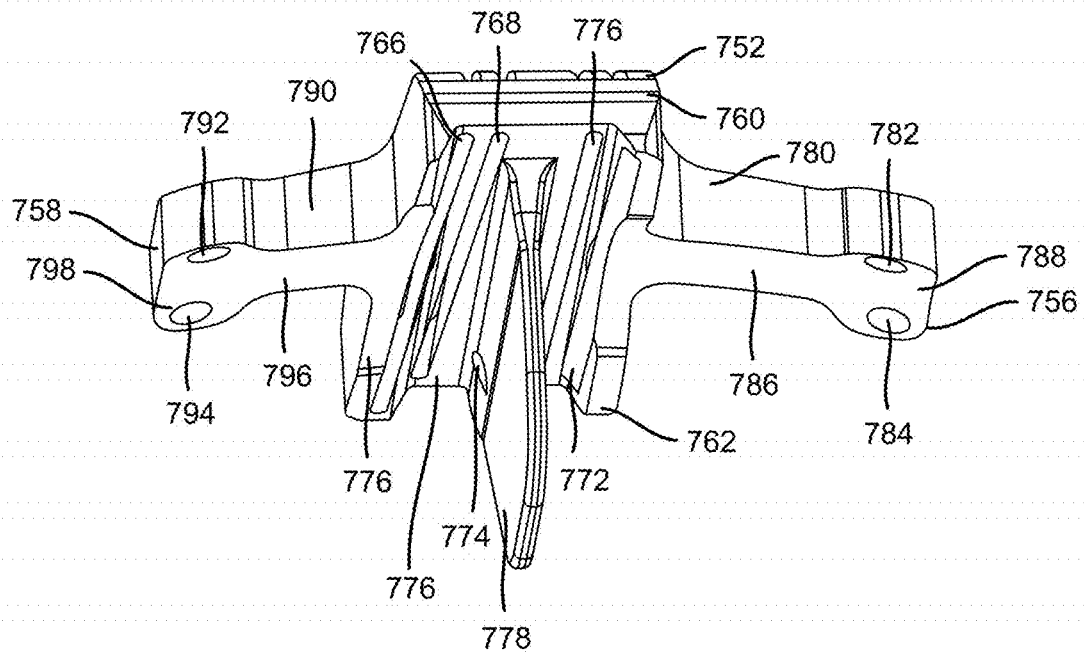
FIG. 84 is a bottom perspective view of the cut guide of FIG. 83, in accordance with an aspect of the present disclosure.

Referring now to FIGS. 83 and 84, another cut guide 750 is shown. The cut guide 750 is a mirror image of the cut guide 700 in a medial-lateral direction, which will not be described again in full detail for brevity purposes. For example, the hole 724 is positioned on a left side of the cut guide 700 when in an insertion position and the hole 774 is positioned on a right side of the cut guide 750 when in an insertion position. The cut guide 750 may be, for example, for a left foot. The cut guide 750 may include a top surface 752, a bottom surface 754, a first or proximal end 756, a second or distal end 758, a first or medial side 760, and a second or lateral side 762, which may be of the type described above with respect to the top surface 702, the bottom surface 704, the first or proximal end 706, the second or distal end 708, the first or medial side 710, and the second or lateral side 712, respectively. The cut guide 750 may also include a base portion 764 which may be the mirror image of the base portion 714, as described above. The slots 766, 768, 770, 772, the hole 774, and the recessed region 776 may be the same or similar to the slots 716, 718, 720, 722, the hole 724, and the recessed region 726, as described in greater detail above. Further, the cut guide 750 may include a fin, paddle or extension member 778, a first or proximal arm 780, and a second or distal arm 790, which may be as described above with respect to the extension member 728, the first arm 730, and the second arm 740, respectively. The coupling portion 788, the openings 782, 784 and the bone contacting surface 786 may be as described above with reference to the coupling portion 738, the openings 732, 734 and the bone contacting surface 736 and the coupling portion 798, the openings 792, 794 and the bone contacting surface 796 may be as described above with reference to the coupling portion 748, the openings 742, 744 and the bone contacting surface 746, which will not be described again here for brevity purposes.

Referring now to FIGS. 85-92, another cut guide 800 is shown. The cut guide 800 includes a top surface 802, a bottom surface 804, a first or proximal end 806, a second or distal end 808, a first or medial side 810, and a second or lateral side 812. The cut guide 800 also includes a base portion 814, a paddle, fin or extension member 828 extending away from the bottom surface 804 of the base portion 814, a first or proximal arm 830 extending away from the base portion 814 on the first end 806, and a second or distal arm 840 extending away from the base portion 814 on the second end 808. The cut guide 800 may be, for example, a right foot cut guide.

Figure 85:
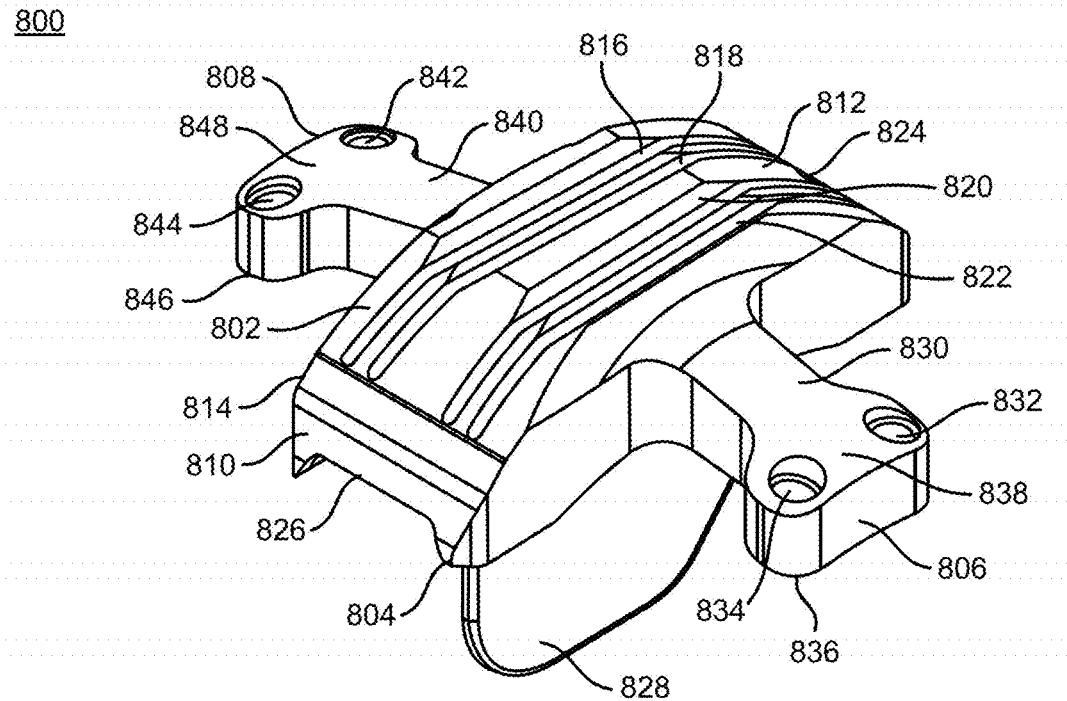
FIG. 85 is a top perspective view of an embodiment of a cut guide, in accordance with an aspect of the present disclosure.
Figure 89:
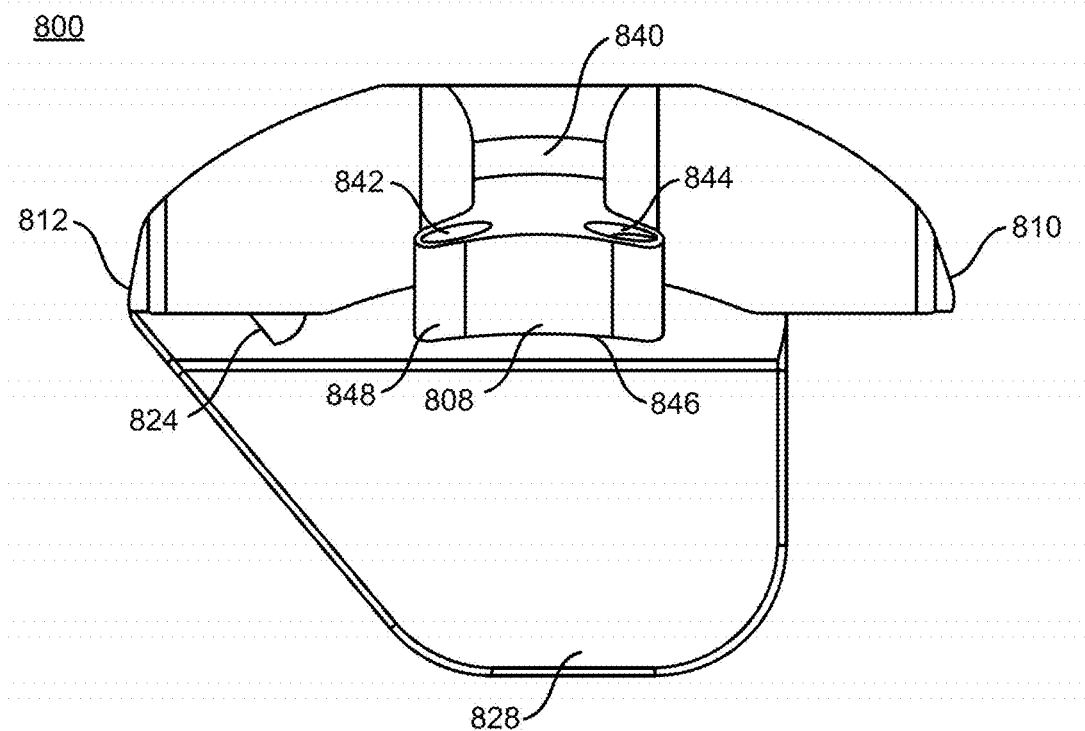
FIG. 89 is an end view of the cut guide of FIG. 85, in accordance with an aspect of the present disclosure.
Figure 90:
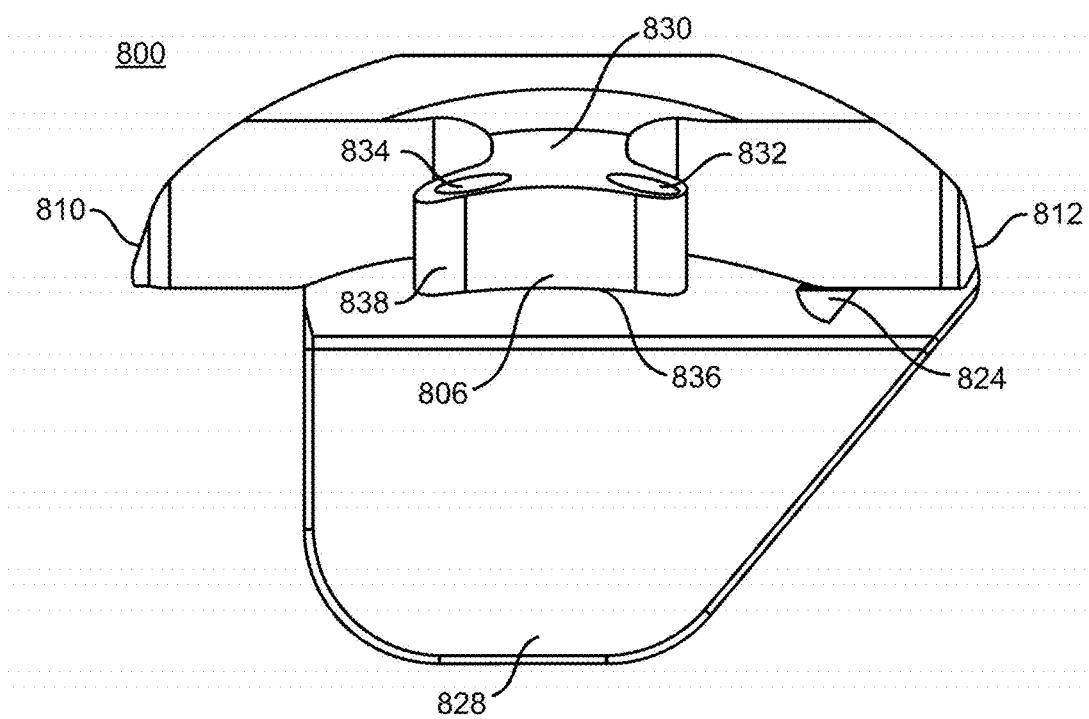
FIG. 90 is another end view of the cut guide of FIG. 85, in accordance with an aspect of the present disclosure.
Figure 91:
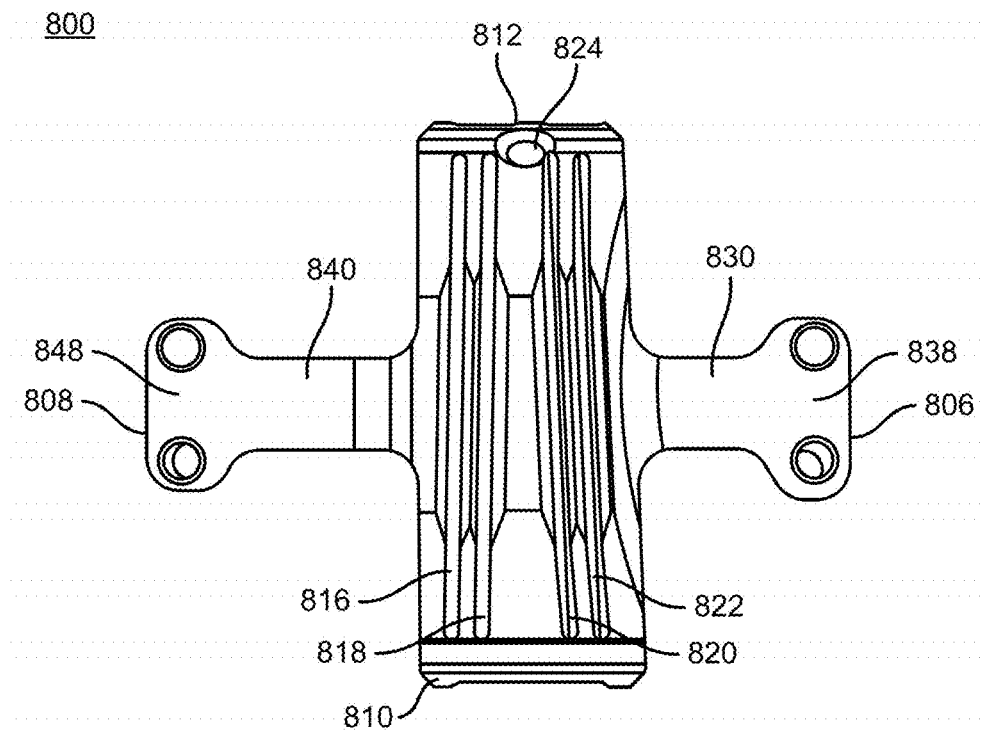
FIG. 91 is a top view of the cut guide of FIG. 85, in accordance with an aspect of the present disclosure.
Figure 92:
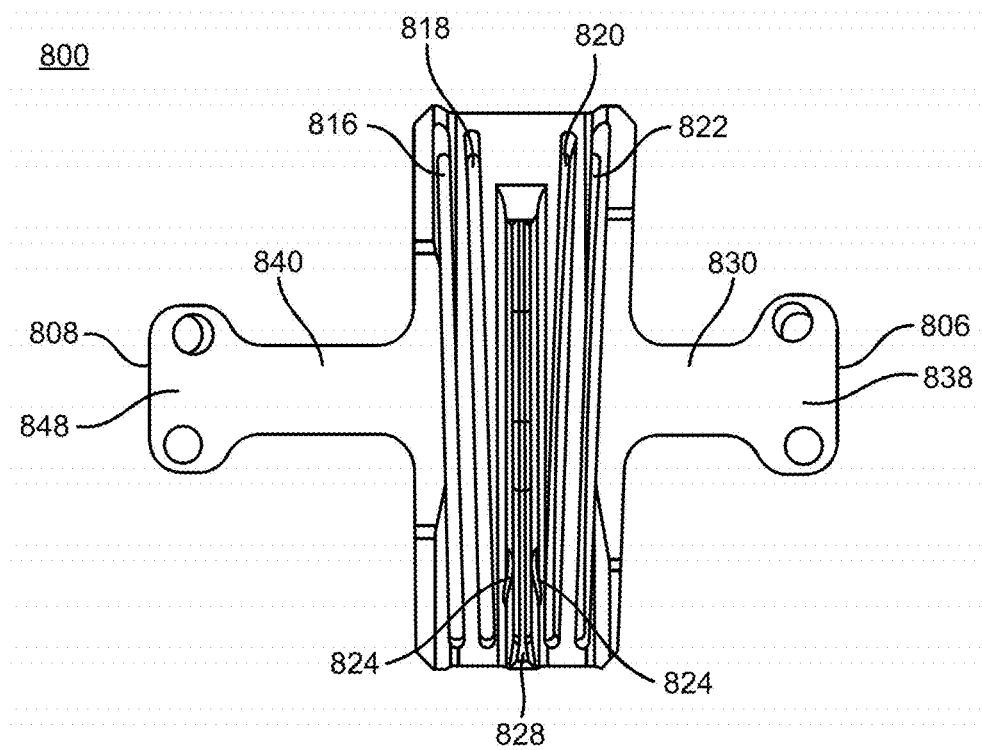
FIG. 92 is a bottom view of the cut guide of FIG. 85, in accordance with an aspect of the present disclosure.

As shown in FIGS. 85, 89 and 90, the top surface 802 of the base portion 814 may be, for example, curved or arced between the first side 810 and the second side 812. In one embodiment, the top surface 802 of the base portion 814 may include, for example, a flat or planar portion positioned between a first curvature or arc extending from the first side 810 to the flat portion and a second curvature or arc extending from a second side 812 to the flat portion. The end of the base portion 814 near the first end 806 of the cut guide 800 may be, for example, angled from the first side 810 to the second side 812, as shown in FIG. 91. The end of the base portion 814 near the second end 808 of the cut guide 800 may extend, for example, perpendicularly between the first side 810 and the second side 812, as shown in FIG. 91.

The base portion 814 also includes at least one slot 816, 818, 820, 822, as shown in FIGS. 85-88, 91 and 92. In the depicted embodiment, the base portion 814 includes a first slot 816 adjacent to a second slot 818 and a third slot 820 adjacent to a fourth slot 822. The first and second slots 816, 818 are positioned on the base portion 814 near the second end 808 of the cut guide 800 and the third and fourth slots 820, 822 are positioned on the base portion 814 near the first end 806 of the cut guide 800. The slots 816, 818, 820, 822 may extend, for example, linearly or angled through the base portion 814 from the top surface 802 to the bottom surface 804 of the cut guide 800. The slots 816, 818, 820, 822 may be, for example, angled approximately 1° to 4° and more specifically, approximately 2°, as the slots 816, 818, 820, 822 extend between the top and bottom surfaces 802, 804. It is also contemplated that some of slots 816, 818, 820, 822 may be angled and other slots 816, 818, 820, 822 may be linear as they extend through the base portion 814 from the top surface 802 to the bottom surface 804.

In addition, the slots 816, 818 may be oriented, for example, relatively perpendicular to the first side 810 and the second side 812 as the slots 816, 818 extend from the first side 810 to the second side 812, as shown in FIGS. 85-88, 91 and 92. The slots 820, 822 may be, for example, angled as the slots 820, 822 extend between the first side 810 to the second side 812. The slots 820, 822 may also be, for example, angled toward the slots 816, 818, as the slots 820, 822 extend from the first side 810 to the second side 812. The slots 820, 822 may also be positioned to extend parallel to the end of the base portion 814 near the first end 806 of the cut guide 800. The slots 820, 822 may be, for example, angled between approximately 8° and 22° as the slots 820, 822 extend from the second side 812 to the first side 810 providing for an angulation correction of 8° to 20°. The slots 816, 818, 820, 822 may be configured or sized and shaped to receive a saw blade and may have a width of, for example, approximately 0.58 mm to 0.92 mm. The slots 816, 818, 820, 822 may be positioned, for example, to allow for removal of the articular cartilage layer at the ends of the two bones. To prevent resecting more tissue than absolutely necessary, the slots 816, 818, 820, 822 may be positioned, for example, such that the medial portion of the slots 816, 818, 820, 822 are aligned with the intersection of the cartilage and bone.

Figure 86:
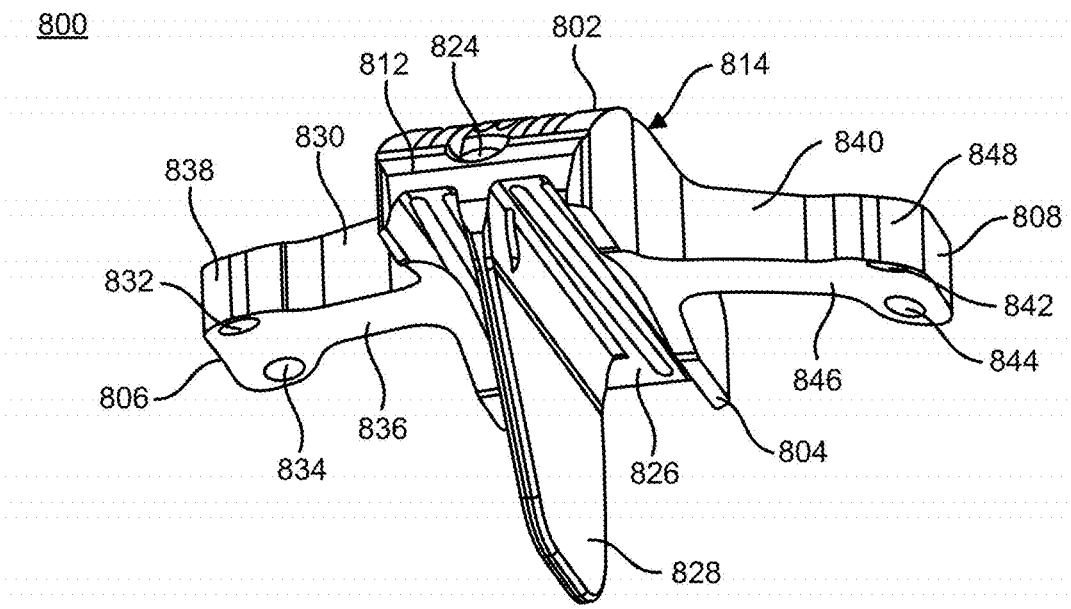
FIG. 86 is a bottom perspective view of the cut guide of FIG. 85, in accordance with an aspect of the present disclosure.
Figure 87:
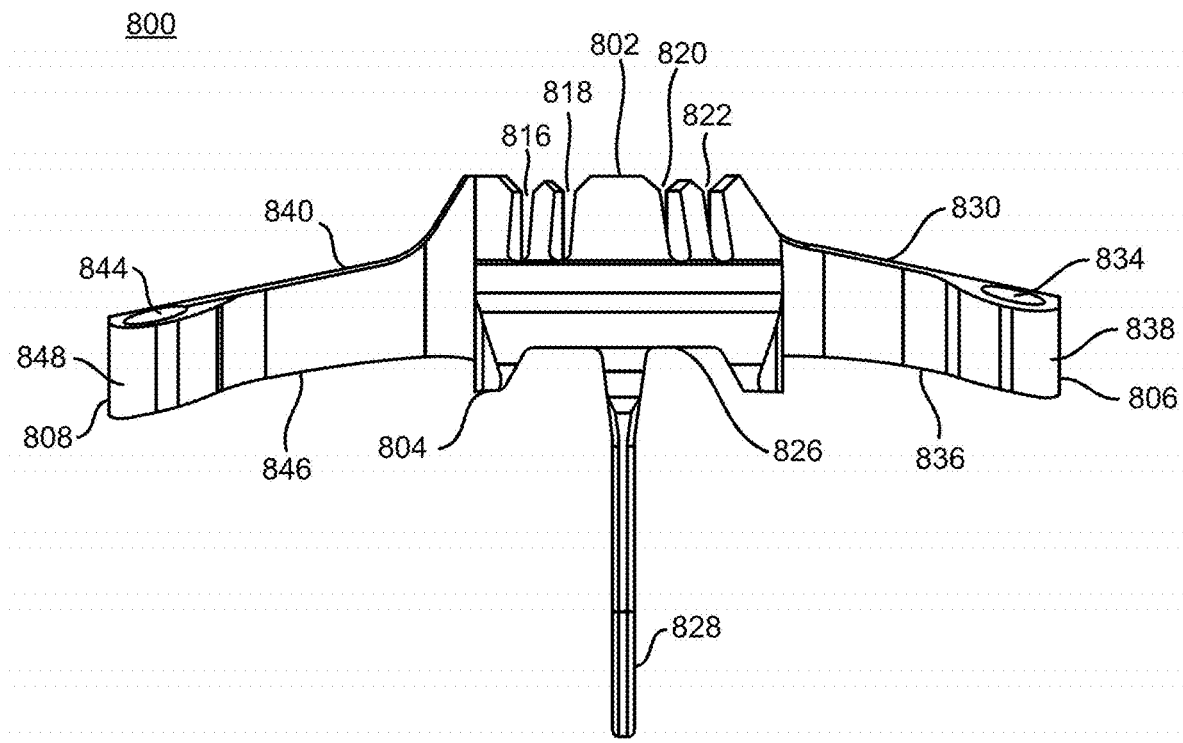
FIG. 87 is a side view of the cut guide of FIG. 85, in accordance with an aspect of the present disclosure.
Figure 88:
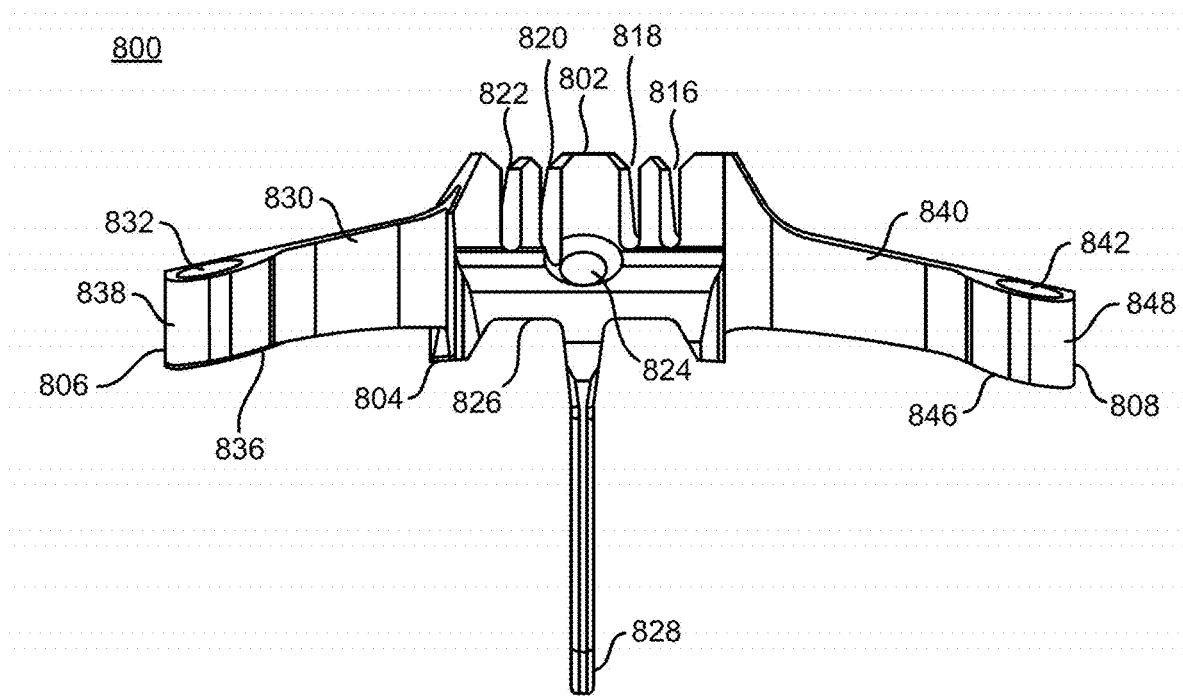
FIG. 88 is another side view of the cut guide of FIG. 85, in accordance with an aspect of the present disclosure.

The base portion 814 may also include a hole or dorsal hole 824, as shown in at least FIGS. 85, 86, and 88-91. The hole 824 is positioned between the second slot 818 and the third slot 820 near the second side 812 of the base portion 814. The hole 824 may extend, for example, into the base portion 814 from the top surface 802 of the cut guide 800 and to a point within the extension member 828. As shown in FIGS. 86, 89, 90 and 92, as the hole 824 extends into the extension member 828, the hole 824 forms an opening in a proximal-distal direction through the extension member 828. The hole 824 may, for example, extend into the cut guide 800 parallel to the angled portion of the extension member 828, as shown in FIG. 86. The hole 824 may be sized and shaped or configured, for example, to receive a wire, alignment wire, k-wire, guide wire or the like to provide information on the position of the cut guide 800 in a joint. For example, a wire inserted into hole 824 should align approximately with the long axis of the patient's tibia to provide the proper orientation of the cut guide 800 in the joint, which may be, for example, approximately 45° from dorsal and 45° from medial in the frontal plane.

Referring now to FIGS. 86-88 and 92, the base portion 814 also includes a recessed region 826 positioned on the bottom surface 804. The recessed region 826 extends from the first side 810 to the second side 812 and into the base portion 814 from the bottom surface 804 toward the top surface 802. The recessed region 826 extends to engage the bone contacting surface 836 of the first arm 830 at the first side 810 of the base portion 814. The extension member 828 is coupled to the recessed region 826 of the base portion 814 and extends away from the recessed region 826 of the base portion 814. In addition, the extension member 828 is positioned between the second slot 818 and the third slot 820. The extension member 828 also extends from the second side 812 toward the first side 810, as shown in FIGS. 86, 89, 90 and 92. The extension member 828 may include a perpendicular portion near the first side 810 that extends perpendicularly away from the bottom surface 804. The perpendicular portion of the extension member 828 may be, for example, angled when the cut guide 800 is inserted into a patient's joint and the angle that the perpendicular portion is positioned at may correspond to the angle of the first tarso-metatarsal joint medially. The extension member 828 may also include an angled portion extending from the second side 812 to the end or distal end of the extension member 828. The extension member 828 may be shaped, for example, to fit within the joint space between two bones, such as, a first metatarsal and cuneiform, as well as to mate with the articular joints. The angled portion of the extension member 828 may, for example, be oriented laterally and should align with the long axis of the tibia, as well as fit within the joint to rest against the relatively straight surface of the adjacent bone, for example, the second metatarsal. When the angled portion of the extension member 828 is oriented against the second metatarsal, the cut guide 800 will be positioned at a 45° angle in the frontal plane.

As shown in FIGS. 85, 86, 91 and 92, the first or proximal arm 830 may extend away from an end of the base portion 814 and may have, for example, a first portion extending from the base portion 814 to a coupling portion 838 positioned at the first end 806 of the cut guide 800. The coupling portion 838 may have a width larger than the width of the first portion of the first arm 830. The coupling portion 838 of the first arm 830 includes at least one opening 832, 834. In the depicted embodiment, the first arm 830 includes a first opening 832 and a second opening 834 positioned near the first end 806. The first opening 832 may be spaced apart from the second opening 834. The openings 832, 834 may extend from a top surface 802 to a bottom surface 804 of the coupling portion 838 of the cut guide 800. The openings 832, 834 may extend through the coupling portion 838 of the first arm 830, for example, parallel to the extension member 828, angled as they extend from the top surface 802 toward the bottom surface 804, or a combination of parallel and angled. In one embodiment, the first opening 832 may extend, for example, parallel to the extension member 828 and the second opening 834 may be, for example, angled with respect to the extension member 828 to permit the inserted wires, guide wires, k-wires and the like to cross above the cut guide 800 without intersecting. By positioning the openings 832, 834 such that inserted wires cross above the openings 832, 834 allows for a smaller surgical incision and less interaction or interference with other instruments during the procedure. The openings 832, 834 positioning the wires to cross also allows for the cut guide 800 to be, for example, suspended above and/or proximate to the bone surfaces being cut. The ability to suspend the cut guide 800 above the bone surfaces prevents the cut guide 800 from being titled because of varying patient anatomy and this avoids moving the slots 816, 818, 820, 822 which would affect the proposed cut angles. Alternative combinations of orientations of the openings 832, 834 are also contemplated, as would be understood by one of ordinary skill in the art from the above description. The first arm 830 may be shaped to provide a bone contacting surface 836 that corresponds to the shape of the bone that it will engage. The first arm 830 may be, for example, curved or arced as it extends between the first side 810 and the second side 812.

As shown in FIGS. 85, 86, 91 and 92, the second or distal arm 840 may extend away from an end of the base portion 814 and may have, for example, a first portion extending from the base portion 814 to a coupling portion 848 positioned at the second end 808 of the cut guide 800. The coupling portion 848 may have a width larger than the width of the first portion of the second arm 840. The coupling portion 848 of the second arm 840 includes at least one opening 842, 844. In the depicted embodiment, the second arm 840 includes a third opening 842 and a fourth opening 844 positioned near the second end 808. The third opening 842 may be spaced apart from the fourth opening 844 and extend from a top surface 802 to a bottom surface 804 of the cut guide 800. The openings 842, 844 may extend through the second arm 840, for example, parallel to the extension member 828, angled as they extend from the top surface 802 toward the bottom surface 804, or a combination of parallel and angled. In one embodiment, the third opening 842 may extend, for example, parallel to the extension member 828 and the fourth opening 844 may be, for example, angled with respect to the extension member 828 to permit inserted wires, guide wires, k-wires, and the like to cross above the cut guide 800 without intersecting. By positioning the openings 842, 844 such that the inserted wires cross above the openings 842, 844 allows for a smaller surgical incision and less interaction or interference with other instruments during the procedure. The openings 842, 844 being positioned for the wires to cross, also allows for the cut guide 800 to be, for example, suspended above and/or mated with the bone surfaces being cut. Suspending the cut guide 800 above the bone surfaces prevents the cut guide 800 from being angled because of varying patient anatomy which results in not having to move the slots 816, 818, 820, 822 which would affect the proposed cut angles. In one embodiment, the openings 832, 842 may be, for example, positioned such that they are parallel to one another as they extend between the top and bottom surfaces 802, 804. By positioning the openings 832, 842 parallel to each other, the cut guide 800 may be, for example, removed from guide wires inserted through openings 832, 842 without removing the guide wires. In addition, parallel openings 832, 842 allow for the relative rotation between the two guide wires to be measured or calculated after the bones are cut using cut guide 800. Further, the openings 832, 842 may be, for example, spaced apart from the extension member 828 a standard or set distance to allow for interchangeability with alternative cut guides 700, 900, 1000, if a different or additional resection is needed. Alternative, combinations of orientations of the openings 842, 844 are also contemplated, as would be understood by one of ordinary skill in the art from the above description. The second arm 840 may be shaped to provide a bone contacting surface 846 that corresponds to the shape of the bone that it will engage. The second arm 840 may be, for example, curved or arced as it extends between the first side 810 and the second side 812. The second arm 840 may have, for example, a larger length than the first arm 830.

Figure 93:
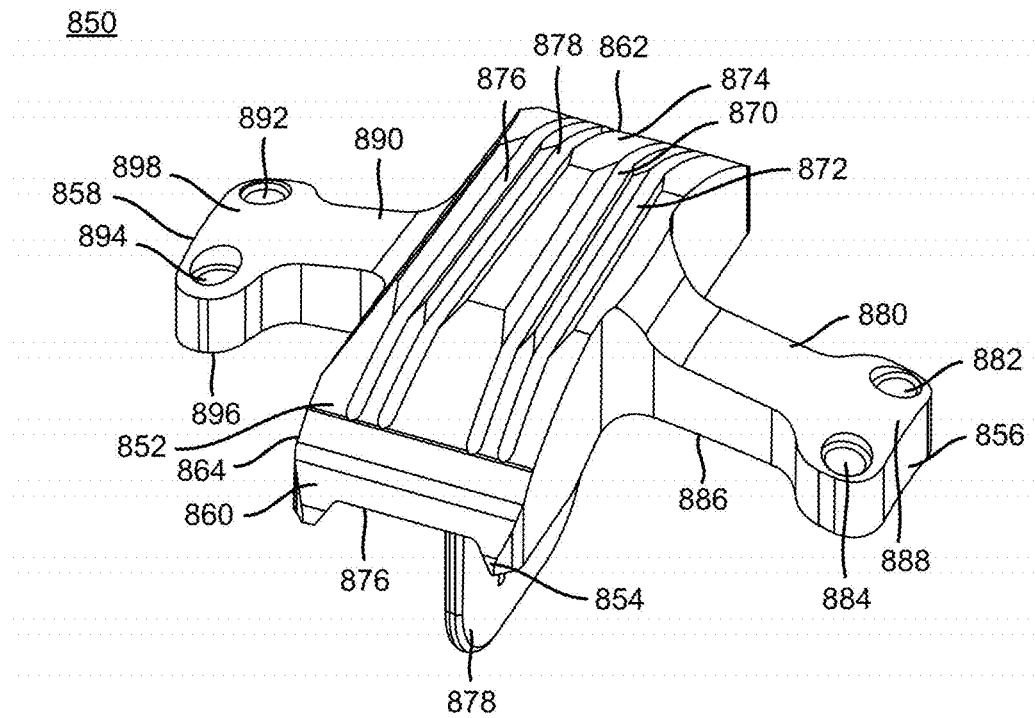
FIG. 93 is a top perspective view of an embodiment of a cut guide, in accordance with an aspect of the present disclosure.
Figure 94:
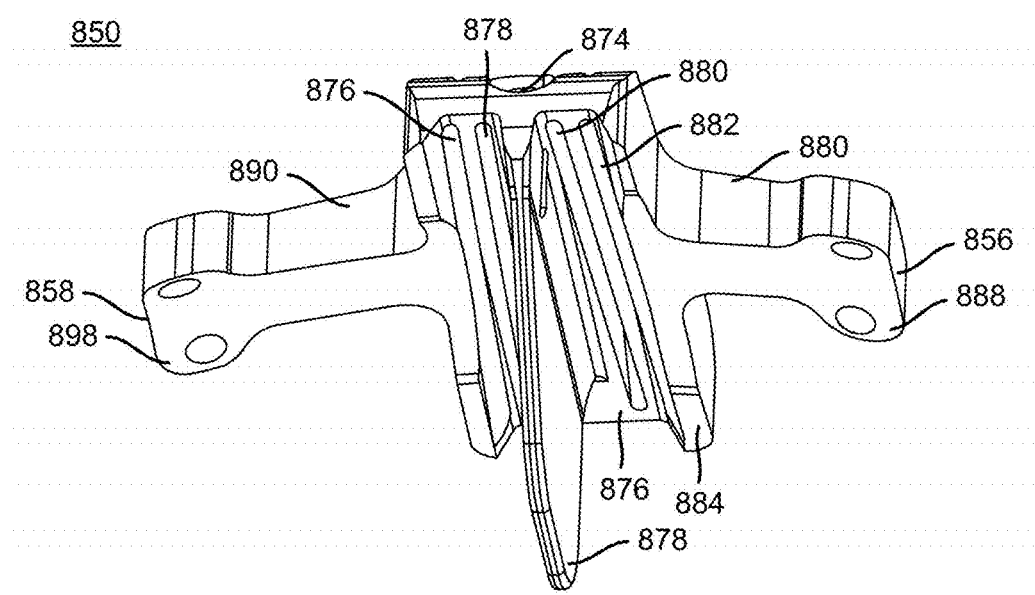
FIG. 94 is a bottom perspective view of the cut guide of FIG. 93, in accordance with an aspect of the present disclosure.

Another cut guide 850 is shown in FIGS. 93 and 94. The cut guide 850 is a mirror image of the cut guide 800 in a medial-lateral direction, which will not be described again in full detail for brevity purposes. For example, the hole 824 is positioned on a left side of the cut guide 800 when in an insertion position and the hole 874 is positioned on a right side of the cut guide 850 when in an insertion position. The cut guide 850 may be, for example, for a left foot. The cut guide 850 may include a top surface 852, a bottom surface 854, a first or proximal end 856, a second or distal end 858, a first or medial side 860, and a second or lateral side 862, which may be of the type described above with respect to the top surface 802, the bottom surface 804, the first or proximal end 806, the second or distal end 808, the first or medial side 810, and the second or lateral side 812, respectively. The cut guide 850 may also include a base portion 864 which may be the mirror image of the base portion 814, as described above. The slots 866, 868, 870, 872, the hole 874, and the recessed region 876 may be the same or similar to the slots 816, 818, 820, 822, the hole 824, and the recessed region 826, as described in greater detail above. Further, the cut guide 850 may include a fin, paddle or extension member 878, a first or proximal arm 880, and a second or distal arm 890, which may be as described above with respect to the extension member 828, the first arm 830, and the second arm 840, respectively. The coupling portion 888, the openings 882, 884 and the bone contacting surface 886 may be as described above with reference to the coupling portion 838, the openings 832, 834 and the bone contacting surface 836 and the coupling portion 898, the openings 892, 894 and the bone contacting surface 896 may be as described above with reference to the coupling portion 848, the openings 842, 844 and the bone contacting surface 846, which will not be described again here for brevity purposes.

Referring now to FIGS. 95-102, a cut guide 900 is shown. The cut guide 900 includes a top surface 902, a bottom surface 904, a first or proximal end 906, a second or distal end 908, a first or medial side 910, and a second or lateral side 912. The cut guide 900 also includes a base portion 914, a paddle, fin or extension member 928 extending away from the bottom surface 904 of the base portion 914, a first or proximal arm 930 extending away from the base portion 914 on the first end 906, and a second or distal arm 940 extending away from the base portion 914 on the second end 908. The cut guide 900 may be, for example, a right foot cut guide.

Figure 95:
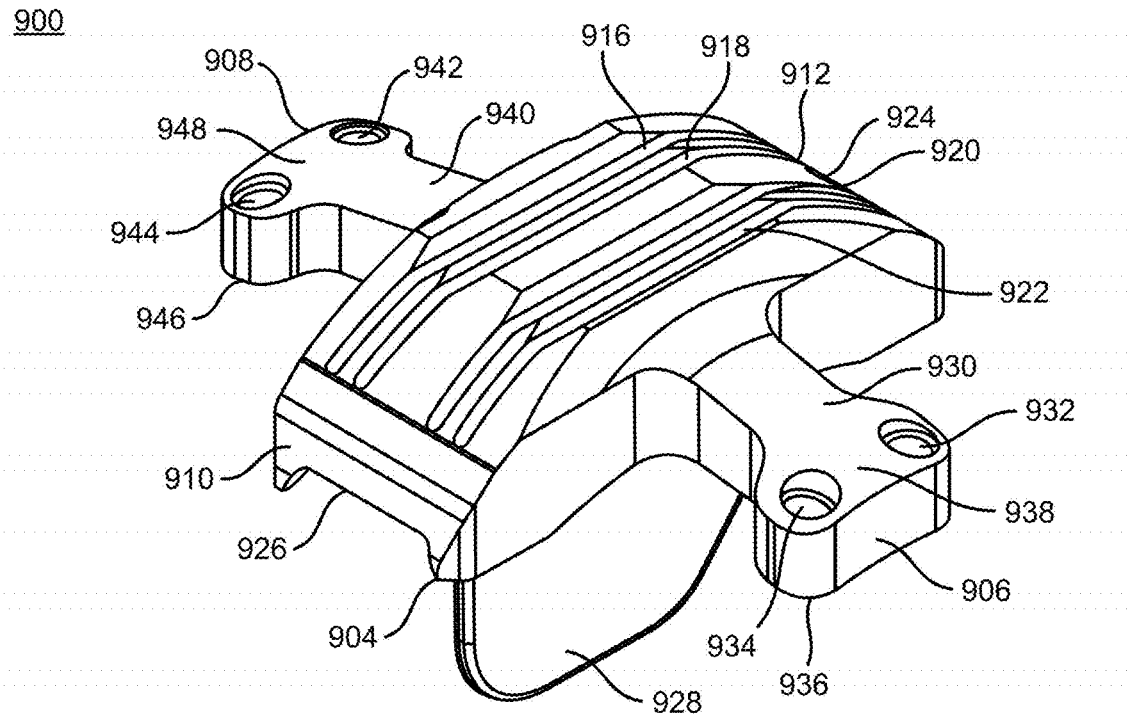
FIG. 95 is a top perspective view of an embodiment of a cut guide, in accordance with an aspect of the present disclosure.
Figure 99:
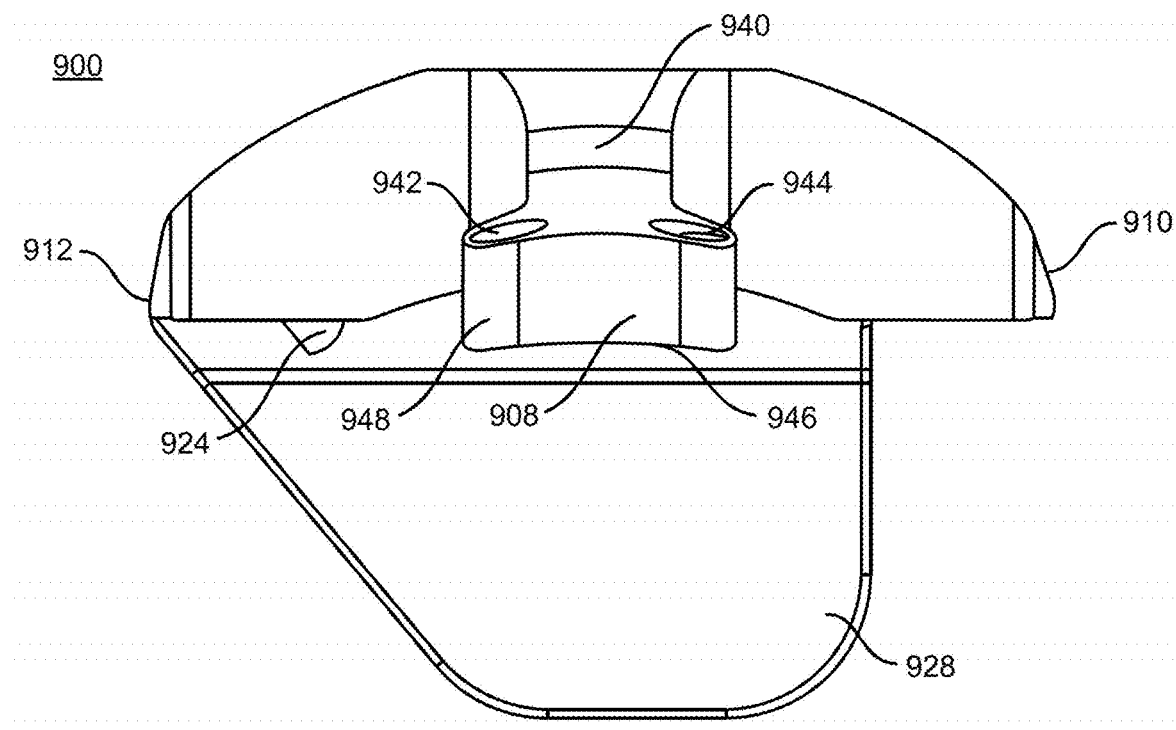
FIG. 99 is an end view of the cut guide of FIG. 95, in accordance with an aspect of the present disclosure.
Figure 100:
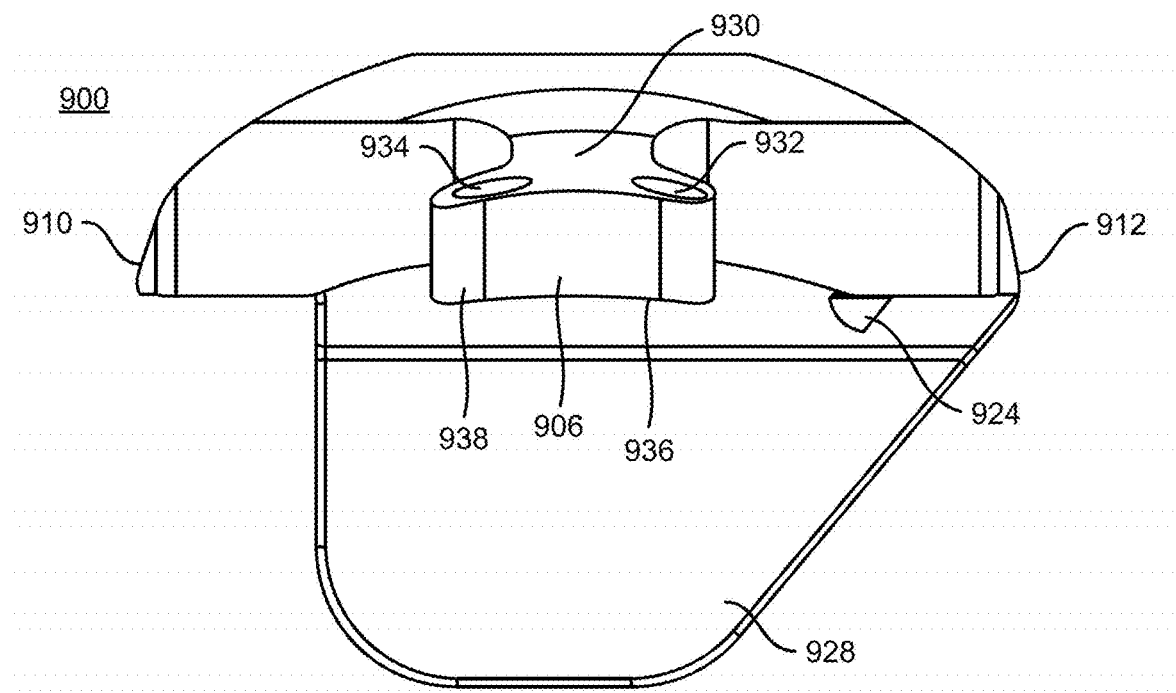
FIG. 100 is another end view of the cut guide of FIG. 95, in accordance with an aspect of the present disclosure.
Figure 102:
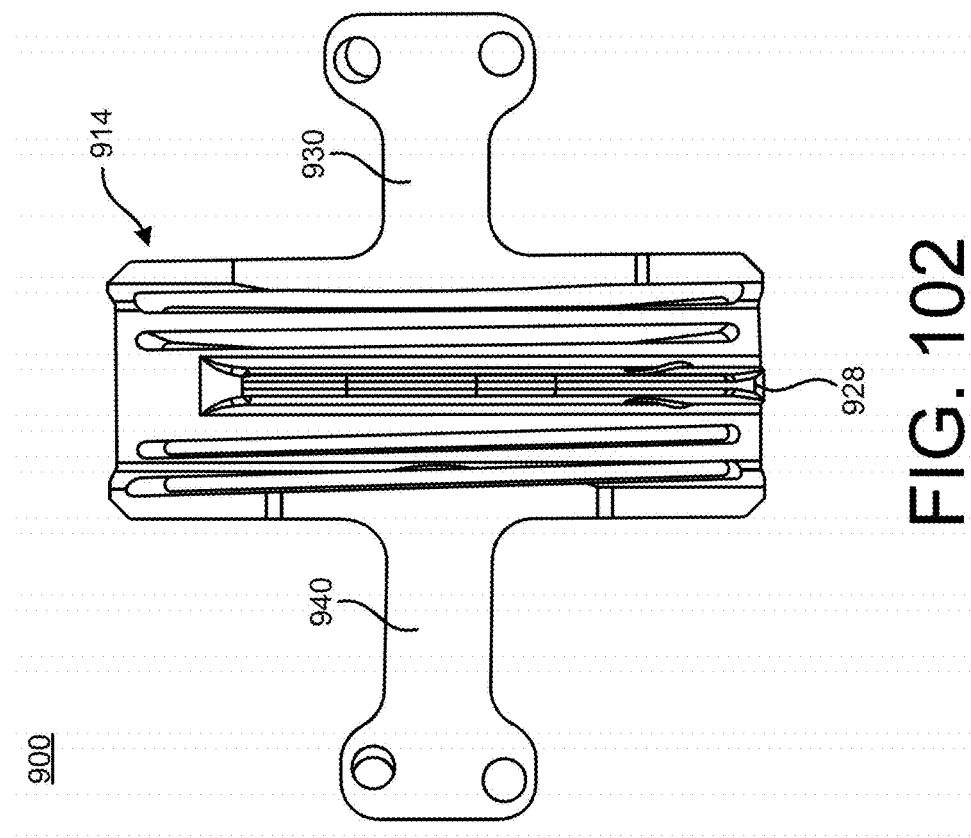
FIG. 102 is a bottom view of the cut guide of FIG. 95, in accordance with an aspect of the present disclosure.
Figure 101:
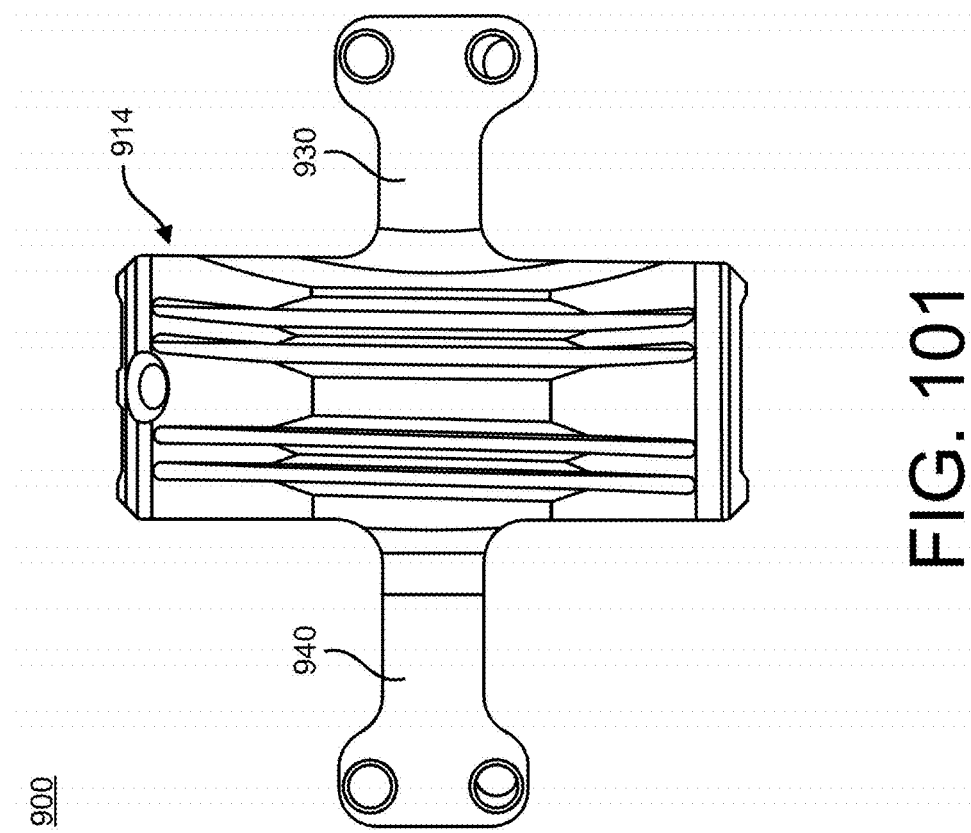
FIG. 101 is a top view of the cut guide of FIG. 95, in accordance with an aspect of the present disclosure.

As shown in FIGS. 95, 99 and 100, the top surface 902 of the base portion 914 may be, for example, curved or arced between the first side 910 and the second side 912. In one embodiment, the top surface 902 of the base portion 914 may include, for example, a flat or planar portion positioned between a first curvature or arc extending from the first side 910 to the flat portion and a second curvature or arc extending from a second side 912 to the flat portion. The end of the base portion 914 near the first end 906 of the cut guide 900 may extend, for example, perpendicularly between the first side 910 to the second side 912, as shown in FIG. 101. The end of the base portion 914 near the second end 908 of the cut guide 900 may extend, for example, perpendicularly between the first side 910 and the second side 912, as shown in FIG. 101.

The base portion 914 also includes at least one slot 916, 918, 920, 922, as shown in FIGS. 89-98, 101 and 102. In the depicted embodiment, the base portion 914 includes a first slot 916 adjacent to a second slot 918 and a third slot 920 adjacent to a fourth slot 922. The first and second slots 916, 918 are positioned on the base portion 914 near the second end 908 of the cut guide 900 and the third and fourth slots 920, 922 are positioned on the base portion 914 near the first end 906 of the cut guide 900. The slots 916, 918, 920, 922 may extend, for example, linearly or angled through the base portion 914 from the top surface 902 to the bottom surface 904 of the cut guide 900. The slots 916, 918, 920, 922 may be, for example, angled approximately 1° to 4° and more specifically, approximately 2°, as the slots 916, 918, 920, 922 extend between the top and bottom surfaces 902, 904. It is also contemplated that some of slots 916, 918, 920, 922 may be angled and other slots 916, 918, 920, 922 may be linear as they extend through the base portion 914 from the top surface 902 to the bottom surface 904.

In addition, the slots 916, 918 may be oriented, for example, relatively perpendicular to the first side 910 and the second side 912 as the slots 916, 918 extend from the first side 910 to the second side 912, as shown in FIGS. 95-98, 101 and 102. The slots 916, 918 may also be positioned to extend parallel to the end of the base portion 914 near the second end 908 of the cut guide 900. The slots 920, 922 may also be oriented, for example, relatively perpendicular to the first side 910 and the second side 912 as the slots 920, 922 extend from the first side 910 to the second side 912. The slots 920, 922 may also be positioned to extend parallel to the end of the base portion 914 near the first end 906 of the cut guide 900. The slots 916, 918, 920, 922 may be, for example, angled approximately 0° to 30° as the slots 916, 918, 920, 922 extend from the second side 912 to the first side 910 providing for an angulation correction of 4° to 20°. The slots 916, 918, 920, 922 may be configured or sized and shaped to receive a saw blade and may have a width of, for example, approximately 0.58 mm to 0.92 mm.

The slots 916, 918, 920, 922 may be positioned, for example, to allow for removal of the articular cartilage layer at the ends of the two bones. To prevent resecting more tissue than absolutely necessary, the slots 916, 918, 920, 922 may be positioned, for example, such that the medial portion of the slots 916, 918, 920, 922 are aligned with the intersection of the cartilage and bone.

Figure 96:
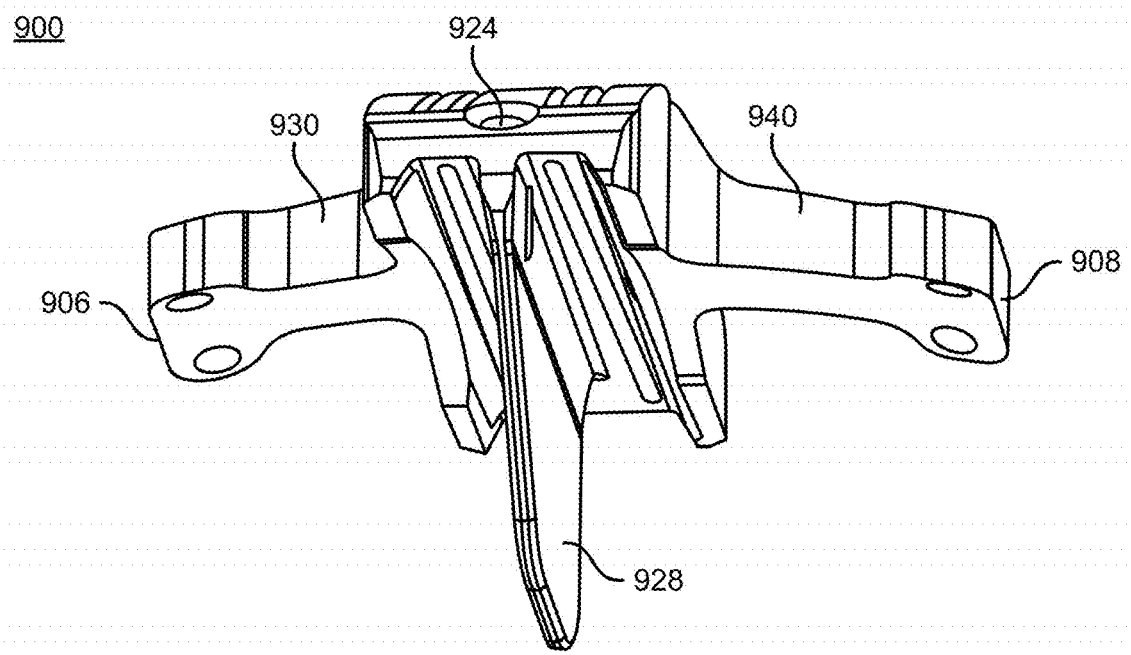
FIG. 96 is a bottom perspective view of the cut guide of FIG. 95, in accordance with an aspect of the present disclosure.
Figure 97:
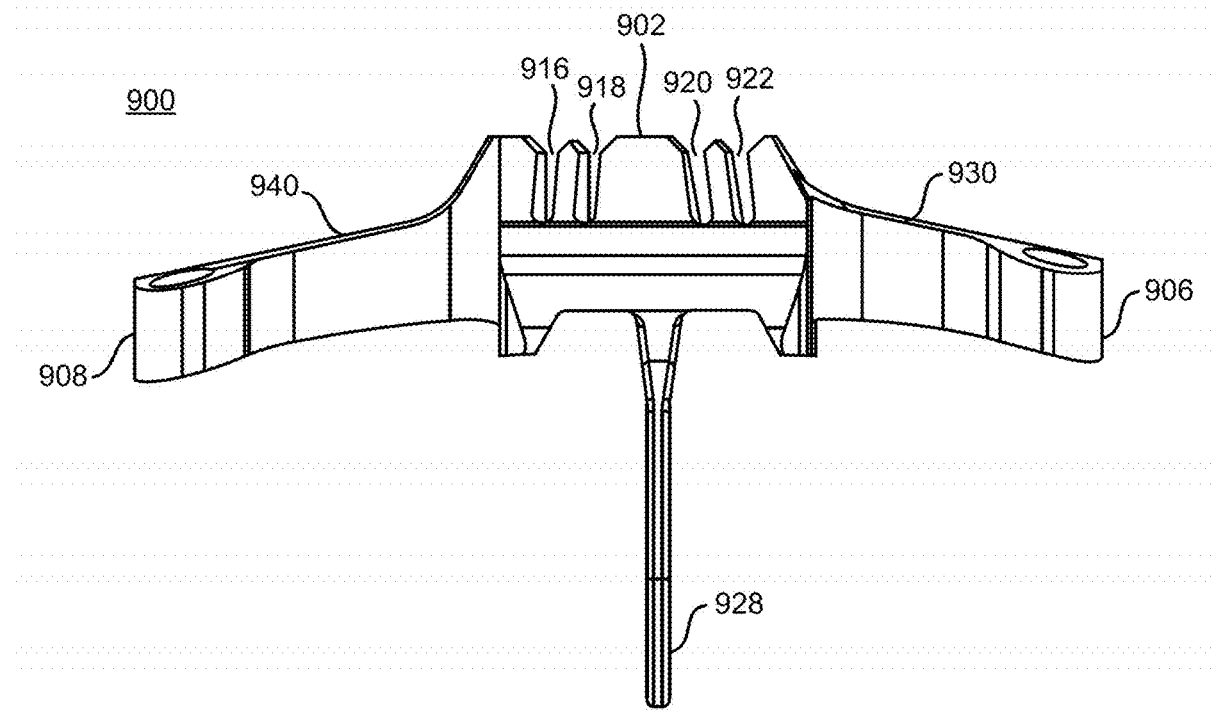
FIG. 97 is a side view of the cut guide of FIG. 95, in accordance with an aspect of the present disclosure.
Figure 98:
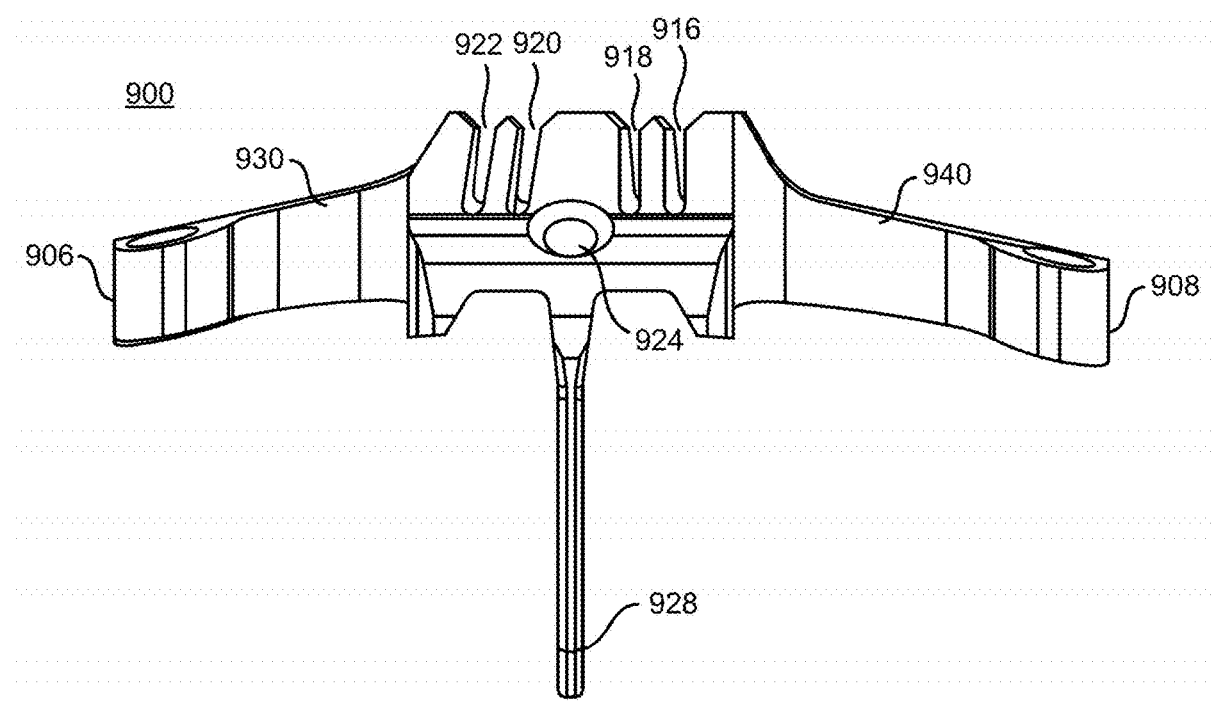
FIG. 98 is another side view of the cut guide of FIG. 95, in accordance with an aspect of the present disclosure.

The base portion 914 may also include a hole or dorsal hole 924, as shown in at least FIGS. 95, 96, and 98-101. The hole 924 is positioned between the second slot 918 and the third slot 920 near the second side 912 of the base portion 914. The hole 924 may extend, for example, into the base portion 914 from the top surface 902 of the cut guide 900 and to a point within the extension member 928. As shown in FIGS. 96, 99, 100 and 102, as the hole 924 extends into the extension member 928, the hole 924 forms an opening in a proximal-distal direction through the extension member 928. The hole 924 may, for example, extend into the cut guide 900 parallel to the angled portion of the extension member 928, as shown in FIG. 96. The hole 924 may be sized and shaped or configured, for example, to receive a wire, alignment wire, k-wire, guide wire or the like to provide information on the position of the cut guide 900 in a joint. For example, a wire inserted into hole 924 should align approximately with the long axis of the patient's tibia to provide the proper orientation of the cut guide 900 in the joint, which may be, for example, approximately 45° from dorsal and 45° from medial in the frontal plane.

Referring now to FIGS. 96-98 and 102, the base portion 914 also includes a recessed region 926 positioned on the bottom surface 904. The recessed region 926 extends from the first side 910 to the second side 912 and into the base portion 914 from the bottom surface 904 toward the top surface 902. The recessed region 926 extends to engage the bone contacting surface 936 of the first arm 930 at the first side 910 of the base portion 914. The extension member 928 is coupled to the recessed region 926 of the base portion 914 and extends away from the recessed region 926 of the base portion 914. In addition, the extension member 928 is positioned between the second slot 918 and the third slot 920. The extension member 928 also extends from the second side 912 toward the first side 910, as shown in FIGS. 96, 99, 100 and 102. The extension member 928 may include a perpendicular portion near the first side 910 that extends perpendicularly away from the bottom surface 904. The perpendicular portion of the extension member 928 may be, for example, angled when the cut guide 900 is inserted into a patient's joint and the angle that the perpendicular portion is positioned at may correspond to the angle of the first tarso-metatarsal joint medially. The extension member 928 may also include an angled portion extending from the second side 912 to the end or distal end of the extension member 928. The extension member 928 may be shaped, for example, to fit within the joint space between two bones, such as, a first metatarsal and cuneiform, as well as to mate with the articular joints. The angled portion of the extension member 928 may, for example, be oriented laterally and should align with the long axis of the tibia, as well as fit within the joint to rest against the relatively straight surface of the adjacent bone, for example, the second metatarsal. When the angled portion of the extension member 928 is oriented against the second metatarsal, the cut guide 900 will be positioned at a 45° angle in the frontal plane.

As shown in FIGS. 95, 96, 101 and 102, the first or proximal arm 930 may extend away from an end of the base portion 914 and may have, for example, a first portion extending from the base portion 914 to a coupling portion 938 positioned at the first end 906 of the cut guide 900. The coupling portion 938 may have a width larger than the width of the first portion of the first arm 930. The coupling portion 938 of the first arm 930 includes at least one opening 932, 934. In the depicted embodiment, the first arm 930 includes a first opening 932 and a second opening 934 positioned near the first end 906. The first opening 932 may be spaced apart from the second opening 934. The openings 932, 934 may extend from a top surface 902 to a bottom surface 904 of the coupling portion 938 of the cut guide 900. The openings 932, 934 may extend through the coupling portion 938 of the first arm 930, for example, parallel to the extension member 928, angled as they extend from the top surface 902 toward the bottom surface 904, or a combination of parallel and angled. In one embodiment, the first opening 932 may extend, for example, parallel to the extension member 928 and the second opening 934 may be, for example, angled with respect to the extension member 928 to permit the inserted wires, guide wires, k-wires and the like to cross above the cut guide 900 without intersecting. By positioning the openings 932, 934 such that inserted wires cross above the openings 932, 934 allows for a smaller surgical incision and less interaction or interference with other instruments during the procedure. The openings 932, 934 positioning the wires to cross also allows for the cut guide 900 to be, for example, suspended above and/or proximate to the bone surfaces being cut. The ability to suspend the cut guide 900 above the bone surfaces prevents the cut guide 900 from being titled because of varying patient anatomy and this avoids moving the slots 916, 918, 920, 922 which would affect the proposed cut angles. Alternative combinations of orientations of the openings 932, 934 are also contemplated, as would be understood by one of ordinary skill in the art from the above description. The first arm 930 may be shaped to provide a bone contacting surface 936 that corresponds to the shape of the bone that it will engage. The first arm 930 may be, for example, curved or arced as it extends between the first side 910 and the second side 912.

As shown in FIGS. 95, 96, 101 and 102, the second or distal arm 940 may extend away from an end of the base portion 914 and may have, for example, a first portion extending from the base portion 914 to a coupling portion 948 positioned at the second end 908 of the cut guide 900. The coupling portion 948 may have a width larger than the width of the first portion of the second arm 940. The coupling portion 948 of the second arm 940 includes at least one opening 942, 944. In the depicted embodiment, the second arm 940 includes a third opening 942 and a fourth opening 944 positioned near the second end 908. The third opening 942 may be spaced apart from the fourth opening 944 and extend from a top surface 902 to a bottom surface 904 of the cut guide 900. The openings 942, 944 may extend through the second arm 940, for example, parallel to the extension member 928, angled as they extend from the top surface 902 toward the bottom surface 904, or a combination of parallel and angled. In one embodiment, the third opening 942 may extend, for example, parallel to the extension member 928 and the fourth opening 944 may be, for example, angled with respect to the extension member 928 to permit inserted wires, guide wires, k-wires, and the like to cross above the cut guide 900 without intersecting. By positioning the openings 942, 944 such that the inserted wires cross above the openings 942, 944 allows for a smaller surgical incision and less interaction or interference with other instruments during the procedure. The openings 942, 944 being positioned for the wires to cross, also allows for the cut guide 900 to be, for example, suspended above and/or mated with the bone surfaces being cut. Suspending the cut guide 900 above the bone surfaces prevents the cut guide 900 from being angled because of varying patient anatomy which results in not having to move the slots 916, 918, 920, 922 which would affect the proposed cut angles. In one embodiment, the openings 932, 942 may be, for example, positioned such that they are parallel to one another as they extend between the top and bottom surfaces 902, 904. By positioning the openings 932, 942 parallel to each other, the cut guide 900 may be, for example, removed from guide wires inserted through openings 932, 942 without removing the guide wires. In addition, parallel openings 932, 942 allow for the relative rotation between the two guide wires to be measured or calculated after the bones are cut using cut guide 900. Further, the openings 932, 942 may be, for example, spaced apart from the extension member 928 a standard or set distance to allow for interchangeability with alternative cut guides 700, 800, 1000, if a different or additional resection is needed. Alternative, combinations of orientations of the openings 942, 944 are also contemplated, as would be understood by one of ordinary skill in the art from the above description. The second arm 940 may be shaped to provide a bone contacting surface 946 that corresponds to the shape of the bone that it will engage. The second arm 940 may be, for example, curved or arced as it extends between the first side 910 and the second side 912. The second arm 940 may have, for example, a larger length than the first arm 930.

Figure 103:
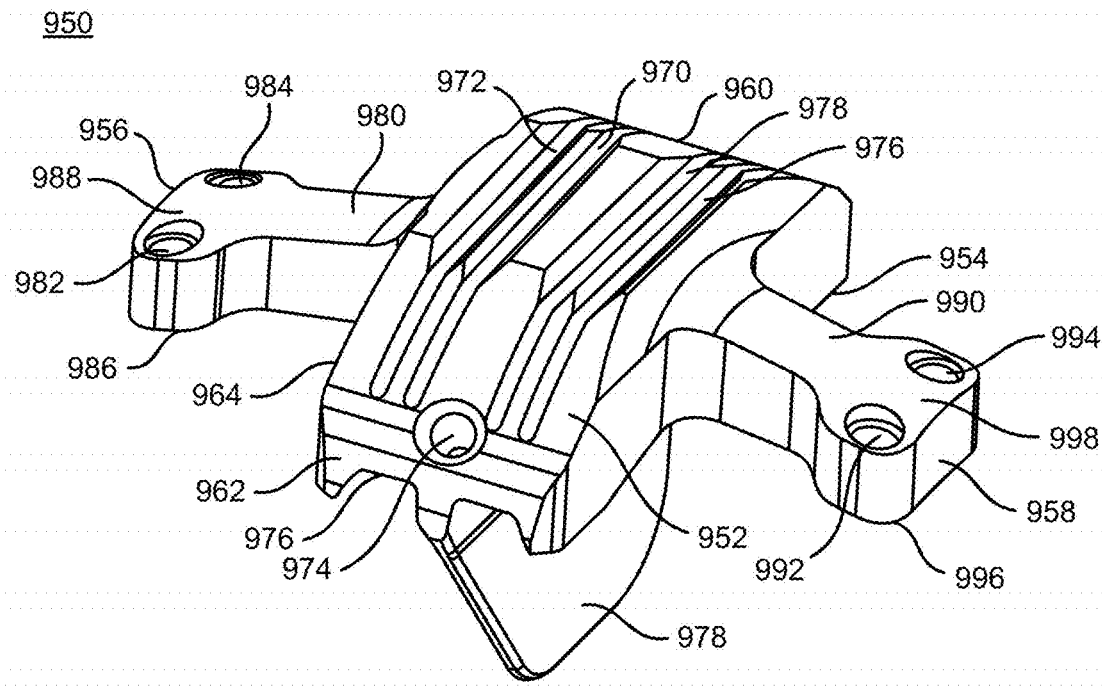
FIG. 103 is a top perspective view of an embodiment of a cut guide, in accordance with an aspect of the present disclosure.
Figure 104:
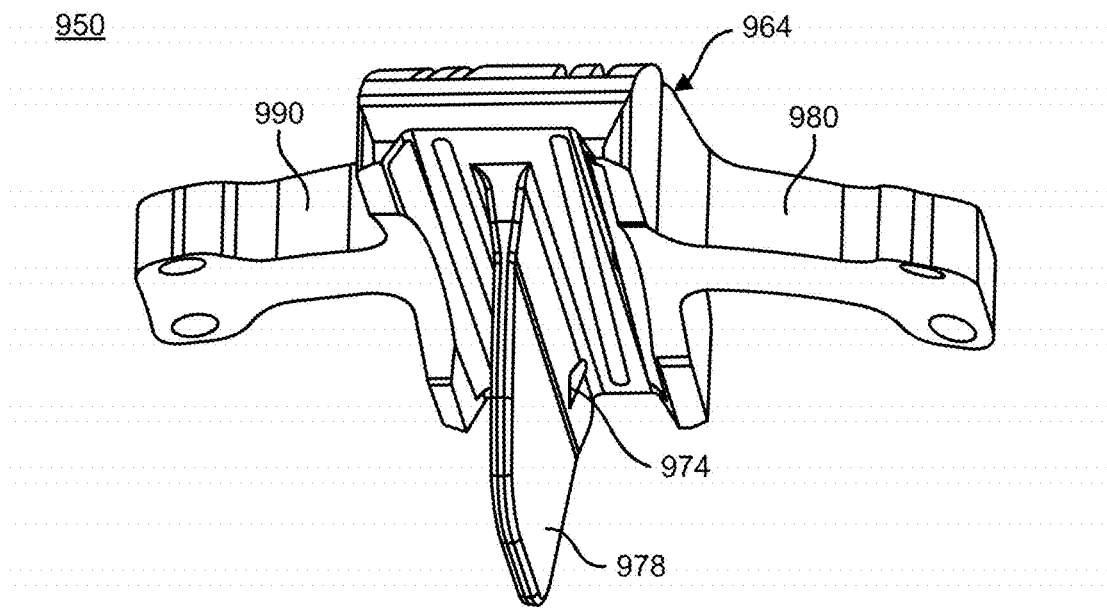
FIG. 104 is a bottom perspective view of the cut guide of FIG. 103, in accordance with an aspect of the present disclosure.

FIGS. 103 and 104 show another cut guide 950. Another cut guide 950 is shown in FIGS. 103 and 104. The cut guide 950 is a mirror image of the cut guide 900 in a medial-lateral direction, which will not be described again in full detail for brevity purposes. For example, the hole 924 is positioned on a left side of the cut guide 900 when in an insertion position and the hole 974 is positioned on a right side of the cut guide 950 when in an insertion position. The cut guide 950 may be, for example, for a left foot. The cut guide 950 may include a top surface 952, a bottom surface 954, a first or proximal end 956, a second or distal end 958, a first or medial side 960, and a second or lateral side 962, which may be of the type described above with respect to the top surface 902, the bottom surface 904, the first or proximal end 906, the second or distal end 908, the first or medial side 910, and the second or lateral side 912, respectively. The cut guide 950 may also include a base portion 964 which may be the mirror image of the base portion 914, as described above. The slots 966, 968, 970, 972, the hole 974, and the recessed region 976 may be the same or similar to the slots 916, 918, 920, 922, the hole 924, and the recessed region 926, as described in greater detail above. Further, the cut guide 950 may include a fin, paddle or extension member 978, a first or proximal arm 980, and a second or distal arm 990, which may be as described above with respect to the extension member 928, the first arm 930, and the second arm 940, respectively. The coupling portion 988, the openings 982, 984 and the bone contacting surface 986 may be as described above with reference to the coupling portion 938, the openings 932, 934 and the bone contacting surface 936 and the coupling portion 998, the openings 992, 994 and the bone contacting surface 996 may be as described above with reference to the coupling portion 948, the openings 942, 944 and the bone contacting surface 946, which will not be described again here for brevity purposes.

Referring now to FIGS. 105-112, a cut guide 1000 is shown. The cut guide 1000 includes a top surface 1002, a bottom surface 1004, a first end 1006, a second end 1008, a first side 1010, and a second side 1012. The first end 1006 may be, for example, a proximal end, and the second end 1008 may be, for example, a distal end, or vice versa. The first side 1010 may be, for example, a medial side, and the second side 1012 may be, for example, a lateral side, or vice versa. The cut guide 1000 also includes a base portion 1014, a paddle, fin or extension member 1022 extending away from the bottom surface 1004 of the base portion 1014, and an arm 1030 extending away from the base portion 1014 on the second end 1008. As shown in FIGS. 105-112, the cut guide 1000 may be, for example, a right foot cut guide. The cut guide 1000 may provide, for example, a 4° angulation from dorsal to plantar on the metatarsal.

Cut guide 1000 may be used, for example, when a surgeon decides that correction of the first metatarsal in plantarflexion is not sufficient enough and needs to take off more of the metatarsal from the dorsal to plantar direction. Alternatively, cut guide 1000 may be used, for example, when a surgeon knows from pre-operative radiographs that the first ray is dorsiflexed in order to cut more bone of the metatarsal plantarly to correct the dorsiflexion. For example, when guide 1000 is used, it will be inserted into the patient's joint, the surgeon will use cut guide 1000 to cut the first metatarsal, then cut guide 1000 will be removed and replaced with another cut guide, such as, cut guide 700, 800, 900, to cut the cuneiform. The second guide 700, 800, 900 will be selected based on the size and desired angular correction of the cuneiform. The cut guide 1000 may be removed from the patient's bones, for example, by sliding the guide 1000 off a guide wire inserted through the opening 1032 and inserting the second cut guide 700, 800, 900 onto the guide wire to properly align the second cut guide 700, 800, 900 on the patient's bones with respect to the first cut made to the metatarsal.

Figure 105:
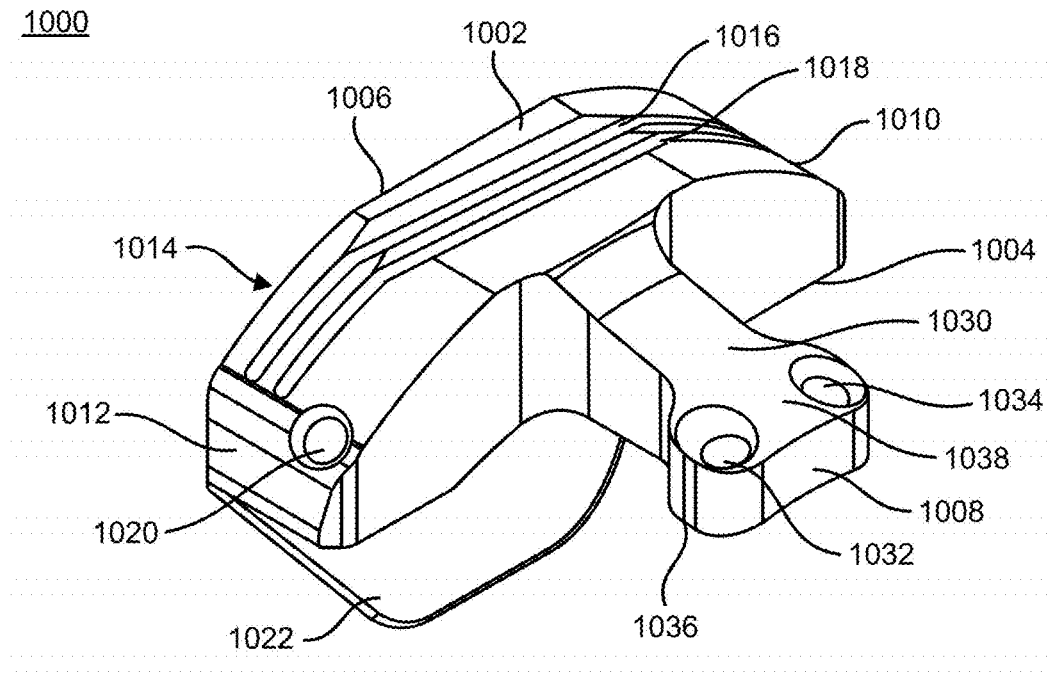
FIG. 105 is a top perspective view of an embodiment of a cut guide, in accordance with an aspect of the present disclosure.
Figure 106:
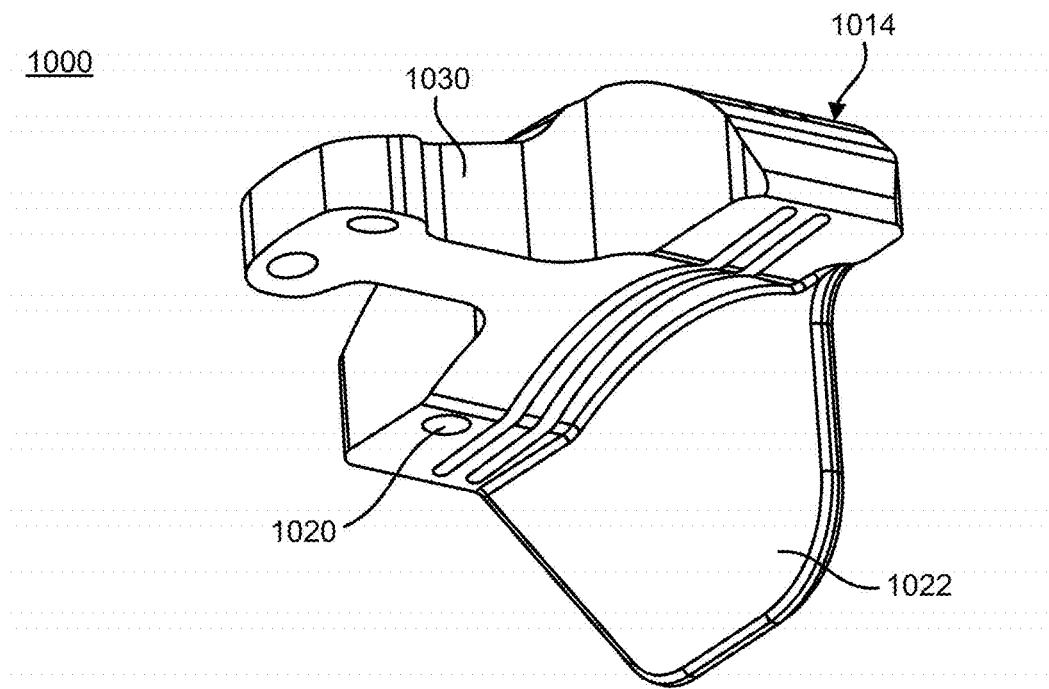
FIG. 106 is a bottom perspective view of the cut guide of FIG. 105, in accordance with an aspect of the present disclosure.
Figure 107:
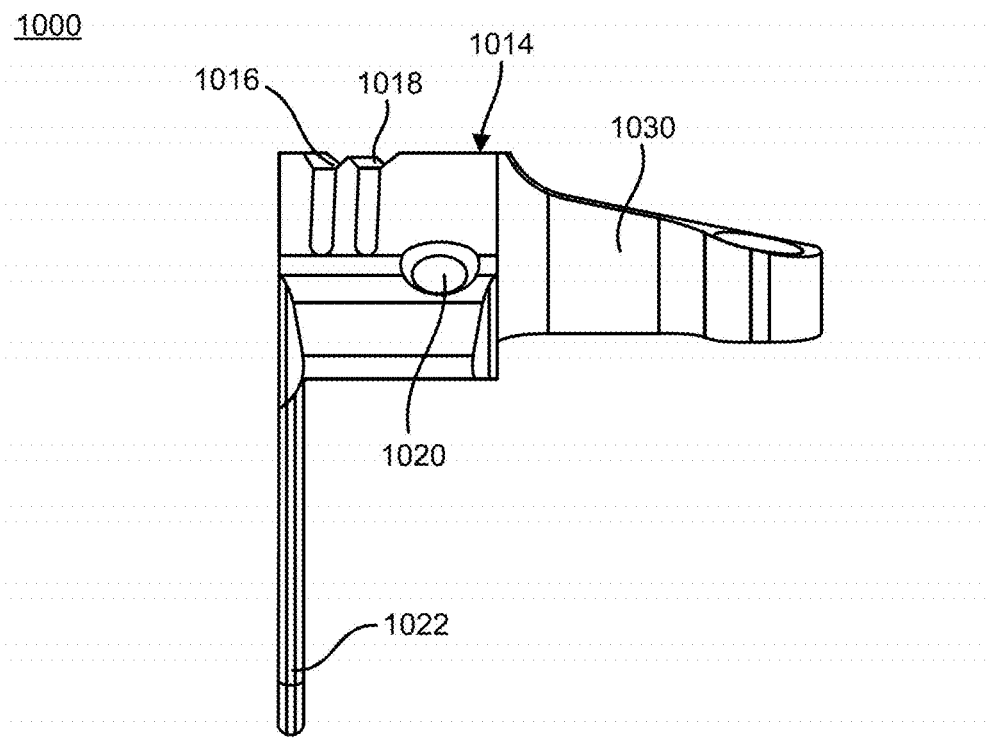
FIG. 107 is a side view of the cut guide of FIG. 105, in accordance with an aspect of the present disclosure.
Figure 108:
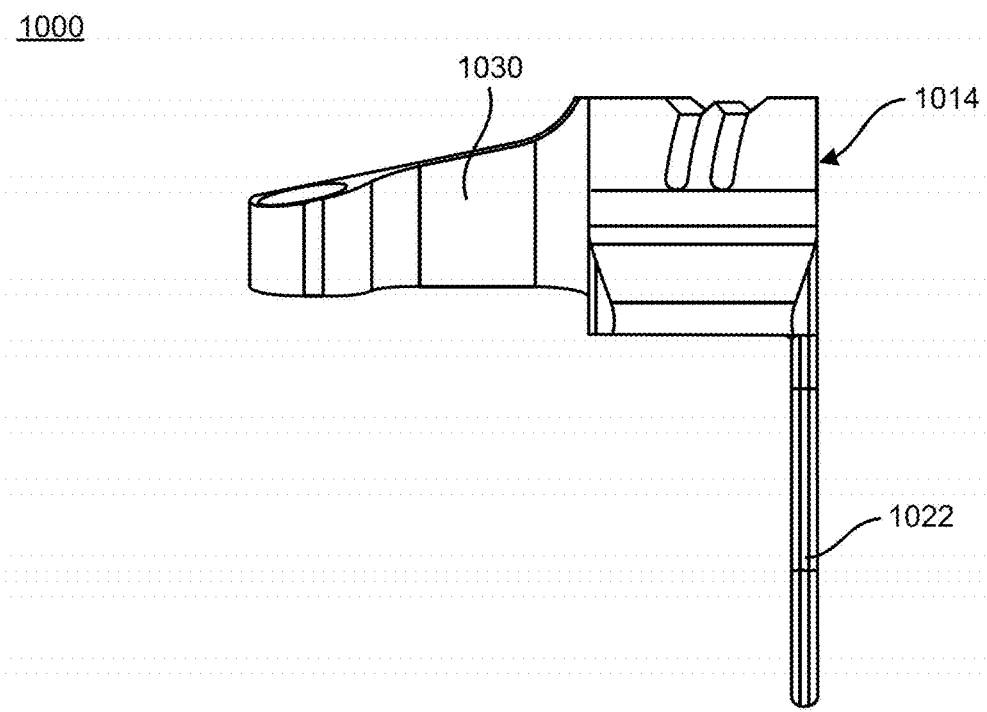
FIG. 108 is another side view of the cut guide of FIG. 105, in accordance with an aspect of the present disclosure.
Figure 109:
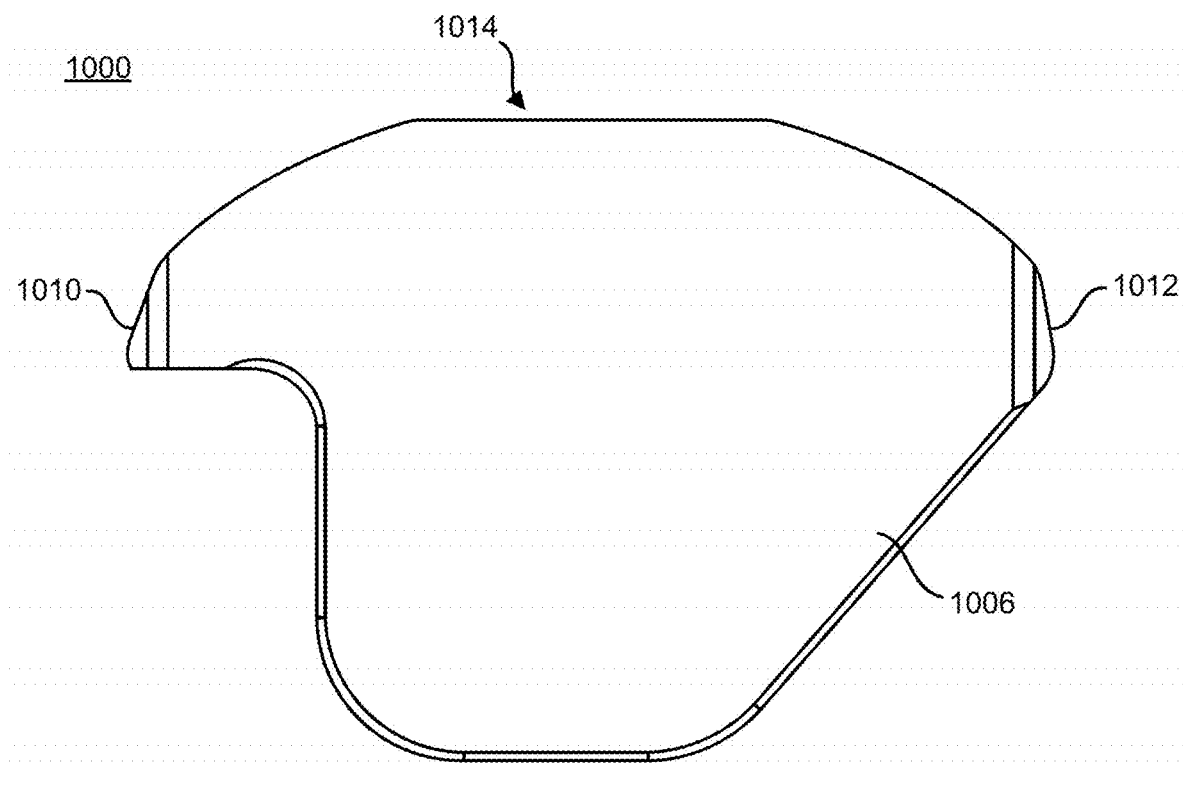
FIG. 109 is an end view of the cut guide of FIG. 105, in accordance with an aspect of the present disclosure.
Figure 110:
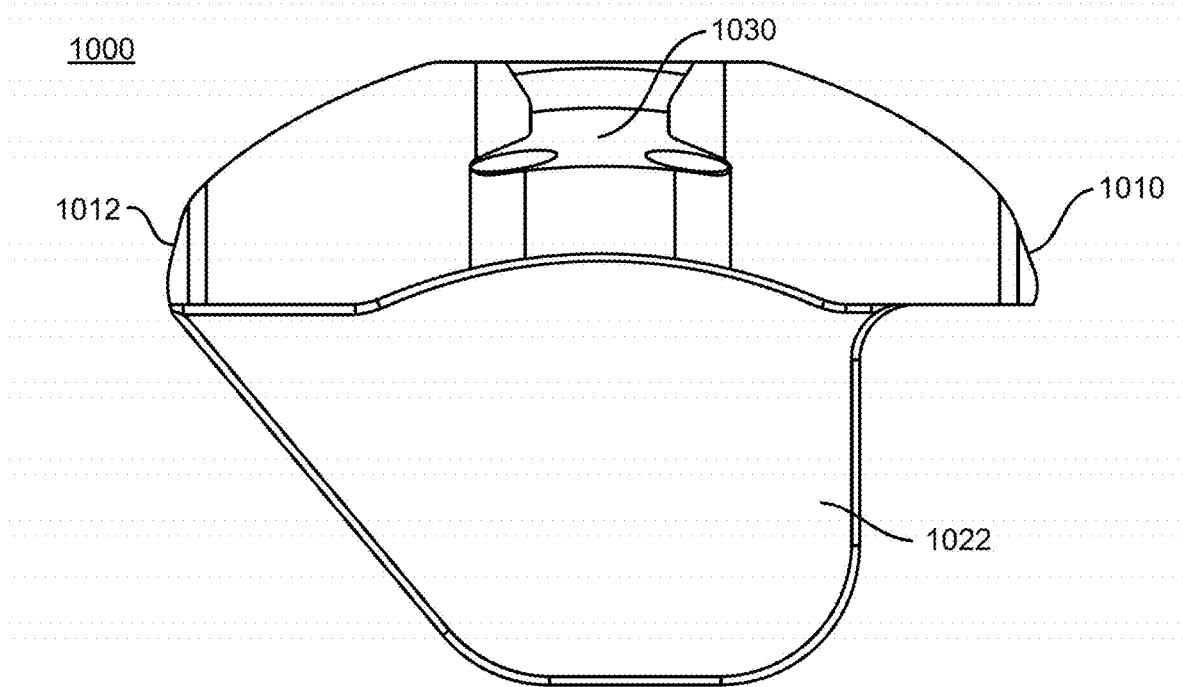
FIG. 110 is another end view of the cut guide of FIG. 105, in accordance with an aspect of the present disclosure.

As shown in FIGS. 105, 109 and 110, the top surface 1002 of the base portion 1014 may be, for example, curved or arced between the first side 1010 and the second side 1012. In an embodiment, the top surface 1002 of the base portion 1014 may include, for example, a flat or planar portion positioned between a first curvature or arc extending from the first side 1010 to the flat portion and a second curvature or arc extending from the second side 1012 to the flat portion. The base portion 1014 also includes at least one slot 1016, 1018, as shown in FIGS. 105-108, 111 and 112. In the depicted embodiment, the first slot 1016 is positioned adjacent to a second slot 1018. The slots 1016, 1018 may extend, for example, through the base portion 1014 from the top surface 1002 to the bottom surface 1004 of the cut guide 1000. The slots 1016, 1018 may be, for example, angled as the slots 1016, 1018 extend from the top surface 1002 to the bottom surface 1004. The slots 1016, 1018 may be angled, for example, approximately 1° to 4° and more specifically, approximately 2°, as the slots 1016, 1018 extend between the top surface 1002 and the bottom surface 1004. It is also contemplated that the interior slot 1016 may be angled while the exterior slot 1018 may be linear as they extend between the top and bottom surfaces 1002, 1004.

Figure 112:
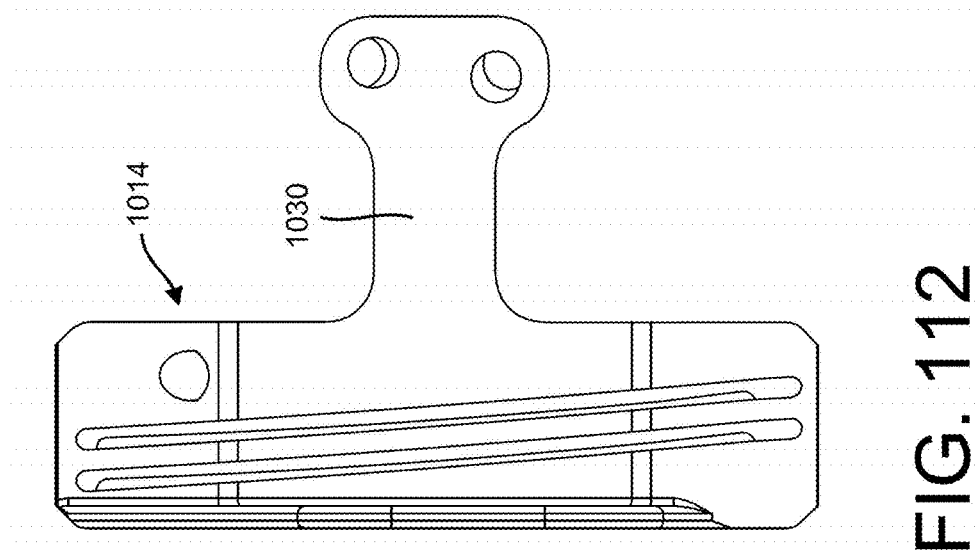
FIG. 112 is a bottom view of the cut guide of FIG. 105, in accordance with an aspect of the present disclosure.
Figure 111:
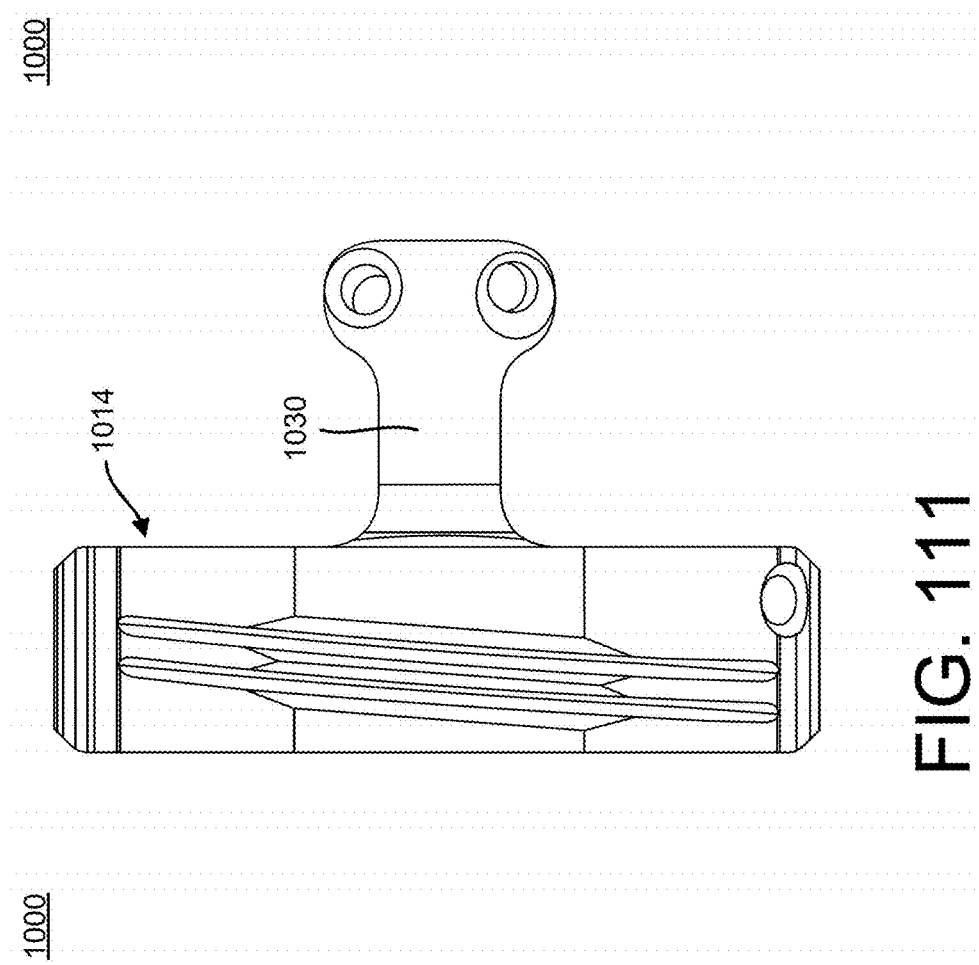
FIG. 111 is a top view of the cut guide of FIG. 105, in accordance with an aspect of the present disclosure.

In addition, the slots 1016, 1018 may be angled as they extend across the base portion 1014 from the first side 1010 to the second side 1012, as shown in FIGS. 111 and 112. The slots 1016, 1018 may be, for example, angled at approximately 6° as they extend between the first and second sides 1010, 1012 providing for an angulation correction of 4°. The slots 1016, 1018 may be configured or sized and shaped to receive a saw blade and may have a width of, for example, approximately 0.58 mm to 0.92 mm. As shown in FIG. 111, the slots 1016, 1018 may be angled from a distal-medial position to a proximal-lateral position of the cut guide 1000.

The slots 1016, 1018 may be positioned, for example, to allow for removal of the articular cartilage only. To prevent resecting too much tissue, the slots 1016, 1018 may be positioned, for example, such that the medial portion of the slots 1016, 1018 are aligned with the cartilage and bone boundary.

The base portion 1014 also includes a hole or dorsal hole 1020, as shown in at least FIGS. 105-107, 111 and 112. The hole 1020 is positioned between the second slot 1018 and the arm 1030. The hole 1020 may extend, for example, through the base portion 1014 from the top surface 1002 to the bottom surface 1004. The hole 1020 may, for example, extend through the base portion 1014 of the cut guide 1000 parallel to the angled portion of the extension member 1022, as shown in FIG. 105. The hole 1020 may be sized and shaped or configured, for example, to receive a wire, alignment wire, k-wire, guide wire, directional wire or the like to provide information on the position of the cut guide 1000 in a joint. For example, the wire inserted into hole 1020 should align approximately with the long axis of the tibia to provide the proper orientation of the cut guide 1000 in the joint, which may be, for example, approximately from dorsal and 45° from medial in the frontal plane.

Referring now to FIGS. 106-110 and 112, the extension member 1022 is attached to a bottom surface 1004 of the base portion 1014. The extension member 1022 also extends away from the base portion 1014 and is positioned on the first end 1006 of the cut guide 1000. In addition, the extension member 1022 extends from the second side 1012 toward the first side 1010, as shown in at least FIGS. 106, 109 and 110. The extension member 1022 may include a portion near the first side 1010 that extends perpendicularly away from the bottom surface 1004. The perpendicular portion of the extension member 1022 may be, for example, angled when the cut guide 1000 is inserted into a patient's joint and the angle that the perpendicular portion is positioned at may correspond to the angle of the first tarsometatarsal joint medially. The extension member 1022 may also include an angled portion extending from the second side 1012 to the end of the extension member 1022. The extension member 1022 may be shaped, for example, to fit within the joint space between the two bones, such as, a first metatarsal and cuneiform, as well as to mate with the two sides of an articular joint. The angled portion of the extension member 1022 may, for example, be oriented laterally and should align with the long axis of the tibia, as well as fit within the joint to rest against the relatively straight surface of the adjacent bone, for example, the second metatarsal. When the angled portion of the extension member 1022 is oriented against the second metatarsal, the cut guide 1000 will be positioned at a angle in the frontal plane.

As shown in FIGS. 105-108 and 110-112, the arm 1030 may extend away from an end of the base portion 1014 and may have, for example, a first portion extending from the base portion 1014 to a coupling portion 1038 positioned at the first end 1006 of the cut guide 1000. The coupling portion 1038 may have a width larger than the width of the first portion of the arm 1030. The coupling portion 1038 of the arm 1030 includes at least one opening 1032, 1034. In the depicted embodiment, the arm 1030 includes a first opening 1032 and a second opening 1034 positioned near the first end 1006. The first opening 1032 may be spaced apart from the second opening 1034. The openings 1032, 1034 may extend from a top surface 1002 to a bottom surface 1004 of the coupling portion 1038 of the cut guide 1000. The openings 1032, 1034 may extend through the coupling portion 1038 of the arm 1030, for example, parallel to the extension member 1028, angled as they extend from the top surface 1002 toward the bottom surface 1004, or a combination of parallel and angled. In one embodiment, the first opening 1032 may extend, for example, parallel to the extension member 1028 and the second opening 1034 may be, for example, angled with respect to the extension member 1028 to permit the inserted wires, guide wires, k-wires and the like to cross above the cut guide 1000 without intersecting. By positioning the openings 1032, 1034 such that inserted wires cross above the openings 1032, 1034 allows for a smaller surgical incision and less interaction or interference with other instruments during the procedure. The openings 1032, 1034 positioning the wires to cross also allows for the cut guide 1000 to be, for example, suspended above and/or proximate to the bone surfaces being cut. The ability to suspend the cut guide 1000 above the bone surfaces prevents the cut guide 1000 from being titled because of varying patient anatomy and this avoids moving the slots 1016, 1018 which would affect the proposed cut angles. Alternative combinations of orientations of the openings 1032, 1034 are also contemplated, as would be understood by one of ordinary skill in the art from the above description. The arm 1030 may be shaped to provide a bone contacting surface 1036 that corresponds to the shape of the bone that it will engage. The arm 1030 may be, for example, curved or arced as it extends between the first side 1010 and the second side 1012.

Figure 113:
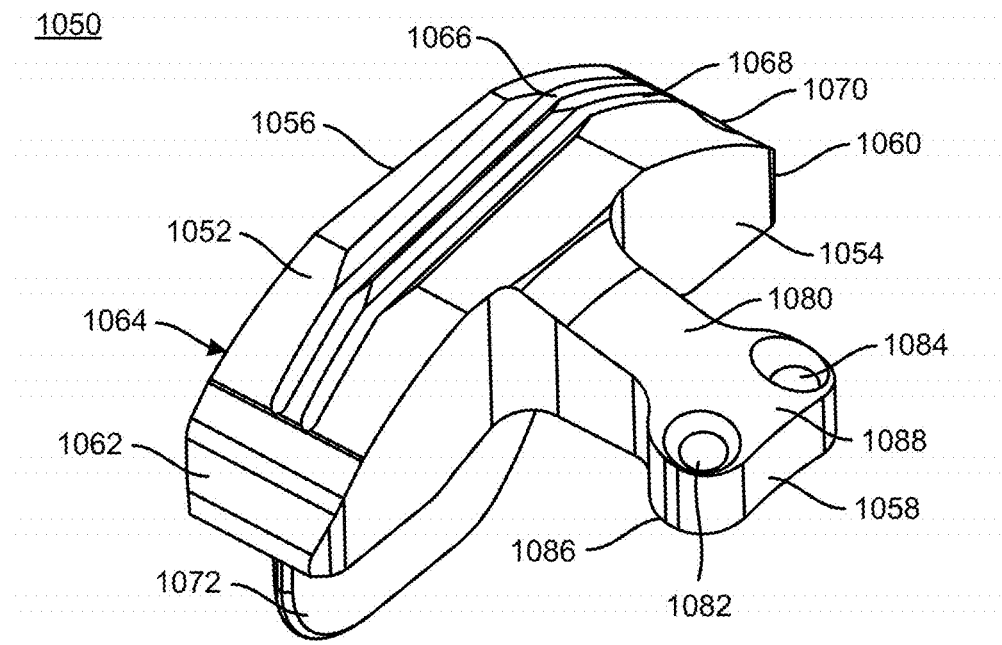
FIG. 113 is a top perspective view of an embodiment of a cut guide, in accordance with an aspect of the present disclosure.
Figure 114:
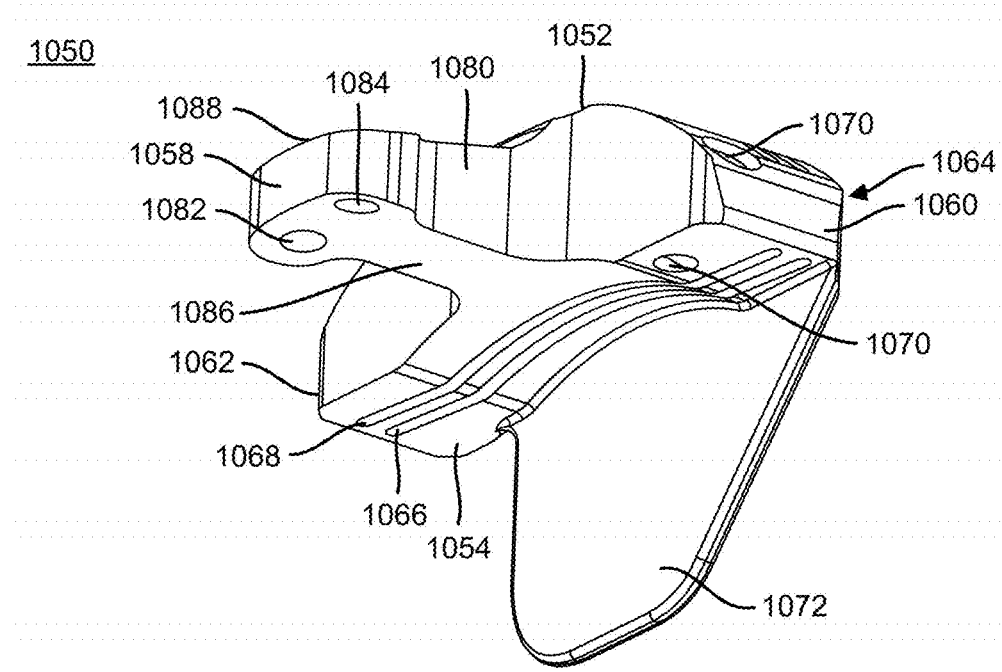
FIG. 114 is a bottom perspective view of the cut guide of FIG. 113, in accordance with an aspect of the present disclosure.

With reference to FIGS. 113 and 114 another cut guide 1050 is shown. As shown, the cut guide 1050 may be a mirror image of the cut guide 1000 in a medial-lateral direction, therefore, the cut guide 1050 will not be described in full detail for brevity purposes. Therefore, the cut guide 1050 may be, for example, for a left foot. The cut guide 1050 may include a top surface 1052, a bottom surface 1054, a first or proximal end 1056, a second or distal end 1058, a first or medial side 1060, and a second or lateral side 1062, which may be as described above with respect to the top surface 1002, the bottom surface 1004, the first or proximal end 1006, the second or distal end 1008, the first or medial side 1010, and the second or lateral side 1012, respectively, which will not be described again here for brevity sake. As the cut guide 1050 is a mirror image of the cut guide 1000, the cut guide 1050 may also include a base portion 1064 which may be the mirror image of the base portion 1014 as described above. In addition, the hole 1020 is positioned on a left side of the cut guide 1000 when in an insertion position and the hole 1070 is positioned on the right side of the cut guide 1050 when in an insertion position. The slots 1066, 1068 and the hole 1070 may be similar to the slots 1016, 1018 and hole 1020, as described in greater detail above. Specifically, as the cut guide 1050 is a mirror image of the cut guide 1000, the slots 1066, 1068 may be angled from a distal-lateral position to a proximal-medial position of the cut guide 1050 resulting in 4° of cumulative dorsal to plantar cutting, as described in greater detail above with reference to cut guide 1000. Further, the cut guide 1050 may include a fin, paddle or extension member 1072 and an arm 1080, which may be as described above with respect to the fin, paddle or extension member 1022 and the arm 1030, respectively. The openings 1082, 1084 and bone contacting surface 1086 may be as described above with reference to the openings 1032, 1034 and bone contacting surface 1036, which will not be described again here for brevity purposes.

As may be recognized by those of ordinary skill in the art based on the teachings herein, numerous changes and modifications may be made to the above-described and other embodiments of the present disclosure without departing from the scope of the disclosure. The components of the guides and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the guides and systems may include more or fewer components or features than the embodiments as described and illustrated herein. For example, the components and features of FIGS. 1-8, FIGS. 9-10, FIGS. 11-18, FIGS. 19-26, FIGS. 27-34, FIGS. 35-36, and FIGS. 37-44, FIGS. 66-74, FIGS. 75-82, FIGS. 83-84, FIGS. 85-92, FIGS. 93-94, FIGS. 95-102, FIGS. 103-104, FIGS. 105-112 and FIGS. 113-114 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

Having thus described the preferred embodiments, the invention is now claimed to be:

1. A cut guide, comprising:
   a base portion, comprising:
     a first side positioned substantially opposite the base portion from a second side;
     a first end positioned substantially opposite the base portion from a second end;
     a top surface positioned substantially opposite the base portion from a bottom surface; and
     at least one slot disposed between the first and second ends of the base portion and extending at least partially between the first side and the second side of the base, wherein the slot provides fluid communication between the top and bottom surfaces of the base;
     at least one opening extending therethrough; and
   an extension member extending downward from the bottom surface of the base, wherein the at least one opening extends into at least a portion of the extension member.

2. The cut guide of claim 1, wherein the at least one slot comprises at least one first slot and at least one second slot.

3. The cut guide of claim 2, wherein the extension member is positioned at least partially between the at least one first slot and the at least one second slot.

4. The cut guide of claim 3, wherein the extension member extends from the bottom surface of the base portion at a substantially orthogonal angle relative to the bottom surface of the base portion.

5. The cut guide of claim 4, wherein the at least one first slot is positioned in a first plane and the at least one second slot is positioned in a second plane, wherein the first and second planes form an oblique angle.

6. The cut guide of claim 5, wherein the at least one opening provides fluid communication between the top and bottom surfaces of the base portion.

7. The cut guide of claim 6, wherein the cut guide further comprises a first arm extending from the first end of the base portion.

8. The cut guide of claim 7, wherein the first arm forms a substantially orthogonal angle with the first end of the base portion.

9. The cut guide of claim 8, wherein the first arm comprises a first opening extending therethrough from a top surface through to a bottom surface thereof.

10. The cut guide of claim 9, wherein the first opening is positioned at a terminal end of the first arm.

11. The cut guide of claim 10, wherein the cut guide further comprises a second arm extending from the second end of the base portion.

12. The cut guide of claim 11, wherein the second arm forms a substantially orthogonal angle with the second end of the base portion.

13. The cut guide of claim 12, wherein the second arm comprises a second opening extending therethrough from a top surface through to a bottom surface thereof.

14. The cut guide of claim 13, wherein the second opening is positioned at a terminal end of the second arm.

15. The cut guide of claim 1, wherein the top surface comprises a first portion and a second portion.

16. The cut guide of claim 15, wherein the first portion is positioned in a plane which is substantial parallel to a plane of the bottom surface, and the second portion is positioned in a plane which is substantially oblique to that of the first portion and the bottom surface.

17. The cut guide of claim 16, wherein at least a portion of the at least one slot is positioned in the first portion of the top surface and the second portion of the top surface.

18. A cut guide, comprising:
   a base portion, comprising:
     a first end positioned substantially opposite the base portion from a second end;
     a top surface positioned substantially opposite the base portion from a bottom surface, comprising:
       a first portion positioned in a first plane; and
       a second portion positioned in a second plane, wherein the second plane is substantially oblique to the first plane;

at least one slot disposed between the first and second ends of the base portion, wherein the at least one slot provides fluid communication between the top and bottom surfaces of the base, wherein at least a portion of the at least one slot is positioned in the first portion and the second portion of the top surface; and at least one opening extending through the base portion; and an extension member extending downward from the bottom surface of the base, wherein the at least one opening extends into at least a portion of the extension member.

19. The cut guide of claim 18, wherein the at least one slot comprises a first slot and a second slot, wherein the first and second slots are positioned in planes which form an oblique angle with one another.

20. A cut guide, comprising:
a base portion, comprising:
  a first side positioned substantially opposite the base portion from a second side, wherein the first and second sides are substantially parallel to one another;
  a first end positioned substantially opposite the base portion from a second end;
  a top surface positioned substantially opposite the base portion from a bottom surface, comprising:
    a first portion positioned in a first plane; and
    a second portion positioned in a second plane, wherein the second plane is substantially oblique to the first plane;
  at least one slot disposed between the first and second ends of the base portion, wherein the at least one slot provides fluid communication between the top and bottom surfaces of the base, wherein at least a portion of the at least one slot is positioned in the first portion and the second portion of the top surface; and
  at least one opening extending from the top surface through to the bottom surface;
an extension member extending downward from the bottom surface of the base, wherein the at least one opening extends into at least a portion of the extension member;
a first arm extending from the first end of the base portion at a substantially orthogonal angle, comprising:
  an opening positioned at a terminal end of the first arm and extending from a top surface of the first arm through to a bottom surface of the first arm; and
a second arm extending from the second end of the base portion, comprising:
  an opening positioned at a terminal end of the second arm and extending from a top surface of the second arm through to a bottom surface of the second arm.

* * * * *